United States Patent
Jun et al.

(10) Patent No.: US 10,836,824 B2
(45) Date of Patent: Nov. 17, 2020

(54) ANTIBODIES DIRECTED AGAINST LYMPHOCYTE ACTIVATION GENE 3 (LAG-3)

(71) Applicant: AnaptysBio, Inc., San Diego, CA (US)

(72) Inventors: Helen Toni Jun, San Diego, CA (US);
Marilyn Kehry, San Diego, CA (US);
Peter Bowers, San Diego, CA (US);
David J. King, Encinitas, CA (US)

(73) Assignee: ANAPTYSBIO, INC., San Diego, CA (US)

( * ) Notice: Subject to any disclaimer, the term of this patent is extended or adjusted under 35 U.S.C. 154(b) by 335 days.

(21) Appl. No.: 15/548,405

(22) PCT Filed: Feb. 3, 2016

(86) PCT No.: PCT/US2016/016424
§ 371 (c)(1),
(2) Date: Aug. 2, 2017

(87) PCT Pub. No.: WO2016/126858
PCT Pub. Date: Aug. 11, 2016

(65) Prior Publication Data
US 2018/0127496 A1 May 10, 2018

Related U.S. Application Data

(60) Provisional application No. 62/111,486, filed on Feb. 3, 2015.

(51) Int. Cl.
| *C07K 16/00* | (2006.01) |
| *C07K 16/28* | (2006.01) |
| *A61P 31/00* | (2006.01) |
| *A61P 35/00* | (2006.01) |
| *A61K 39/395* | (2006.01) |
| *A61K 39/00* | (2006.01) |

(52) U.S. Cl.
CPC ...... *C07K 16/2803* (2013.01); *A61K 39/3955* (2013.01); *A61P 31/00* (2018.01); *A61P 35/00* (2018.01); *C07K 16/2818* (2013.01); *A61K 2039/505* (2013.01); *A61K 2039/507* (2013.01); *C07K 2317/24* (2013.01); *C07K 2317/524* (2013.01); *C07K 2317/70* (2013.01); *C07K 2317/71* (2013.01); *C07K 2317/76* (2013.01); *C07K 2317/92* (2013.01); *C07K 2317/94* (2013.01); *C07K 2319/30* (2013.01); *C07K 2319/32* (2013.01); *Y02A 50/386* (2018.01)

(58) Field of Classification Search
None
See application file for complete search history.

(56) References Cited

U.S. PATENT DOCUMENTS

| 4,828,981 | A | 5/1989 | Maggio |
| 5,122,464 | A | 6/1992 | Wilson et al. |
| 5,464,758 | A | 11/1995 | Gossen et al. |
| 5,770,359 | A | 6/1998 | Wilson et al. |
| 5,814,618 | A | 9/1998 | Bujard et al. |
| 6,143,273 | A | 11/2000 | Faure et al. |
| 7,112,715 | B2 | 9/2006 | Chambon et al. |
| 8,551,481 | B2 | 10/2013 | Pardoll et al. |
| 8,568,992 | B2 | 10/2013 | Walker et al. |
| 9,005,629 | B2 | 4/2015 | Pardoll et al. |
| 9,505,839 | B2 | 11/2016 | Longberg et al. |
| 2009/0093024 | A1 | 4/2009 | Bowers et al. |
| 2010/0233183 | A1 | 9/2010 | Triebel et al. |
| 2011/0150892 | A1 | 6/2011 | Thudium et al. |
| 2011/0287485 | A1 | 11/2011 | Bowers et al. |
| 2013/0224188 | A1 | 8/2013 | Eckelman et al. |
| 2014/0093511 | A1 | 4/2014 | Lonberg et al. |
| 2015/0307620 | A1 | 10/2015 | Vella et al. |
| 2016/0015805 | A1 | 1/2016 | Azab et al. |
| 2016/0108121 | A1 | 4/2016 | Pardoll et al. |
| 2016/0176962 | A1 | 6/2016 | Murriel et al. |
| 2019/0256596 | A1 | 8/2019 | Jun et al. |

FOREIGN PATENT DOCUMENTS

| JP | 2012500006 | 1/2012 |
| WO | WO 1992/008796 A1 | 5/1992 |
| WO | WO 1994/028143 A1 | 12/1994 |
| WO | WO 2008/132601 A1 | 11/2008 |
| WO | WO 2010/019570 A2 | 2/2010 |
| WO | WO 2010/019570 A3 | 2/2010 |
| WO | WO 2014/008218 A1 | 1/2014 |

(Continued)

OTHER PUBLICATIONS

Colman et al., Research in Immunology (145(1):33-36, 1994).*
Abaza et al., Journal of Protein Chemistry 1992 (11(5):433-444, 1992.*
Lederman et al Molecular Immunology (28:1171-1181, 1991).*
Wang et al. (JBC 276:49213-49220.*
Rudikoff et al (Proc Natl Acad Sci USA 1982 vol. 79 p. 1979.*
Edwards et al., JMB 2003, v.334,pp. 103-118.*
Lloyd et al., 2009, Protein Engineering, v.22, pp. 159-168.*
Van Noort et al. (International Review of Cytology, 1998.*
Mestas et al (J. Of Immunology, 2004, 172, pp. 2731-238.*
Shanks et al (Philosophy, Ethics and Humanities in Medicine, 2009, v.4, pp. 1-20.*

(Continued)

*Primary Examiner* — Michail A Belyavskyi
(74) *Attorney, Agent, or Firm* — Fish & Richardson P.C.

(57) ABSTRACT

The invention relates to an isolated immunoglobulin heavy chain polypeptide and an isolated immunoglobulin light chain polypeptide that bind to a protein encoded by the Lymphocyte Activation Gene-3 (LAG-3). The invention provides a LAG-3-binding agent that comprises the aforementioned immunoglobulin heavy chain polypeptide and immunoglobulin light chain polypeptide. The invention also provides related vectors, compositions, and methods of using the LAG-3-binding agent to treat a disorder or disease that is responsive to LAG-3 inhibition, such as cancer or an infectious disease.

10 Claims, 4 Drawing Sheets

Specification includes a Sequence Listing.

(56) References Cited

FOREIGN PATENT DOCUMENTS

| WO | WO 2014/089493 A1 | 6/2014 |
|---|---|---|
| WO | WO 2014/140180 A1 | 9/2014 |
| WO | WO 2015/143343 A2 | 9/2015 |
| WO | WO 2015/179799 A1 | 11/2015 |
| WO | WO 2016/070051 A2 | 5/2016 |
| WO | WO 2016/200782 | 12/2016 |

OTHER PUBLICATIONS

Vaguer et al., 2013, Nature v.12, pp. 287-305.*
Altschul et al., *J. Molecular Biol.*, 215(3): 403-410 (1990).
Altschul et al., *Nucleic Acids Res.*, 25(17): 3389-3402 (1997).
Baixeras et al., *J. Exp. Med.*, 176: 327-337 (1992).
Beigert et al., *Proc. Natl. Acad. Sci. USA*, 106(10): 3770-3775 (2009).
Bird et al., *Science*, 242: 423-426 (1988).
Bhatia et al., *Curr. Oncol. Rep.*, 13(6): 488-497 (2011).
Braitbard et al., "Competition between bound and free peptides in an ELISA-based procedure that assays peptides derived from protein digests," *Proteome Science.*, 4(12): (2006).
Blackburn et al., *Nat. Immunol.*, 10: 29-37 (2009).
Bowers et al. *Proc. Natl. Acad. Sci. USA*, 108(51): 20455-20460 (2011).
Bowers et al., *J. Biol. Chem.*, 288(11):7688-7696 (2013).
Brash et al., *Mol. Cell Biol.*, 7: 2031-2034 (1987).
Bruniquel et al., *Immunogenetics*, 47: 96-98 (1997).
Casati et al., *Cancer Res.*, 66: 4450-4460 (2006).
Casati et al., *J. Immunol*, 180: 3782-3788 (2008).
Colbére-Garapin et al., "A new dominant hybrid selective marker for higher eukaryotic cells." *Journal of molecular biology* 150(1): 1-14 (1981).
Conese et al., "Gene therapy progress and prospects: episomally maintained self-replicating systems." *Gene therapy* 11(24): 1735-1741 (2004).
David et al., "Protein iodination with solid state lactoperoxidase." *Biochemistry* 13(5): 1014-1021 (1974).
Durham et al., *PLoS ONE*, 9(11): e109080 (2014).
El Mir et al, *J. Immunol.*, 164: 5583-5589 (2000).
Fuhrmann-Benzakein et al. "Inducible and irreversible control of gene expression using a single transgene." *Nucleic acids research* 28(23): e99-e99 (2000).
Goeddel, *Gene Expression Technology: Methods in Enzymology*, 185: Academic Press, San Diego, Calif. (1990).
Grosso et al., *J. Clin. Invest.*, 117: 3383-92 (2007).
Holliger et al., "Engineered antibody fragments and the rise of single domains." *Nature biotechnology* 23(9): 1126-1136 (2005).
Horlick et al., *Gene*, 243(1-2): 187-194 (2000).
Horlick et al., *J. Biol. Chem.*, 288(27): 19861-19869 (2013).
Hotzel et al., *mAbs*, 4: 753-760 (2012).
Hou et al., *J. Biochem.*, 144(1): 115-120 (2008).
Huang et al. *Immunity*, 21: 503-513 (2004).
Huard et al., *Eur. J. Immunol.*, 24: 3216-3221 (1994).
Huard et al., *Eur. J. Immunol.*, 26: 1180-1186 (1996).
Huard et al., *Proc. Natl. Acad. Sci. USA*, 94(11): 5744-5749 (1997).
Hunter et al., "Preparation of Iodine-131 Labelled Human Growth Hormone of High Specific Activity," *Nature*, 194: 495-496 (1962).
Huston et al., "Protein engineering of antibody binding sites: Recovery of specific activity in an anti-digoxin single-chain Fv analogue produced in *Escherichia coli,*" *Proc. Natl. Acad. Sci. USA*, 85: 5879-5883 (1988).
Indra et al., "Temporally-controlled site-specific mutagenesis in the basal layer of the epidermis: comparison of the recombinase activity of the tamoxifen-inducible Cre-ERT and Cre-ERT2 recombinases." *Nucleic acids research* 27(22): 4324-4327 (1999).
Iouzalen et al., *Eur. J. Immunol.*, 31: 2885-2891 (2001).
Janeway et al., Immunobiology: the immune system in health and disease, 6th Ed., Chapter 7 (2005).
Jack et al., *Proc. Natl. Acad. Sci. USA*, 85: 1581-1585 (1988).
Johnston, "Biolistic transformation: microbes to mice." *Nature (London)* 346(6286): 776-777 (1990).
Kashmiri et al., *Methods*, 36(1): 25-34 (2005).
Kearney et al., *J. Immunol.*, 123: 1548-1550 (1979).
Kent et al., *Science*, 237: 901-903 (1987).
Kitts et al., "A method for producing recombinant baculovirus expression vectors at high frequency." *Biotechniques* 14(5): 810-817 (1993).
Köhler et al., "Derivation of specific antibody-producing tissue culture and tumor lines by cell fusion," *Eur. J. Immunol.*, 6: 511-519 (1976).
Kramer et al., "Transgene Control Engineering in Mammalian Cells," *Methods Molecular Biology*, 308: 123-143 (2005).
Lonberg, *Nat. Biotechnol.*, 23(9): 1117-25 (2005).
Lonberg, *Handb. Exp. Pharmacol.*, 181: 69-97 (2008).
Lowy et al., *Cell*, 22: 817-823 (1980).
Luckow et al. "Efficient generation of infectious recombinant baculoviruses by site-specific transposon-mediated insertion of foreign genes into a baculovirus genome propagated in *Escherichia coli.*" *Journal of virology* 67(8): 4566-4579 (1993).
Luckow "Baculovirus systems for the expression of human gene products." *Current opinion in biotechnology* 4(5): 564-572 (1993):.
Mcconnell et al., *Protein Eng. Des. Sel.*, 26: 151 (2013).
Mulligan et al., *Proc. Natl. Acad. Sci. USA*, 78: 2072-2076 (1981).
Ngiow et al., *Cancer Res.*, 71: 3540-3551 (2011).
No et al., *Proc. Natl. Acad. Sci.*, 93: 3346-3351 (1996).
Nygren, *Histochem. and Cytochem.*, 30: 407-412 (1982).
O'Hare et al., *Proc. Natl. Acad. Sci. USA*, 78: 1527-1531 (1981).
Osbourn et al., *Nat. Biotechnol.*, 16: 778 (1998).
Pain et al., "Preparation of protein A-peroxidase monoconjugate using a heterobifunctional reagent, and its use in enzyme immunoassays." *Journal of immunological methods* 40(2): 219-230 (1981):.
Prigent et al., *Eur. J. Immunol.*, 29: 3867-3876 (1999).
Richter et al., *Int. Immunol.*, 22: 13-2 (2010).
Sakuishi et al., *J. Exp. Med.*, 207: 2187-2194 (2010).
Santerre et al., "Expression of prokaryotic genes for hygromycin B and G418 resistance as dominant-selection markers in mouse L cells." *Gene* 30(1): 147-156 (1984).
Sierro et al., *Expert Opin. Ther. Targets*, 15(1): 91-101 (2011).
Söding, "Protein homology detection by HMM-HMM comparison." *Bioinformatics* 21(7): 951-960 (2005).
St. Groth et al., *J. Immunol. Methods*, 35: 1-21 (1980).
Szybalska et al., *Proc. Natl. Acad. Sci. USA*, 48: 2026-2034 (1962).
Triebel et al., *J. Exp. Med.*, 171(5): 1393-1405 (1990).
Triebel F., *Trends Immunol.*, 24(12): 619-22 (2003).
Urlaub et al., *Proc. Natl. Acad. Sci. USA*, 97: 4216-4220 (1980).
Wigler et al., *Cell*, 11: 223-232 (1977).
Wigler et al., *Proc. Natl. Acad. Sci. USA*, 77: 3567-3570 (1980).
Woo et al., *Cancer Res.*, 72: 917-927 (2012).
Workman et al., *J. Immunol.*, 174: 688-695 (2005).
Zola, *Monoclonal Antibodies: A Manual of Techniques*, CRC Press, Inc. (1987).
United States Patent and Trademark Office, International Search Report and Written Opinion for International Application No. PCT/US2016/016424 (dated Jul. 21, 2016).
Andrews et al., "Lag3 (CD223) as a cancer immunotherapy target" Immunological Reviews, 276: 80-96 (2017).
European Patent Office, Extended European Search Report for European Application No. 16747220.8 (dated Jun. 22, 2018).
Brown et al., "Tolerance to Single, but Not Multiple, Amino Acid Replacements in Antibody V, CDR2," *The Journal of Immunology*, 156: 3285-3291 (1996).
Eurasian Patent Office, Official Action for Eurasian Application No. 201791742/28. (dated Nov. 29, 2019).
JP Office Action in Japanese Appln No. 540834/2017, dated Nov. 26, 2019, 9 pages (with English translation).
PCT International Preliminary Report on Patentability in International Appln. No. PCT/US2016/016424, dated Aug. 8, 2017, 8 pages.

* cited by examiner

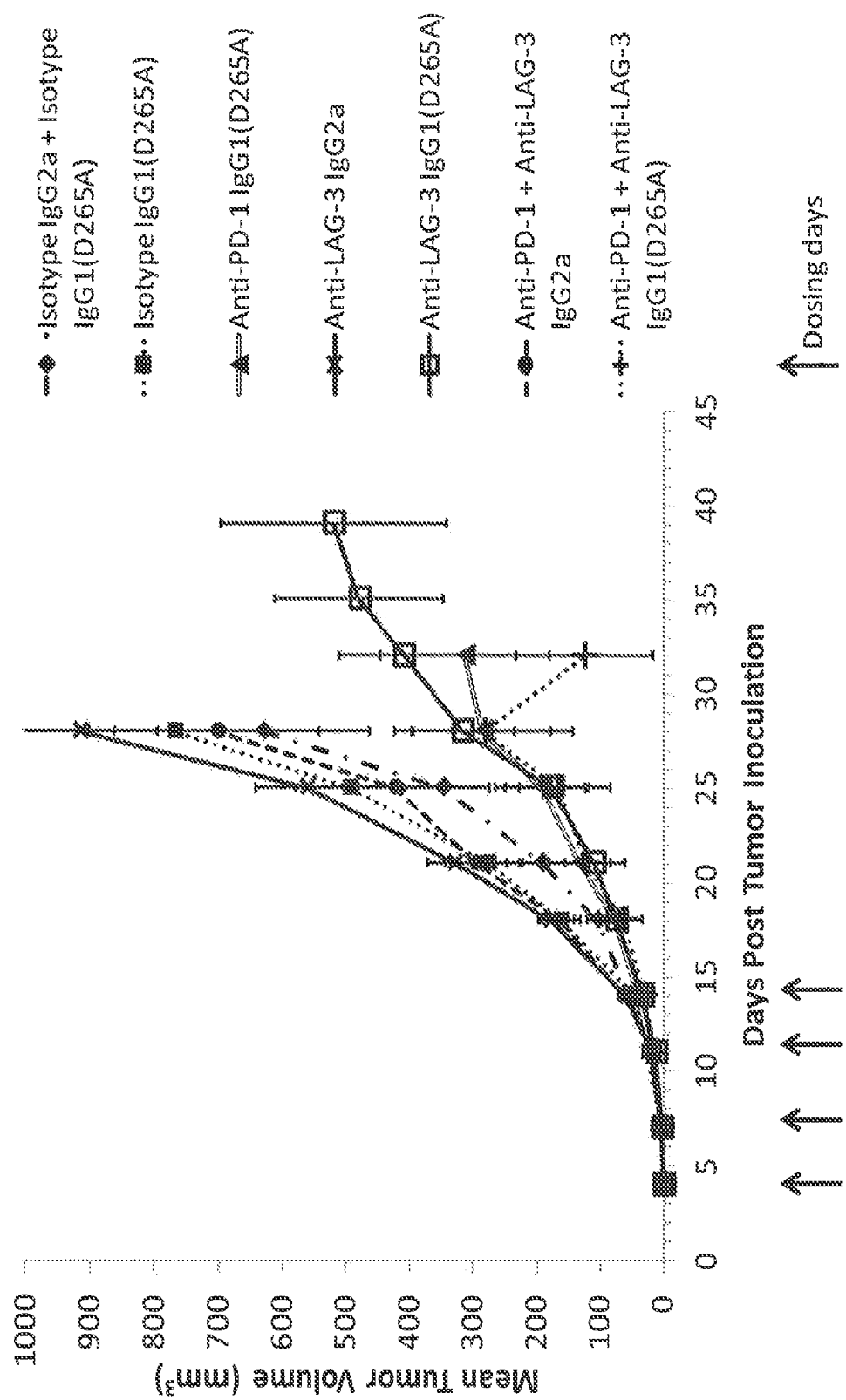

SEQUENCE LISTING

```
<160> NUMBER OF SEQ ID NOS: 200

<210> SEQ ID NO 1
<211> LENGTH: 114
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (28)..(28)
<223> OTHER INFORMATION: Xaa1 is asparagine (Asn) or serine (Ser)
<220> FEATURE:
<221> NAME/KEY: MISC_FEATURE
<222> LOCATION: (30)..(30)
<223> OTHER INFORMATION: Xaa2 is lysine (Lys), tyrosine (Tyr), or
      asparagine (Asn)
<220> FEATURE:
<221> NAME/KEY: MISC_FEATURE
<222> LOCATION: (38)..(38)
<223> OTHER INFORMATION: Xaa3 is lysine (Lys) or glutamine (Gln)
```

```
<220> FEATURE:
<221> NAME/KEY: MISC_FEATURE
<222> LOCATION: (48)..(48)
<223> OTHER INFORMATION: Xaa4 is isoleucine (Ile) or methionine (Met)
<220> FEATURE:
<221> NAME/KEY: MISC_FEATURE
<222> LOCATION: (53)..(53)
<223> OTHER INFORMATION: Xaa5 is alanine (Ala) or proline (Pro)
<220> FEATURE:
<221> NAME/KEY: MISC_FEATURE
<222> LOCATION: (56)..(56)
<223> OTHER INFORMATION: Xaa6 is glycine (Gly), asparagine (Asn), or
      aspartic acid (Asp)
<220> FEATURE:
<221> NAME/KEY: MISC_FEATURE
<222> LOCATION: (61)..(61)
<223> OTHER INFORMATION: Xaa7 is alanine (Ala) or serine (Ser)
<220> FEATURE:
<221> NAME/KEY: MISC_FEATURE
<222> LOCATION: (65)..(65)
<223> OTHER INFORMATION: Xaa8 is glutamine (Gln) or arginine (Arg)
<220> FEATURE:
<221> NAME/KEY: MISC_FEATURE
<222> LOCATION: (77)..(77)
<223> OTHER INFORMATION: Xaa9 is aspartic acid (Asp) or asparagine (Asn)

<400> SEQUENCE: 1

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Xaa Ile Xaa Asp Asp
            20                  25                  30

Tyr Ile His Trp Val Xaa Gln Ala Pro Gly Lys Gly Leu Glu Trp Xaa
        35                  40                  45

Gly Trp Ile Asp Xaa Glu Asn Xaa Asp Ser Glu Tyr Xaa Ser Lys Phe
50                  55                  60

Xaa Gly Arg Val Thr Ile Thr Val Asp Thr Ser Thr Xaa Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 2
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 2

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Asp
            20                  25                  30

Tyr Ile His Trp Val Lys Gln Ala Pro Gly Lys Gly Leu Glu Trp Ile
        35                  40                  45

Gly Trp Ile Asp Pro Glu Asn Gly Asp Ser Glu Tyr Ala Ser Lys Phe
50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95
```

```
Thr Tyr Ala Phe Gly Gly Tyr Trp Gly Gln Gly Thr Thr Val Thr Val
                100                 105                 110
Ser Ser

<210> SEQ ID NO 3
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 3

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Lys Asp Asp
                20                  25                  30

Tyr Ile His Trp Val Lys Gln Ala Pro Gly Lys Gly Leu Glu Trp Ile
            35                  40                  45

Gly Trp Ile Asp Pro Glu Asn Gly Asp Ser Glu Tyr Ala Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
                100                 105                 110

Ser Ser

<210> SEQ ID NO 4
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 4

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Asp
                20                  25                  30

Tyr Ile His Trp Val Lys Gln Ala Pro Gly Lys Gly Leu Glu Trp Ile
            35                  40                  45

Gly Trp Ile Asp Pro Glu Asn Asn Asp Ser Glu Tyr Ala Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
                100                 105                 110

Ser Ser

<210> SEQ ID NO 5
<211> LENGTH: 114
<212> TYPE: PRT
<213> ORGANISM: Artificial Sequence
<220> FEATURE:
<223> OTHER INFORMATION: Synthetic Sequence
```

<400> SEQUENCE: 5

```
Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Asp
            20                  25                  30

Tyr Ile His Trp Val Lys Gln Ala Pro Gly Lys Gly Leu Glu Trp Ile
        35                  40                  45

Gly Trp Ile Asp Pro Glu Asn Gly Asp Ser Glu Tyr Ser Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser
```

<210> SEQ ID NO 6
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 6

```
Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Pro Glu Asn Gly Asp Ser Glu Tyr Ala Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser
```

<210> SEQ ID NO 7
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 7

```
Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Asp
            20                  25                  30

Tyr Ile His Trp Val Lys Gln Ala Pro Gly Lys Gly Leu Glu Trp Ile
        35                  40                  45

Gly Trp Ile Asp Pro Glu Asn Asp Asp Ser Glu Tyr Ala Ser Lys Phe
    50                  55                  60
```

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Val Thr Val
            100                 105                 110

Ser Ser

<210> SEQ ID NO 8
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 8

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Tyr Asp Asp
                20                  25                  30

Tyr Ile His Trp Val Gln Ala Pro Gly Lys Gly Leu Glu Trp Met
            35                  40                  45

Gly Trp Ile Asp Pro Glu Asn Gly Asp Ser Glu Tyr Ala Ser Lys Phe
50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Val Thr Val
            100                 105                 110

Ser Ser

<210> SEQ ID NO 9
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 9

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Tyr Asp Asp
                20                  25                  30

Tyr Ile His Trp Val Gln Ala Pro Gly Lys Gly Leu Glu Trp Met
            35                  40                  45

Gly Trp Ile Asp Pro Glu Asn Gly Asp Ser Glu Tyr Ala Ser Lys Phe
50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Val Thr Val
            100                 105                 110

Ser Ser

```
<210> SEQ ID NO 10
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 10
```

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Pro Glu Asn Gly Asp Ser Glu Tyr Ala Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

```
<210> SEQ ID NO 11
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 11
```

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Asn Asp Asp
            20                  25                  30

Tyr Ile His Trp Val Gln Gln Ala Pro Gly Lys Gly Leu Glu Trp Met
        35                  40                  45

Gly Trp Ile Asp Pro Glu Asn Gly Asp Ser Glu Tyr Ala Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

```
<210> SEQ ID NO 12
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 12
```

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Asp

```
                20                  25                  30
Tyr Ile His Trp Val Gln Gln Ala Pro Gly Lys Gly Leu Glu Trp Met
            35                  40                  45

Gly Trp Ile Asp Pro Glu Asn Asn Asp Ser Glu Tyr Ser Ser Lys Phe
        50                  55                  60

Gln Gly Arg Val Thr Ile Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
                100                 105                 110

Ser Ser

<210> SEQ ID NO 13
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 13

Glu Val Gln Leu Val Gln Ser Gly Ala Glu Val Lys Lys Pro Gly Ala
 1               5                  10                  15

Thr Val Lys Ile Ser Cys Lys Ala Ser Gly Phe Asn Ile Tyr Asp Asp
                20                  25                  30

Tyr Ile His Trp Val Gln Gln Ala Pro Gly Lys Gly Leu Glu Trp Met
            35                  40                  45

Gly Trp Ile Asp Pro Glu Asn Asn Asp Ser Glu Tyr Ala Ser Lys Phe
        50                  55                  60

Gln Gly Arg Val Thr Ile Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
                100                 105                 110

Ser Ser

<210> SEQ ID NO 14
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 14

Glu Val Gln Leu Val Gln Ser Gly Ala Glu Val Lys Lys Pro Gly Ala
 1               5                  10                  15

Thr Val Lys Ile Ser Cys Lys Ala Ser Gly Phe Asn Ile Lys Asp Asp
                20                  25                  30

Tyr Ile His Trp Val Gln Gln Ala Pro Gly Lys Gly Leu Glu Trp Met
            35                  40                  45

Gly Trp Ile Asp Pro Glu Asn Asn Asp Ser Glu Tyr Ala Ser Lys Phe
        50                  55                  60

Gln Gly Arg Val Thr Ile Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                85                  90                  95
```

```
Thr Tyr Ala Phe Gly Gly Tyr Trp Gly Gln Gly Thr Thr Val Thr Val
                100                 105                 110

Ser Ser

<210> SEQ ID NO 15
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 15

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Asp
                20                  25                  30

Tyr Ile His Trp Val Gln Gln Ala Pro Gly Lys Gly Leu Glu Trp Met
            35                  40                  45

Gly Trp Ile Asp Pro Glu Asn Gly Asp Ser Glu Tyr Ala Ser Lys Phe
        50                  55                  60

Arg Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
                100                 105                 110

Ser Ser

<210> SEQ ID NO 16
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 16

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Asp
                20                  25                  30

Tyr Ile His Trp Val Gln Gln Ala Pro Gly Lys Gly Leu Glu Trp Met
            35                  40                  45

Gly Trp Ile Asp Pro Glu Asn Gly Asp Ser Glu Tyr Ser Ser Lys Phe
        50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
                100                 105                 110

Ser Ser

<210> SEQ ID NO 17
<211> LENGTH: 114
<212> TYPE: PRT
<213> ORGANISM: Artificial Sequence
<220> FEATURE:
<223> OTHER INFORMATION: Synthetic Sequence
```

-continued

<400> SEQUENCE: 17

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Pro Glu Asn Asn Asp Ser Glu Tyr Ser Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 18
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 18

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Tyr Asp Asp
            20                  25                  30

Tyr Ile His Trp Val Gln Gln Ala Pro Gly Lys Gly Leu Glu Trp Met
        35                  40                  45

Gly Trp Ile Asp Pro Glu Asn Asn Asp Ser Glu Tyr Ser Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 19
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 19

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Tyr Asp Asp
            20                  25                  30

Tyr Ile His Trp Val Gln Gln Ala Pro Gly Lys Gly Leu Glu Trp Met
        35                  40                  45

Gly Trp Ile Asp Pro Glu Asn Gly Asp Ser Glu Tyr Ser Ser Lys Phe

```
                    50                  55                  60
Gln Gly Arg Val Thr Ile Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                    85                  90                  95

Thr Tyr Ala Phe Gly Gly Tyr Trp Gly Gln Gly Thr Thr Val Thr Val
                100                 105                 110

Ser Ser

<210> SEQ ID NO 20
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 20

Glu Val Gln Leu Val Gln Ser Gly Ala Glu Val Lys Lys Pro Gly Ala
  1               5                  10                  15

Thr Val Lys Ile Ser Cys Lys Ala Ser Gly Phe Asn Ile Tyr Asp Asp
                 20                  25                  30

Tyr Ile His Trp Val Gln Gln Ala Pro Gly Lys Gly Leu Glu Trp Met
                 35                  40                  45

Gly Trp Ile Asp Pro Glu Asn Gly Asp Ser Tyr Ser Ser Lys Phe
                 50                  55                  60

Gln Gly Arg Val Thr Ile Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                    85                  90                  95

Thr Tyr Ala Phe Gly Gly Tyr Trp Gly Gln Gly Thr Thr Val Thr Val
                100                 105                 110

Ser Ser

<210> SEQ ID NO 21
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 21

Glu Val Gln Leu Val Gln Ser Gly Ala Glu Val Lys Lys Pro Gly Ala
  1               5                  10                  15

Thr Val Lys Ile Ser Cys Lys Ala Ser Gly Phe Ser Ile Lys Asp Asp
                 20                  25                  30

Tyr Ile His Trp Val Gln Gln Ala Pro Gly Lys Gly Leu Glu Trp Met
                 35                  40                  45

Gly Trp Ile Asp Pro Glu Asn Gly Asp Ser Tyr Ser Ser Lys Phe
                 50                  55                  60

Gln Gly Arg Val Thr Ile Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                    85                  90                  95

Thr Tyr Ala Phe Gly Gly Tyr Trp Gly Gln Gly Thr Thr Val Thr Val
                100                 105                 110

Ser Ser
```

<210> SEQ ID NO 22
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 22

```
Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Pro Glu Asn Asn Asp Ser Glu Tyr Ala Ser Lys Phe
    50                  55                  60

Arg Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser
```

<210> SEQ ID NO 23
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 23

```
Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Tyr Asp Asp
            20                  25                  30

Tyr Ile His Trp Val Gln Gln Ala Pro Gly Lys Gly Leu Glu Trp Met
        35                  40                  45

Gly Trp Ile Asp Pro Glu Asn Gly Asp Ser Glu Tyr Ala Ser Lys Phe
    50                  55                  60

Arg Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser
```

<210> SEQ ID NO 24
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 24

```
Glu Val Gln Leu Val Gln Ser Gly Ala Glu Val Lys Lys Pro Gly Ala
1               5                   10                  15
```

```
Thr Val Lys Ile Ser Cys Lys Ala Ser Gly Phe Asn Ile Tyr Asp Asp
            20                  25                  30

Tyr Ile His Trp Val Gln Gln Ala Pro Gly Lys Gly Leu Glu Trp Met
        35                  40                  45

Gly Trp Ile Asp Pro Glu Asn Asn Asp Ser Glu Tyr Ser Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 25
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 25

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Pro Glu Asn Asn Asp Ser Glu Tyr Ala Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 26
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 26

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Pro Glu Asn Gly Asp Ser Glu Tyr Ala Ser Lys Phe
    50                  55                  60

Arg Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
```

```
                    85                  90                  95

Thr Tyr Ala Phe Gly Gly Tyr Trp Gly Gln Gly Thr Thr Val Thr Val
                100                 105                 110

Ser Ser

<210> SEQ ID NO 27
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 27

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Lys Asp Asp
                20                  25                  30

Tyr Ile His Trp Val Gln Gln Ala Pro Gly Lys Gly Leu Glu Trp Met
            35                  40                  45

Gly Trp Ile Asp Pro Glu Asn Asn Asp Ser Glu Tyr Ser Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
                100                 105                 110

Ser Ser

<210> SEQ ID NO 28
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 28

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Tyr Asp Asp
                20                  25                  30

Tyr Ile His Trp Val Gln Gln Ala Pro Gly Lys Gly Leu Glu Trp Met
            35                  40                  45

Gly Trp Ile Asp Pro Glu Asn Asn Asp Ser Glu Tyr Ser Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
                100                 105                 110

Ser Ser

<210> SEQ ID NO 29
<211> LENGTH: 114
<212> TYPE: PRT
<213> ORGANISM: Artificial Sequence
<220> FEATURE:
```

<223> OTHER INFORMATION: Synthetic Sequence

<400> SEQUENCE: 29

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Ala Glu Asn Asn Asp Ser Glu Tyr Ser Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 30
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 30

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Tyr Asp Asp
            20                  25                  30

Tyr Ile His Trp Val Gln Gln Ala Pro Gly Lys Gly Leu Glu Trp Met
        35                  40                  45

Gly Trp Ile Asp Ala Glu Asn Asn Asp Ser Glu Tyr Ser Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 31
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 31

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Ala Glu Asn Asp Asp Ser Glu Tyr Ser Ser Lys Phe
            50                  55                  60

Gln Gly Arg Val Thr Ile Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Thr Tyr Ala Phe Gly Gly Tyr Trp Gly Gln Gly Thr Thr Val Thr Val
            100                 105                 110

Ser Ser

<210> SEQ ID NO 32
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 32

Glu Val Gln Leu Val Gln Ser Gly Ala Glu Val Lys Lys Pro Gly Ala
 1               5                  10                  15

Thr Val Lys Ile Ser Cys Lys Ala Ser Gly Phe Ser Ile Tyr Asp Asp
            20                  25                  30

Tyr Ile His Trp Val Gln Gln Ala Pro Gly Lys Gly Leu Glu Trp Met
            35                  40                  45

Gly Trp Ile Asp Ala Glu Asn Asp Asp Ser Glu Tyr Ser Ser Lys Phe
            50                  55                  60

Gln Gly Arg Val Thr Ile Thr Val Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Thr Tyr Ala Phe Gly Gly Tyr Trp Gly Gln Gly Thr Thr Val Thr Val
            100                 105                 110

Ser Ser

<210> SEQ ID NO 33
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 33

Glu Val Gln Leu Val Gln Ser Gly Ala Glu Val Lys Lys Pro Gly Ala
 1               5                  10                  15

Thr Val Lys Ile Ser Cys Lys Ala Ser Gly Phe Ser Ile Lys Asp Asp
            20                  25                  30

Tyr Ile His Trp Val Gln Gln Ala Pro Gly Lys Gly Leu Glu Trp Met
            35                  40                  45

Gly Trp Ile Asp Ala Glu Asn Asp Asp Ser Glu Tyr Ser Ser Lys Phe
            50                  55                  60

Gln Gly Arg Val Thr Ile Thr Val Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Thr Tyr Ala Phe Gly Gly Tyr Trp Gly Gln Gly Thr Thr Val Thr Val
            100                 105                 110

Ser Ser

<210> SEQ ID NO 34
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 34

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Tyr Asp Asp
            20                  25                  30

Tyr Ile His Trp Val Gln Gln Ala Pro Gly Lys Gly Leu Glu Trp Met
        35                  40                  45

Gly Trp Ile Asp Ala Glu Asn Asp Asp Ser Glu Tyr Ser Ser Lys Phe
    50                  55                  60

Gln Gly Arg Val Thr Ile Thr Val Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 35
<211> LENGTH: 117
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (10)..(10)
<223> OTHER INFORMATION: Xaa1 is arginine (Arg) or glycine (Gly)
<220> FEATURE:
<221> NAME/KEY: MISC_FEATURE
<222> LOCATION: (21)..(21)
<223> OTHER INFORMATION: Xaa2 is threonine (Thr) or isoleucine (Ile)
<220> FEATURE:
<221> NAME/KEY: MISC_FEATURE
<222> LOCATION: (23)..(23)
<223> OTHER INFORMATION: Xaa3 is threonine (Thr) or alanine (Ala)
<220> FEATURE:
<221> NAME/KEY: MISC_FEATURE
<222> LOCATION: (28)..(28)
<223> OTHER INFORMATION: Xaa4 is serine (Ser) or phenylalanine (Phe)
<220> FEATURE:
<221> NAME/KEY: MISC_FEATURE
<222> LOCATION: (30)..(30)
<223> OTHER INFORMATION: Xaa5 is serine (Ser) or phenylalanine (Phe)
<220> FEATURE:
<221> NAME/KEY: MISC_FEATURE
<222> LOCATION: (35)..(35)
<223> OTHER INFORMATION: Xaa6 is serine (Ser) or isoleucine (Ile)
<220> FEATURE:
<221> NAME/KEY: MISC_FEATURE
<222> LOCATION: (42)..(42)
<223> OTHER INFORMATION: Xaa7 is glycine (Gly) or arginine (Arg)
<220> FEATURE:
<221> NAME/KEY: MISC_FEATURE
<222> LOCATION: (56)..(56)
<223> OTHER INFORMATION: Xaa8 is serine (Ser) or asparagine (Asn)
<220> FEATURE:
<221> NAME/KEY: MISC_FEATURE
<222> LOCATION: (78)..(78)
<223> OTHER INFORMATION: Xaa9 is phenylalanine (Phe) or leucine (Leu)
<220> FEATURE:
<221> NAME/KEY: MISC_FEATURE

```
<222> LOCATION: (83)..(83)
<223> OTHER INFORMATION: Xaa10 is asparagine (Asn) or serine (Ser)
<220> FEATURE:
<221> NAME/KEY: MISC_FEATURE
<222> LOCATION: (84)..(84)
<223> OTHER INFORMATION: Xaa11 is serine (Ser) or phenylalanine (Phe)
<220> FEATURE:
<221> NAME/KEY: MISC_FEATURE
<222> LOCATION: (96)..(96)
<223> OTHER INFORMATION: Xaa12 is alanine (Ala) or valine (Val)
<220> FEATURE:
<221> NAME/KEY: MISC_FEATURE
<222> LOCATION: (100)..(100)
<223> OTHER INFORMATION: Xaa13 is aspartic acid (Asp) or asparagine
      (Asn)

<400> SEQUENCE: 35

Gln Val Gln Leu Gln Gln Trp Gly Ala Xaa Leu Leu Lys Pro Ser Glu
1               5                   10                  15

Thr Leu Ser Leu Xaa Cys Xaa Val Tyr Gly Gly Xaa Phe Xaa Gly Tyr
            20                  25                  30

Tyr Trp Xaa Trp Ile Arg Gln Pro Pro Xaa Lys Gly Leu Glu Trp Ile
        35                  40                  45

Gly Glu Ile Asn His Ser Gly Xaa Thr Asn Tyr Asn Pro Ser Leu Lys
50                  55                  60

Ser Arg Val Thr Ile Ser Val Asp Thr Ser Lys Asn Gln Xaa Ser Leu
65                  70                  75                  80

Lys Leu Xaa Xaa Val Thr Ala Ala Asp Thr Ala Val Tyr Tyr Cys Xaa
            85                  90                  95

Arg Glu Gly Xaa Tyr Gly Asp Tyr Asp Tyr Trp Gly Gln Gly Thr Leu
            100                 105                 110

Val Thr Val Ser Ser
        115

<210> SEQ ID NO 36
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 36

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 37
<211> LENGTH: 117
```

```
<212> TYPE: PRT
<213> ORGANISM: Artificial Sequence
<220> FEATURE:
<223> OTHER INFORMATION: Synthetic Sequence

<400> SEQUENCE: 37

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 38
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 38

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 39
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 39

Gln Val Gln Leu Gln Gln Trp Gly Ala Arg Leu Leu Lys Pro Ser Glu
1               5                   10                  15

Thr Leu Ser Leu Thr Cys Ala Val Tyr Gly Gly Ser Phe Ser Gly Tyr
```

```
                    20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 40
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 40

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asn His Ser Gly Asn Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 41

Gln Val Gln Leu Gln Gln Trp Gly Ala Gly Leu Leu Lys Pro Ser Glu
1               5                   10                  15

Thr Leu Ser Leu Ile Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asn His Ser Gly Asn Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80
```

```
Lys Leu Ser Ser Val Thr Ala Ala Asp Thr Ala Val Tyr Tyr Cys Val
                 85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 42
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 42

Gln Val Gln Leu Gln Gln Trp Gly Ala Arg Leu Leu Lys Pro Ser Glu
1               5                   10                  15

Thr Leu Ser Leu Ile Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                 85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 43
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 43

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                 85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 44
```

```
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 44

Gln Val Gln Leu Gln Gln Trp Gly Ala Arg Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Arg Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 45
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 45

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Phe Val Thr Ala Ala Asp Thr Ala Val Tyr Tyr Cys Val
                85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 46
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 46

Gln Val Gln Leu Gln Gln Trp Gly Ala Arg Leu Leu Lys Pro Ser Glu
1               5                   10                  15
```

```
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Phe Val Thr Ala Ala Asp Thr Ala Val Tyr Tyr Cys Val
                85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 47
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 47

Gln Val Gln Leu Gln Gln Trp Gly Ala Arg Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 48
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 48

Gln Val Gln Leu Gln Gln Trp Gly Ala Gly Leu Leu Lys Pro Ser Glu
1               5                   10                  15

Thr Leu Ser Leu Thr Cys Thr Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80
```

Lys Leu Asn Ser Val Thr Ala Ala Asp Thr Ala Val Tyr Tyr Cys Ala
                85                  90                  95

Arg Glu Gly Asp Tyr Gly Asp Tyr Asp Tyr Trp Gly Gln Gly Thr Leu
            100                 105                 110

Val Thr Val Ser Ser
            115

<210> SEQ ID NO 49
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 49

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Leu Ser Leu
65                  70                  75                  80

Lys Leu Asn Ser Val Thr Ala Ala Asp Thr Ala Val Tyr Tyr Cys Ala
                85                  90                  95

Arg Glu Gly Asp Tyr Gly Asp Tyr Asp Tyr Trp Gly Gln Gly Thr Leu
            100                 105                 110

Val Thr Val Ser Ser
            115

<210> SEQ ID NO 50
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 50

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Phe Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Glu Gly Asp Tyr Gly Asp Tyr Asp Tyr Trp Gly Gln Gly Thr Leu
            100                 105                 110

Val Thr Val Ser Ser
            115

<210> SEQ ID NO 51
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 51

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Glu Gly Asn Tyr Gly Asp Tyr Asp Tyr Trp Gly Gln Gly Thr Leu
            100                 105                 110

Val Thr Val Ser Ser
        115
```

<210> SEQ ID NO 52
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 52

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
            20                  25                  30

Tyr Trp Ile Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Glu Gly Asp Tyr Gly Asp Tyr Asp Tyr Trp Gly Gln Gly Thr Leu
            100                 105                 110

Val Thr Val Ser Ser
        115
```

<210> SEQ ID NO 53
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 53

```
Gln Val Gln Leu Gln Gln Trp Gly Ala Gly Leu Leu Lys Pro Ser Glu
 1               5                  10                  15
```

```
Thr Leu Ser Leu Thr Cys Ala Val Tyr Gly Gly Ser Phe Ser Gly Tyr
            20                  25                  30

Tyr Trp Ile Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Val
                85                  90                  95

Arg Glu Gly Asp Tyr Gly Asp Tyr Asp Tyr Trp Gly Gln Gly Thr Leu
            100                 105                 110

Val Thr Val Ser Ser
        115

<210> SEQ ID NO 54
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 54

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Phe Gly Tyr
            20                  25                  30

Tyr Trp Ile Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Val
                85                  90                  95

Arg Glu Gly Asn Tyr Gly Asp Tyr Asp Tyr Trp Gly Gln Gly Thr Leu
            100                 105                 110

Val Thr Val Ser Ser
        115

<210> SEQ ID NO 55
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 55

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Phe Gly Tyr
            20                  25                  30

Tyr Trp Ile Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
```

```
                65                  70                  75                  80
Lys Leu Asn Ser Val Thr Ala Ala Asp Thr Ala Val Tyr Tyr Cys Val
                    85                  90                  95

Arg Glu Gly Asp Tyr Gly Asp Tyr Asp Tyr Trp Gly Gln Gly Thr Leu
                100                 105                 110

Val Thr Val Ser Ser
        115

<210> SEQ ID NO 56
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 56

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Val
                    85                  90                  95

Arg Glu Gly Asn Tyr Gly Asp Tyr Asp Tyr Trp Gly Gln Gly Thr Leu
                100                 105                 110

Val Thr Val Ser Ser
        115

<210> SEQ ID NO 57
<211> LENGTH: 114
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (2)..(2)
<223> OTHER INFORMATION: Xaa1 is valine (Val) or isoleucine (Ile)
<220> FEATURE:
<221> NAME/KEY: MISC_FEATURE
<222> LOCATION: (25)..(25)
<223> OTHER INFORMATION: Xaa2 is cysteine (Cys) or serine (Ser)
<220> FEATURE:
<221> NAME/KEY: MISC_FEATURE
<222> LOCATION: (34)..(34)
<223> OTHER INFORMATION: Xaa3 is glycine (Gly) or serine (Ser)
<220> FEATURE:
<221> NAME/KEY: MISC_FEATURE
<222> LOCATION: (35)..(35)
<223> OTHER INFORMATION: Xaa4 is asparagine (Asn) or aspartic acid (Asp)
<220> FEATURE:
<221> NAME/KEY: MISC_FEATURE
<222> LOCATION: (55)..(55)
<223> OTHER INFORMATION: Xaa5 is lysine (Lys), glycine (Gly), asparagine
      (Asn), serine (Ser), or leucine (Leu)
<220> FEATURE:
<221> NAME/KEY: MISC_FEATURE
<222> LOCATION: (56)..(56)
<223> OTHER INFORMATION: Xaa6 is valine (Val) or isoleucine (Ile)
<220> FEATURE:
<221> NAME/KEY: MISC_FEATURE
```

```
<222> LOCATION: (94)..(94)
<223> OTHER INFORMATION: Xaa7 is serine (Ser), alanine (Ala), or glycine
      (Gly)
<220> FEATURE:
<221> NAME/KEY: MISC_FEATURE
<222> LOCATION: (98)..(98)
<223> OTHER INFORMATION: Xaa8 is histidine (His) or tyrosine (Tyr)

<400> SEQUENCE: 57

Asp Xaa Val Met Thr Gln Thr Pro Leu Ser Leu Ser Val Thr Pro Gly
1               5                   10                  15

Gln Pro Ala Ser Ile Ser Cys Arg Xaa Ser Gln Ser Leu Val His Ser
            20                  25                  30

Asp Xaa Xaa Thr Tyr Leu His Trp Tyr Leu Gln Lys Pro Gly Gln Ser
        35                  40                  45

Pro Gln Leu Leu Ile Tyr Xaa Xaa Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Xaa Gln Ser
                85                  90                  95

Thr Xaa Val Pro Tyr Ala Phe Gly Gly Gly Thr Lys Val Glu Ile Lys
            100                 105                 110

Arg Thr

<210> SEQ ID NO 58
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 58

Asp Val Val Met Thr Gln Thr Pro Leu Ser Leu Ser Val Thr Pro Gly
1               5                   10                  15

Gln Pro Ala Ser Ile Ser Cys Arg Cys Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 59
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 59

Asp Val Val Met Thr Gln Thr Pro Leu Ser Leu Ser Val Thr Pro Gly
1               5                   10                  15
```

```
Gln Pro Ala Ser Ile Ser Cys Arg Cys Ser Gln Ser Leu Val His Ser
                20                  25                  30

Asp Ser Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 60
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 60

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
                20                  25                  30

Asp Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 61
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 61

Asp Val Val Met Thr Gln Thr Pro Leu Ser Leu Ser Val Thr Pro Gly
1               5                   10                  15

Gln Pro Ala Ser Ile Ser Cys Arg Cys Ser Gln Ser Leu Val His Ser
                20                  25                  30

Asp Gly Asn Thr Tyr Leu His Trp Tyr Leu Gln Lys Pro Gly Gln Ser
            35                  40                  45

Pro Gln Leu Leu Ile Tyr Gly Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
```

-continued

```
                85                  90                  95
Thr His Val Pro Tyr Ala Phe Gly Gly Gly Thr Lys Val Glu Ile Lys
            100                 105                 110

Arg Thr

<210> SEQ ID NO 62
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 62

Asp Val Val Met Thr Gln Thr Pro Leu Ser Leu Ser Val Thr Pro Gly
1               5                   10                  15

Gln Pro Ala Ser Ile Ser Cys Arg Cys Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Asn Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 63
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 63

Asp Val Val Met Thr Gln Thr Pro Leu Ser Leu Ser Val Thr Pro Gly
1               5                   10                  15

Gln Pro Ala Ser Ile Ser Cys Arg Cys Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Ser Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 64
<211> LENGTH: 114
<212> TYPE: PRT
<213> ORGANISM: Artificial Sequence
<220> FEATURE:
```

<223> OTHER INFORMATION: Synthetic Sequence

<400> SEQUENCE: 64

Asp Val Val Met Thr Gln Thr Pro Leu Ser Leu Ser Val Thr Pro Gly
1               5                   10                  15

Gln Pro Ala Ser Ile Ser Cys Arg Cys Ser Gln Ser Leu Val His Ser
            20                  25                  30

Asp Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 65
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 65

Asp Val Val Met Thr Gln Thr Pro Leu Ser Leu Ser Val Thr Pro Gly
1               5                   10                  15

Gln Pro Ala Ser Ile Ser Cys Arg Cys Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ala Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 66
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 66

Asp Val Val Met Thr Gln Thr Pro Leu Ser Leu Ser Val Thr Pro Gly
1               5                   10                  15

Gln Pro Ala Ser Ile Ser Cys Arg Cys Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gly Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 67
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 67

Asp Val Val Met Thr Gln Thr Pro Leu Ser Leu Ser Val Thr Pro Gly
1               5                   10                  15

Gln Pro Ala Ser Ile Ser Cys Arg Cys Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr Tyr Val Pro Tyr Ala Phe Gly Gly Gly Thr Lys Val Glu Ile Lys
            100                 105                 110

Arg Thr

<210> SEQ ID NO 68
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 68

Asp Val Val Met Thr Gln Thr Pro Leu Ser Leu Ser Val Thr Pro Gly
1               5                   10                  15

Gln Pro Ala Ser Ile Ser Cys Arg Cys Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 69
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 69

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Ser Asn Thr Tyr Leu His Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gly Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 70
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 70

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Ser Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gly Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 71
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 71

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gly Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 72
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 72

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Ser Asn Thr Tyr Leu His Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 73
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 73

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

-continued

```
Ser Arg Val Glu Ala Glu Asp Val Gly Val Tyr Phe Cys Gly Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 74
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 74

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Leu Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gly Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 75
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 75

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 76
<211> LENGTH: 114
<212> TYPE: PRT
<213> ORGANISM: Artificial Sequence
```

<220> FEATURE:
<223> OTHER INFORMATION: Synthetic Sequence

<400> SEQUENCE: 76

```
Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Ser Asn Thr Tyr Leu His Trp Tyr Leu Gln Lys Pro Gly Gln Ser
        35                  40                  45

Pro Gln Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Ala Phe Gly Gly Gly Thr Lys Val Glu Ile Lys
            100                 105                 110

Arg Thr
```

<210> SEQ ID NO 77
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 77

```
Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Ser Asn Thr Tyr Leu His Trp Tyr Leu Gln Lys Pro Gly Gln Ser
        35                  40                  45

Pro Gln Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gly Gln Ser
                85                  90                  95

Thr His Val Pro Tyr Ala Phe Gly Gly Gly Thr Lys Val Glu Ile Lys
            100                 105                 110

Arg Thr
```

<210> SEQ ID NO 78
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 78

```
Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45
```

```
Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                85                  90                  95

Thr Tyr Val Pro Tyr Ala Phe Gly Gly Gly Thr Lys Val Glu Ile Lys
                100                 105                 110

Arg Thr
```

<210> SEQ ID NO 79
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 79

```
Asp Val Val Met Thr Gln Thr Pro Leu Ser Leu Ser Val Thr Pro Gly
 1               5                   10                  15

Gln Pro Ala Ser Ile Ser Cys Arg Ser Ser Gln Ser Leu Val His Ser
                20                  25                  30

Asp Ser Asn Thr Tyr Leu His Trp Tyr Leu Gln Lys Pro Gly Gln Ser
                35                  40                  45

Pro Gln Leu Leu Ile Tyr Leu Ile Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Gly Gln Ser
                85                  90                  95

Thr His Val Pro Tyr Ala Phe Gly Gly Gly Thr Lys Val Glu Ile Lys
                100                 105                 110

Arg Thr
```

<210> SEQ ID NO 80
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 80

```
Asp Val Val Met Thr Gln Thr Pro Leu Ser Leu Ser Val Thr Pro Gly
 1               5                   10                  15

Gln Pro Ala Ser Ile Ser Cys Arg Ser Ser Gln Ser Leu Val His Ser
                20                  25                  30

Asp Ser Asn Thr Tyr Leu His Trp Tyr Leu Gln Lys Pro Gly Gln Ser
                35                  40                  45

Pro Gln Leu Leu Ile Tyr Leu Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Gly Gln Ser
                85                  90                  95

Thr Tyr Val Pro Tyr Ala Phe Gly Gly Gly Thr Lys Val Glu Ile Lys
                100                 105                 110
```

Arg Thr

<210> SEQ ID NO 81
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 81

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Ser Asn Thr Tyr Leu His Trp Tyr Leu Gln Lys Pro Gly Gln Ser
        35                  40                  45

Pro Gln Leu Leu Ile Tyr Leu Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gly Gln Ser
                85                  90                  95

Thr Tyr Val Pro Tyr Ala Phe Gly Gly Gly Thr Lys Val Glu Ile Lys
            100                 105                 110

Arg Thr

<210> SEQ ID NO 82
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 82

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Ser Asn Thr Tyr Leu His Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gly Gln Ser
                85                  90                  95

Thr Tyr Val Pro Tyr Ala Phe Gly Gly Gly Thr Lys Val Glu Ile Lys
            100                 105                 110

Arg Thr

<210> SEQ ID NO 83
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 83

Asp Val Val Met Thr Gln Thr Pro Leu Ser Leu Ser Val Thr Pro Gly

-continued

```
               1               5                  10                 15
            Gln Pro Ala Ser Ile Ser Cys Arg Ser Ser Gln Ser Leu Val His Ser
                        20                  25                 30

Asp Ser Asn Thr Tyr Leu His Trp Tyr Leu Gln Lys Pro Gly Gln Ser
                        35                  40                 45

Pro Gln Leu Leu Ile Tyr Leu Val Ser Asn Arg Phe Ser Gly Val Pro
                        50                  55                 60

Asp Arg Phe Ser Gly Ser Gly Ser Gly Thr Asp Phe Thr Leu Lys Ile
             65                 70                  75                 80

Ser Arg Val Glu Ala Glu Asp Val Gly Val Tyr Phe Cys Gly Gln Ser
                            85                  90                 95

Thr His Val Pro Tyr Ala Phe Gly Gly Gly Thr Lys Val Glu Ile Lys
                        100                 105                110

Arg Thr
```

<210> SEQ ID NO 84
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 84

```
            Asp Val Val Met Thr Gln Thr Pro Leu Ser Leu Ser Val Thr Pro Gly
             1               5                  10                 15

Gln Pro Ala Ser Ile Ser Cys Arg Ser Ser Gln Ser Leu Val His Ser
                        20                  25                 30

Asp Ser Asn Thr Tyr Leu His Trp Tyr Leu Gln Lys Pro Gly Gln Ser
                        35                  40                 45

Pro Gln Leu Leu Ile Tyr Lys Val Ser Asn Arg Phe Ser Gly Val Pro
                        50                  55                 60

Asp Arg Phe Ser Gly Ser Gly Ser Gly Thr Asp Phe Thr Leu Lys Ile
             65                 70                  75                 80

Ser Arg Val Glu Ala Glu Asp Val Gly Val Tyr Phe Cys Gly Gln Ser
                            85                  90                 95

Thr His Val Pro Tyr Ala Phe Gly Gly Gly Thr Lys Val Glu Ile Lys
                        100                 105                110

Arg Thr
```

<210> SEQ ID NO 85
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 85

```
            Asp Val Val Met Thr Gln Thr Pro Leu Ser Leu Ser Val Thr Pro Gly
             1               5                  10                 15

Gln Pro Ala Ser Ile Ser Cys Arg Ser Ser Gln Ser Leu Val His Ser
                        20                  25                 30

Asp Ser Asn Thr Tyr Leu His Trp Tyr Leu Gln Lys Pro Gly Gln Ser
                        35                  40                 45

Pro Gln Leu Leu Ile Tyr Leu Val Ser Asn Arg Phe Ser Gly Val Pro
                        50                  55                 60

Asp Arg Phe Ser Gly Ser Gly Ser Gly Thr Asp Phe Thr Leu Lys Ile
             65                 70                  75                 80
```

Ser Arg Val Glu Ala Glu Asp Val Gly Val Tyr Phe Cys Ser Gln Ser
            85                  90                  95

Thr His Val Pro Tyr Ala Phe Gly Gly Gly Thr Lys Val Glu Ile Lys
            100                 105                 110

Arg Thr

<210> SEQ ID NO 86
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 86

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Ser Asn Thr Tyr Leu His Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gly Gln Ser
            85                  90                  95

Thr His Val Pro Tyr Ala Phe Gly Gly Gly Thr Lys Val Glu Ile Lys
            100                 105                 110

Arg Thr

<210> SEQ ID NO 87
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 87

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Ser Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gly Gln Ser
            85                  90                  95

Thr His Val Pro Tyr Ala Phe Gly Gly Gly Thr Lys Val Glu Ile Lys
            100                 105                 110

Arg Thr

<210> SEQ ID NO 88
<211> LENGTH: 114
<212> TYPE: PRT

```
<213> ORGANISM: Artificial Sequence
<220> FEATURE:
<223> OTHER INFORMATION: Synthetic Sequence

<400> SEQUENCE: 88

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Ser Asn Thr Tyr Leu His Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Gly Gln Ser
                85                  90                  95

Thr His Val Pro Tyr Ala Phe Gly Gly Gly Thr Lys Val Glu Ile Lys
            100                 105                 110

Arg Thr

<210> SEQ ID NO 89
<211> LENGTH: 115
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (49)..(53)
<223> OTHER INFORMATION: the subsequence Xaa1 Xaa2 Xaa3 Xaa4 Xaa5 is
      deleted or is Tyr-Asp-Ala-Ser-Asn
<220> FEATURE:
<221> NAME/KEY: MISC_FEATURE
<222> LOCATION: (94)..(94)
<223> OTHER INFORMATION: Xaa6 is threonine (Thr) or isoleucine (Ile)

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Xaa Xaa Xaa Xaa Xaa Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Val Tyr Tyr Cys Gln Gln Ser Tyr Ser Xaa Leu Ile
                85                  90                  95

Thr Phe Gly Gln Gly Thr Arg Leu Glu Ile Lys Arg Thr Val Ala Ala
            100                 105                 110

Pro Ser Val
        115

<210> SEQ ID NO 90
<211> LENGTH: 115
<212> TYPE: PRT
<213> ORGANISM: Artificial Sequence
<220> FEATURE:
<223> OTHER INFORMATION: Synthetic Sequence
```

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Val Tyr Tyr Cys Gln Gln Ser Tyr Ser Thr Leu Ile
                85                  90                  95

Thr Phe Gly Gln Gly Thr Arg Leu Glu Ile Lys Arg Thr Val Ala Ala
            100                 105                 110

Pro Ser Val
        115

<210> SEQ ID NO 91
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Leu Glu Thr Gly Val Pro Ser Arg Phe Ser Gly Ser Gly Ser Gly Thr
    50                  55                  60

Asp Phe Thr Phe Thr Ile Ser Ser Leu Gln Pro Glu Asp Ile Ala Val
65                  70                  75                  80

Tyr Tyr Cys Gln Gln Ser Tyr Ser Thr Leu Ile Thr Phe Gly Gln Gly
                85                  90                  95

Thr Arg Leu Glu Ile Lys Arg Thr Val Ala Ala Pro Ser Val
            100                 105                 110

<210> SEQ ID NO 92
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Leu Glu Thr Gly Val Pro Ser Arg Phe Ser Gly Ser Gly Ser Gly Thr
    50                  55                  60

Asp Phe Thr Phe Thr Ile Ser Ser Leu Gln Pro Glu Asp Ile Ala Val
65                  70                  75                  80

Tyr Tyr Cys Gln Gln Ser Tyr Ser Ile Leu Ile Thr Phe Gly Gln Gly
            85                  90                  95

Thr Arg Leu Glu Ile Lys Arg Thr Val Ala Ala Pro Ser Val
            100                 105                 110

<210> SEQ ID NO 93
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 93
gaggtccagc tggtacagtc tggggctgag gtgaagaagc ctggggctac agtgaaaatc      60
tcctgcaagg cttctggatt taacattaaa gacgactata tacactgggt gaaacaggcc     120
cctggaaaag gcttgagtg gattggatgg attgatcctg agaatggtga tagtgaatat     180
gcctcgaagt tccagggcag agtcaccata accgtggaca cgtctacaaa cacagcctac     240
atggagctga gcagcctgag atctgaggac acggccgtgt attactgtac gtacgctttc     300 ggggggctact gggggcaagg gaccacggtc accgtctcct cagc                     344

<210> SEQ ID NO 94
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 94
gaggtccagc tggtacagtc tggggctgag gtgaagaagc ctggggctac agtgaaaatc      60
tcctgcaagg cttctggatt ttccattaaa gacgactata tacactgggt gaaacaggcc     120
cctggaaaag gcttgagtg gattggatgg attgatcctg agaatggtga tagtgaatat     180
gcctcgaagt tccagggcag agtcaccata accgtggaca cgtctacaaa cacagcctac     240
atggagctga gcagcctgag atctgaggac acggccgtgt attactgtac gtacgctttc     300 ggggggctact gggggcaagg gaccacggtc accgtctcct cagc                     344

<210> SEQ ID NO 95
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 95
gaggtccagc tggtacagtc tggggctgag gtgaagaagc ctggggctac agtgaaaatc      60
tcctgcaagg cttctggatt taacattaaa gacgactata tacactgggt gaaacaggcc     120
cctggaaaag gcttgagtg gattggatgg attgatcctg agaataacga tagtgaatat     180
gcctcgaagt tccagggcag agtcaccata accgtggaca cgtctacaaa cacagcctac     240
atggagctga gcagcctgag atctgaggac acggccgtgt attactgtac gtacgctttc     300 ggggggctact gggggcaagg gaccacggtc accgtctcct cagc                     344

<210> SEQ ID NO 96
<211> LENGTH: 344

```
<212> TYPE: DNA
<213> ORGANISM: Artificial Sequence
<220> FEATURE:
<223> OTHER INFORMATION: Synthetic Sequence

<400> SEQUENCE: 96
gaggtccagc tggtacagtc tggggctgag gtgaagaagc ctggggctac agtgaaaatc    60
tcctgcaagg cttctggatt aacattaaa gacgactata tacactgggt gaaacaggcc   120
cctgaaaaag ggcttgagtg gattggatgg attgatcctg agaatggtga tagtgaatat   180
tcctcgaagt tccagggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344

<210> SEQ ID NO 97
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 97
gaggtccagc tggtacagtc tggggctgag gtgaagaagc ctggggctac agtgaaaatc    60
tcctgcaagg cttctggatt aacattaaa gacgactata tacactgggt gcagcaggcc   120
cctggaaaag ggcttgagtg gatgggatgg attgatcctg agaatggtga tagtgaatat   180
gcctcgaagt tccagggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344

<210> SEQ ID NO 98
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 98
gaggtccagc tggtacagtc tggggctgag gtgaagaagc ctggggctac agtgaaaatc    60
tcctgcaagg cttctggatt aacattaaa gacgactata tacactgggt gaaacaggcc   120
cctggaaaag ggcttgagtg gattggatgg attgatcctg agaatgacga tagtgaatat   180
gcctcgaagt tccagggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344

<210> SEQ ID NO 99
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 99
gaggtccagc tggtacagtc tggggctgag gtgaagaagc ctggggctac agtgaaaatc    60
tcctgcaagg cttctggatt aacatttat gacgactata tacactgggt gcagcaggcc   120
cctggaaaag ggcttgagtg gatgggatgg attgatcctg agaatggtga tagtgaatat   180
```

```
gcctcgaagt tccagggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                      344
```

<210> SEQ ID NO 100
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 100

```
gaggtccagc tggtacagtc tggggctgag gtgaagaagc ctggggctac agtgaaaatc    60
tcctgcaagg cttctggatt ttccattaaa gacgactata tacactgggt gcagcaggcc    120
cctggaaaag ggcttgagtg gatgggatgg attgatcctg agaatggtga tagtgaatat    180
gcctcgaagt tccagggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                      344
```

<210> SEQ ID NO 101
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 101

```
gaggtccagc tggtacagtc tggggctgag gtgaagaagc ctggggctac agtgaaaatc    60
tcctgcaagg cttctggatt ttccattaat gacgactata tacactgggt gcagcaggcc    120
cctggaaaag ggcttgagtg gatgggatgg attgatcctg agaatggtga tagtgaatat    180
gcctcgaagt tccagggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                      344
```

<210> SEQ ID NO 102
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 102

```
gaggtccagc tggtacagtc tggggctgag gtgaagaagc ctggggctac agtgaaaatc    60
tcctgcaagg cttctggatt ttccattaat gacgactata tacactgggt gcagcaggcc    120
cctggaaaag ggcttgagtg gatgggatgg attgatcctg agaatggtga tagtgaatat    180
gcctcgaagt tccagggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                      344
```

<210> SEQ ID NO 103
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 103

```
gaggtccagc tggtacagtc tggggctgag gtgaagaagc ctggggctac agtgaaaatc    60
tcctgcaagg cttctggatt aacattaaa gacgactata tacactgggt gcagcaggcc   120
cctggaaaag ggcttgagtg gatgggatgg attgatcctg agaataatga tagtgaatat   180
tcctcgaagt tccagggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344
```

<210> SEQ ID NO 104
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 104

```
gaggtccagc tggtacagtc tggggctgag gtgaagaagc ctggggctac agtgaaaatc    60
tcctgcaagg cttctggatt aacattat gacgactata tacactgggt gcagcaggcc   120
cctggaaaag ggcttgagtg gatgggatgg attgatcctg agaataatga tagtgaatat   180
gcctcgaagt tccagggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344
```

<210> SEQ ID NO 105
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 105

```
gaggtccagc tggtacagtc tggggctgag gtgaagaagc ctggggctac agtgaaaatc    60
tcctgcaagg cttctggatt aacattaaa gacgactata tacactgggt gcagcaggcc   120
cctggaaaag ggcttgagtg gatgggatgg attgatcctg agaataatga tagtgaatat   180
gcctcgaagt tccagggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344
```

<210> SEQ ID NO 106
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 106

```
gaggtccagc tggtacagtc tggggctgag gtgaagaagc ctggggctac agtgaaaatc    60
tcctgcaagg cttctggatt aacattaaa gacgactata tacactgggt gcagcaggcc   120
cctggaaaag ggcttgagtg gatgggatgg attgatcctg agaatggtga tagtgaatat   180
gcctcgaagt tccggggcag agtcaccata accgtggaca cgtctacaaa cacagcctac   240
atggagctga gcagcctgag atctgaggac acggccgtgt attactgtac gtacgctttc   300
```

```
gggggctact gggggcaagg gaccacggtc accgtctcct cagc              344
```

<210> SEQ ID NO 107
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 107

```
gaggtccagc tggtacagtc tggggctgag gtgaagaagc ctggggctac agtgaaaatc    60
tcctgcaagg cttctggatt taacattaaa gacgactata tacactgggt gcagcaggcc   120
cctggaaaag gcttgagtg gatgggatgg attgatcctg agaatggtga tagtgaatat   180
tcctcgaagt tccagggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344
```

<210> SEQ ID NO 108
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 108

```
gaggtccagc tggtacagtc tggggctgag gtgaagaagc ctggggctac agtgaaaatc    60
tcctgcaagg cttctggatt taacattaaa gacgactata tacactgggt gcagcaggcc   120
cctggaaaag gcttgagtg gatgggatgg attgatcctg agaataatga tagtgaatat   180
tcctcgaagt tccggggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344
```

<210> SEQ ID NO 109
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 109

```
gaggtccagc tggtacagtc tggggctgag gtgaagaagc ctggggctac agtgaaaatc    60
tcctgcaagg cttctggatt ttccatttat gacgactata tacactgggt gcagcaggcc   120
cctggaaaag gcttgagtg gatgggatgg attgatcctg agaataatga tagtgaatat   180
tcctcgaagt tccggggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344
```

<210> SEQ ID NO 110
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 110

```
gaggtccagc tggtacagtc tggggctgag gtgaagaagc ctggggctac agtgaaaatc    60
```
tcctgcaagg cttctggatt ttccatttat gacgactata tacactgggt gcagcaggcc    120
cctggaaaag ggcttgagtg gatgggatgg attgatcctg agaatggtga tagtgaatat    180
tcctcgaagt tccagggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                     344

<210> SEQ ID NO 111
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 111
gaggtccagc tggtacagtc tggggctgag gtgaagaagc ctggggctac agtgaaaatc     60
tcctgcaagg cttctggatt taacatttat gacgactata tacactgggt gcagcaggcc    120
cctggaaaag ggcttgagtg gatgggatgg attgatcctg agaatggtga tagtgaatat    180
tcctcgaagt tccagggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                     344

<210> SEQ ID NO 112
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 112
gaggtccagc tggtacagtc tggggctgag gtgaagaagc ctggggctac agtgaaaatc     60
tcctgcaagg cttctggatt ttccattaaa gacgactata tacactgggt gcagcaggcc    120
cctggaaaag ggcttgagtg gatgggatgg attgatcctg agaatggtga tagtgaatat    180
tcctcgaagt tccagggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                     344

<210> SEQ ID NO 113
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 113
gaggtccagc tggtacagtc tggggctgag gtgaagaagc ctggggctac agtgaaaatc     60
tcctgcaagg cttctggatt taacattaaa gacgactata tacactgggt gcagcaggcc    120
cctggaaaag ggcttgagtg gatgggatgg attgatcctg agaataatga tagtgaatat    180
gcctcgaagt tccggggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                     344

<210> SEQ ID NO 114

<211> LENGTH: 344
<212> TYPE: DNA
<213> ORGANISM: Artificial Sequence
<220> FEATURE:
<223> OTHER INFORMATION: Synthetic Sequence

<400> SEQUENCE: 114

```
gaggtccagc tggtacagtc tggggctgag gtgaagaagc ctggggctac agtgaaaatc    60
tcctgcaagg cttctggatt ttccatttat gacgactata tacactgggt gcagcaggcc   120
cctggaaaag ggcttgagtg gatgggatgg attgatcctg agaatggtga tagtgaatat   180
gcctcgaagt tccggggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344
```

<210> SEQ ID NO 115
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 115

```
gaggtccagc tggtacagtc tggggctgag gtgaagaagc ctggggctac agtgaaaatc    60
tcctgcaagg cttctggatt taacatttat gacgactata tacactgggt gcagcaggcc   120
cctggaaaag ggcttgagtg gatgggatgg attgatcctg agaataatga tagtgaatat   180
tcctcgaagt tccagggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344
```

<210> SEQ ID NO 116
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 116

```
gaggtccagc tggtacagtc tggggctgag gtgaagaagc ctggggctac agtgaaaatc    60
tcctgcaagg cttctggatt ttccattaaa gacgactata tacactgggt gcagcaggcc   120
cctggaaaag ggcttgagtg gatgggatgg attgatcctg agaataatga tagtgaatat   180
gcctcgaagt tccagggcag agtcaccata accgtggaca cgtctacaaa cacagcctac   240
atggagctga gcagcctgag atctgaggac acggccgtgt attactgtac gtacgctttc   300
gggggctact gggggcaagg gaccacggtc accgtctcct cagc                    344
```

<210> SEQ ID NO 117
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 117

```
gaggtccagc tggtacagtc tggggctgag gtgaagaagc ctggggctac agtgaaaatc    60
tcctgcaagg cttctggatt ttccattaaa gacgactata tacactgggt gcagcaggcc   120
cctggaaaag ggcttgagtg gatgggatgg attgatcctg agaatggtga tagtgaatat   180
```

```
gcctcgaagt tccggggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                     344
```

<210> SEQ ID NO 118
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 118

```
gaggtccagc tggtacagtc tggggctgag gtgaagaagc ctggggctac agtgaaaatc    60
tcctgcaagg cttctggatt ttccattaaa gacgactata tacactgggt gcagcaggcc    120
cctggaaaag ggcttgagtg gatgggatgg attgatcctg agaataatga tagtgaatat    180
tcctcgaagt tccagggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                     344
```

<210> SEQ ID NO 119
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 119

```
gaggtccagc tggtacagtc tggggctgag gtgaagaagc ctggggctac agtgaaaatc    60
tcctgcaagg cttctggatt taacatttat gacgactata tacactgggt gcagcaggcc    120
cctggaaaag ggcttgagtg gatgggatgg attgatcctg agaataatga tagtgaatat    180
tcctcgaagt tccggggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                     344
```

<210> SEQ ID NO 120
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 120

```
gaggtccagc tggtacagtc tggggctgag gtgaagaagc ctggggctac agtgaaaatc    60
tcctgcaagg cttctggatt ttccattaaa gacgactata tacactgggt gcagcaggcc    120
cctggaaaag ggcttgagtg gatgggatgg attgatgccg agaataatga tagtgaatat    180
tcctcgaagt tccagggcag agtcaccata accgtggaca cgtctacaaa cacagcctac    240
atggagctga gcagcctgag atctgaggac acggccgtgt attactgtac gtacgctttc    300
gggggctact gggggcaagg gaccacggtc accgtctcct cagc                     344
```

<210> SEQ ID NO 121
<211> LENGTH: 344
<212> TYPE: DNA
<213> ORGANISM: Artificial Sequence
<220> FEATURE:

<223> OTHER INFORMATION: Synthetic Sequence

<400> SEQUENCE: 121

```
gaggtccagc tggtacagtc tggggctgag gtgaagaagc ctggggctac agtgaaaatc      60
tcctgcaagg cttctggatt ttccatttac gacgactata tacactgggt gcagcaggcc     120
cctggaaaag ggcttgagtg gatgggatgg attgatgccg agaataatga tagtgaatat     180
tcctcgaagt tccagggcag agtcaccata accgtggaca cgtctacaaa cacagcctac     240
atggagctga gcagcctgag atctgaggac acggccgtgt attactgtac gtacgctttc     300
gggggctact gggggcaagg gaccacggtc accgtctcct cagc                      344
```

<210> SEQ ID NO 122
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 122

```
gaggtccagc tggtacagtc tggggctgag gtgaagaagc ctggggctac agtgaaaatc      60
tcctgcaagg cttctggatt ttccattaaa gacgactata tacactgggt gcagcaggcc     120
cctggaaaag ggcttgagtg gatgggatgg attgatgccg agaatgatga tagtgaatat     180
tcctcgaagt tccagggcag agtcaccata accgtggaca cgtctacaaa cacagcctac     240
atggagctga gcagcctgag atctgaggac acggccgtgt attactgtac gtacgctttc     300
gggggctact gggggcaagg gaccacggtc accgtctcct cagc                      344
```

<210> SEQ ID NO 123
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 123

```
gaggtccagc tggtacagtc tggggctgag gtgaagaagc ctggggctac agtgaaaatc      60
tcctgcaagg cttctggatt ttccatttac gacgactata tacactgggt gcagcaggcc     120
cctggaaaag ggcttgagtg gatgggatgg attgatgccg agaatgatga tagtgaatat     180
tcctcgaagt tccagggcag agtcaccata accgtggaca cgtctacaaa cacagcctac     240
atggagctga gcagcctgag atctgaggac acggccgtgt attactgtac gtacgctttc     300
gggggctact gggggcaagg gaccacggtc accgtctcct cagc                      344
```

<210> SEQ ID NO 124
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 124

```
gaggtccagc tggtacagtc tggggctgag gtgaagaagc ctggggctac agtgaaaatc      60
tcctgcaagg cttctggatt ttccattaaa gacgactata tacactgggt gcagcaggcc     120
cctggaaaag ggcttgagtg gatgggatgg attgatgccg agaatgatga tagtgaatat     180
tcctcgaagt tccagggcag agtcaccata accgtggaca cgtctacaga cacagcctac     240
atggagctga gcagcctgag atctgaggac acggccgtgt attactgtac gtacgctttc     300
```

```
gggggctact gggggcaagg gaccacggtc accgtctcct cagc                   344

<210> SEQ ID NO 125
<211> LENGTH: 344
<212> TYPE: DNA
<213> ORGANISM: Artificial Sequence
<220> FEATURE:
<223> OTHER INFORMATION: Synthetic Sequence

<400> SEQUENCE: 125
gaggtccagc tggtacagtc tggggctgag gtgaagaagc ctggggctac agtgaaaatc    60
tcctgcaagg cttctggatt ttccatttac gacgactata tacactgggt gcagcaggcc   120
cctggaaaag ggcttgagtg gatgggatgg attgatgccg agaatgatga tagtgaatat   180
tcctcgaagt tccagggcag agtcaccata accgtggaca cgtctacaga cacagcctac   240
atggagctga gcagcctgag atctgaggac acggccgtgt attactgtac gtacgctttc   300
gggggctact gggggcaagg gaccacggtc accgtctcct cagc                    344

<210> SEQ ID NO 126
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 126
caggtgcagc tacaacagtg gggcgcagga ctgttgaagc cttcggagac cctgtccctg    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagtt ctgtgaccgc tgcggacacg gccgtgtatt actgtgcgag agaggggggac  300 tacggtgact acgactactg gggccaggga accctggtca ccgtctcctc agc          353

<210> SEQ ID NO 127
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 127
caggtgcagc tacaacagtg gggcgcagga ctgttgaagc cttcggagac cctgtccctg    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagtt ctgtgaccgc tgcggacacg gccgtgtatt actgtgtgag agaggggggac  300 tacggtgact acgactactg gggccaggga accctggtca ccgtctcctc agc          353

<210> SEQ ID NO 128
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 128
```

```
caggtgcagc tacaacagtg gggcgcagga ctgttgaagc cttcggagac cctgtccctg      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca agagtcgagt caccatatca gtagacacgt ccaagaacca gttctccctg     240
aagctgaatt ctgtgaccgc tgcggacacg gccgtgtatt actgtgcgag agagggggac     300
tacggtgact acgactactg gggccaggga accctggtca ccgtctcctc agc           353
```

<210> SEQ ID NO 129
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 129

```
caggtgcagc tacaacagtg gggcgcaaga ctgttgaagc cttcggagac cctgtccctg      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca agagtcgagt caccatatca gtagacacgt ccaagaacca gttctccctg     240
aagctgagtt ctgtgaccgc tgcggacacg gccgtgtatt actgtgtgag agaggggggac    300 tacggtgact acgactactg gggccaggga accctggtca ccgtctcctc agc           353
```

<210> SEQ ID NO 130
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 130

```
caggtgcagc tacaacagtg gggcgcagga ctgttgaagc cttcggagac cctgtccctg      60
acctgcgctg tctatggtgg gtccttcagt ggttactact ggagctggat ccgccagccc     120
ccagggaagg ggctggagtg gattggggaa atcaatcata gtggaaacac caactacaac     180
ccgtccctca agagtcgagt caccatatca gtagacacgt ccaagaacca gttctccctg     240
aagctgagtt ctgtgaccgc tgcggacacg gccgtgtatt actgtgtgag agaggggggac    300 tacggtgact acgactactg gggccaggga accctggtca ccgtctcctc agc           353
```

<210> SEQ ID NO 131
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 131

```
caggtgcagc tacaacagtg gggcgcagga ctgttgaagc cttcggagac cctgtccctg      60
atctgcgctg tctatggtgg gtccttcagt ggttactact ggagctggat ccgccagccc     120
ccagggaagg ggctggagtg gattggggaa atcaatcata gtggaaacac caactacaac     180
ccgtccctca agagtcgagt caccatatca gtagacacgt ccaagaacca gttctccctg     240
aagctgagtt ctgtgaccgc tgcggacacg gccgtgtatt actgtgtgag agaggggggac    300 tacggtgact acgactactg gggccaggga accctggtca ccgtctcctc agc           353
```

<210> SEQ ID NO 132
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 132

```
caggtgcagc tacaacagtg gggcgcaaga ctgttgaagc cttcggagac cctgtccctg      60
atctgcgctg tctatggtgg gtccttcagt ggttactact ggagctggat ccgccagccc     120
ccagggaagg ggctggagtg gattggggaa atcaatcata gtggaagcac caactacaac     180
ccgtccctca agagtcgagt caccatatca gtagacacgt ccaagaacca gttctccctg     240
aagctgagtt ctgtgaccgc tgcggacacg gccgtgtatt actgtgtgag agaggggac      300
tacggtgact acgactactg gggccaggga accctggtca ccgtctcctc agc           353
```

<210> SEQ ID NO 133
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 133

```
caggtgcagc tacaacagtg gggcgcagga ctgttgaagc cttcggagac cctgtccctg      60
acctgcgctg tctatggtgg gtccttcagt ggttactact ggagctggat ccgccagccc     120
ccacggaagg ggctggagtg gattggggaa atcaatcata gtggaaacac caactacaac     180
ccgtccctca agagtcgagt caccatatca gtagacacgt ccaagaacca gttctccctg     240
aagctgagtt ctgtgaccgc tgcggacacg gccgtgtatt actgtgtgag agaggggac      300
tacggtgact acgactactg gggccaggga accctggtca ccgtctcctc agc           353
```

<210> SEQ ID NO 134
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 134

```
caggtgcagc tacaacagtg gggcgcaaga ctgttgaagc cttcggagac cctgtccctg      60
acctgcgctg tctatggtgg gtccttcagt ggttactact ggagctggat ccgccagccc     120
ccacggaagg ggctggagtg gattggggaa atcaatcata gtggaagcac caactacaac     180
ccgtccctca agagtcgagt caccatatca gtagacacgt ccaagaacca gttctccctg     240
aagctgagtt ctgtgaccgc tgcggacacg gccgtgtatt actgtgtgag agaggggac      300
tacggtgact acgactactg gggccaggga accctggtca ccgtctcctc agc           353
```

<210> SEQ ID NO 135
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 135

```
caggtgcagc tacaacagtg gggcgcaaga ctgttgaagc cttcggagac cctgtccctg      60
acctgcgctg tctatggtgg gtccttcagt ggttactact ggagctggat ccgccagccc     120
```

| | |
|---|---|
| ccagggaagg ggctggagtg gattggggaa atcaatcata gtggaagcac caactacaac | 180 |
| ccgtccctca agagtcgagt caccatatca gtagacacgt ccaagaacca gttctccctg | 240 |
| aagctgagtt ttgtgaccgc tgcggacacg gccgtgtatt actgtgtgag agaggggac | 300 |
| tacggtgact acgactactg gggccaggga accctggtca ccgtctcctc agc | 353 |

<210> SEQ ID NO 136
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 136

| | |
|---|---|
| caggtgcagc tacaacagtg gggcgcagga ctgttgaagc cttcggagac cctgtccctg | 60 |
| acctgcgctg tctatggtgg gtccttcagt ggttactact ggagctggat ccgccagccc | 120 |
| ccagggaagg ggctggagtg gattggggaa atcaatcata gtggaaacac caactacaac | 180 |
| ccgtccctca agagtcgagt caccatatca gtagacacgt ccaagaacca gttctccctg | 240 |
| aagctgagtt ttgtgaccgc tgcggacacg gccgtgtatt actgtgtgag agaggggac | 300 |
| tacggtgact acgactactg gggccaggga accctggtca ccgtctcctc agc | 353 |

<210> SEQ ID NO 137
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 137

| | |
|---|---|
| caggtgcagc tacaacagtg gggcgcaaga ctgttgaagc cttcggagac cctgtccctg | 60 |
| acctgcgctg tctatggtgg gtccttcagt ggttactact ggagctggat ccgccagccc | 120 |
| ccagggaagg ggctggagtg gattggggaa atcaatcata gtggaaacac caactacaac | 180 |
| ccgtccctca agagtcgagt caccatatca gtagacacgt ccaagaacca gttctccctg | 240 |
| aagctgagtt ctgtgaccgc tgcggacacg gccgtgtatt actgtgtgag agaggggac | 300 |
| tacggtgact acgactactg gggccaggga accctggtca ccgtctcctc agc | 353 |

<210> SEQ ID NO 138
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 138

| | |
|---|---|
| caggtgcagc tacaacagtg gggcgcagga ctgttgaagc cttcggagac cctgtccctg | 60 |
| acctgcactg tctatggtgg gtccttcagt ggttactact ggagctggat ccgccagccc | 120 |
| ccagggaagg ggctggagtg gattggggaa atcaatcata gtggaagcac caactacaac | 180 |
| ccgtccctca agagtcgagt caccatatca gtagacacgt ccaagaacca gttctccctg | 240 |
| aagctgaatt ctgtgaccgc tgcggacacg gccgtgtatt actgtgcgag agaggggac | 300 |
| tacggtgact acgactactg gggccaggga accctggtca ccgtctcctc agc | 353 |

<210> SEQ ID NO 139
<211> LENGTH: 353
<212> TYPE: DNA
<213> ORGANISM: Artificial Sequence

```
<220> FEATURE:
<223> OTHER INFORMATION: Synthetic Sequence

<400> SEQUENCE: 139
caggtgcagc tacaacagtg gggcgcagga ctgttgaagc cttcggagac cctgtccctg    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagacacgt ccaagaacca gttgtccctg   240
aagctgaatt ctgtgaccgc tgcggacacg gccgtgtatt actgtgcgag agaggggac   300 tacggtgact acgactactg gggccaggga accctggtca ccgtctcctc agc          353

<210> SEQ ID NO 140
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 140
caggtgcagc tacaacagtg gggcgcagga ctgttgaagc cttcggagac cctgtccctg    60
acctgcgctg tctatggtgg gttcttcagt ggttactact ggagctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagtt ctgtgaccgc tgcggacacg gccgtgtatt actgtgtgag agaggggac   300 tacggtgact acgactactg gggccaggga accctggtca ccgtctcctc agc          353

<210> SEQ ID NO 141
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 141
caggtgcagc tacaacagtg gggcgcagga ctgttgaagc cttcggagac cctgtccctg    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagtt ctgtgaccgc tgcggacacg gccgtgtatt actgtgtgag agaggggaac   300
tacggtgact acgactactg gggccaggga accctggtca ccgtctcctc agc          353

<210> SEQ ID NO 142
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 142
caggtgcagc tacaacagtg gggcgcagga ctgttgaagc cttcggagac cctgtccctg    60
acctgcgctg tctatggtgg gtccttcagt ggttactact ggatctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
```

```
aagctgagtt ctgtgaccgc tgcggacacg ccgtgtatt actgtgtgag agagggggac    300
tacggtgact acgactactg gggccaggga accctggtca ccgtctcctc agc          353
```

<210> SEQ ID NO 143
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 143

```
caggtgcagc tacaacagtg gggcgcagga ctgttgaagc cttcggagac cctgtccctg    60
acctgcgctg tctatggtgg gtccttcagt ggttactact ggatctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgaatt ctgtgaccgc tgcggacacg ccgtgtatt actgtgtgag agagggggac   300
tacggtgact acgactactg gggccaggga accctggtca ccgtctcctc agc          353
```

<210> SEQ ID NO 144
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 144

```
caggtgcagc tacaacagtg gggcgcagga ctgttgaagc cttcggagac cctgtccctg    60
acctgcgctg tctatggtgg gttcttcagt ggttactact ggatctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgaatt ctgtgaccgc tgcggacacg ccgtgtatt actgtgtgag agaggggaac    300
tacggtgact acgactactg gggccaggga accctggtca ccgtctcctc agc          353
```

<210> SEQ ID NO 145
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 145

```
caggtgcagc tacaacagtg gggcgcagga ctgttgaagc cttcggagac cctgtccctg    60
acctgcgctg tctatggtgg gttcttcagt ggttactact ggatctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgaatt ctgtgaccgc tgcggacacg ccgtgtatt actgtgtgag agagggggac   300
tacggtgact acgactactg gggccaggga accctggtca ccgtctcctc agc          353
```

<210> SEQ ID NO 146
<211> LENGTH: 353
<212> TYPE: DNA
<213> ORGANISM: Artificial Sequence
<220> FEATURE:
<223> OTHER INFORMATION: Synthetic Sequence

<400> SEQUENCE: 146

```
caggtgcagc tacaacagtg gggcgcagga ctgttgaagc cttcggagac cctgtccctg    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgaatt ctgtgaccgc tgcggacacg ccgtgtatt actgtgtgag agaggggaac   300
tacggtgact acgactactg gggccaggga accctggtca ccgtctcctc agc          353
```

<210> SEQ ID NO 147
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 147

```
gatgtggtga tgacccagac tccactctct ctgtccgtca cccctggaca gccggcctcc    60
atctcctgca gatgtagtca gagccttgta cacagtgatg gaaacaccta tttacattgg   120
tacctgcaga agccaggcca gtctccacag ctcctgatct ataaagtttc caaccgattt   180
tctggagtgc cagataggtt cagtggcagc ggatcaggga cagatttcac actgaaaatc   240
agccgggtgg aggctgagga tgttggggtt tattttgct ctcaaagtac acatgttccg    300
tacgcgttcg gcggagggac caaggtggag atcaaacgga ct                      342
```

<210> SEQ ID NO 148
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 148

```
gatgtggtga tgacccagac tccactctct ctgtccgtca cccctggaca gccggcctcc    60
atctcctgca gatgtagtca gagccttgta cacagtgatt ctaacaccta tttacattgg   120
tacctgcaga agccaggcca gtctccacag ctcctgatct ataaagtttc caaccgattt   180
tctggagtgc cagataggtt cagtggcagc ggatcaggga cagatttcac actgaaaatc   240
agccgggtgg aggctgagga tgttggggtt tattttgct ctcaaagtac acatgttccg    300
tacgcgttcg gcggagggac caaggtggag atcaaacgga ct                      342
```

<210> SEQ ID NO 149
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 149

```
gatgtggtga tgacccagac tccactctct ctgtccgtca cccctggaca gccggcctcc    60
atctcctgca gaagtagtca gagccttgta cacagtgatg gaaacaccta tttacattgg   120
tacctgcaga agccaggcca gtctccacag ctcctgatct ataaagtttc caaccgattt   180
tctggagtgc cagataggtt cagtggcagc ggatcaggga cagatttcac actgaaaatc   240
agccgggtgg aggctgagga tgttggggtt tattttgct ctcaaagtac acatgttccg    300
tacgcgttcg gcggagggac caaggtggag atcaaacgga ct                      342
```

<210> SEQ ID NO 150
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 150

```
gatgtggtga tgacccagac tccactctct ctgtccgtca cccctggaca gccggcctcc    60
atctcctgca gatgtagtca gagccttgta cacagtgatg aaacaccta tttacattgg   120
tacctgcaga agccaggcca gtctccacag ctcctgatct atggagtttc aaccgattt    180
tctggagtgc cagataggtt cagtggcagc ggatcaggga cagatttcac actgaaaatc   240
agccgggtgg aggctgagga tgttgggggtt tattttttgct ctcaaagtac acatgttccg   300
tacgcgttcg gcggagggac caaggtggag atcaaacgga ct                      342
```

<210> SEQ ID NO 151
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 151

```
gatgtggtga tgacccagac tccactctct ctgtccgtca cccctggaca gccggcctcc    60
atctcctgca gatgtagtca gagccttgta cacagtgatg aaacaccta tttacattgg   120
tacctgcaga agccaggcca gtctccacag ctcctgatct ataacgtttc aaccgattt    180
tctggagtgc cagataggtt cagtggcagc ggatcaggga cagatttcac actgaaaatc   240
agccgggtgg aggctgagga tgttgggggtt tattttttgct ctcaaagtac acatgttccg   300
tacgcgttcg gcggagggac caaggtggag atcaaacgga ct                      342
```

<210> SEQ ID NO 152
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 152

```
gatgtggtga tgacccagac tccactctct ctgtccgtca cccctggaca gccggcctcc    60
atctcctgca gatgtagtca gagccttgta cacagtgatg aaacaccta tttacattgg   120
tacctgcaga agccaggcca gtctccacag ctcctgatct atagcgtttc aaccgattt    180
tctggagtgc cagataggtt cagtggcagc ggatcaggga cagatttcac actgaaaatc   240
agccgggtgg aggctgagga tgttgggggtt tattttttgct ctcaaagtac acatgttccg   300
tacgcgttcg gcggagggac caaggtggag atcaaacgga ct                      342
```

<210> SEQ ID NO 153
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 153

```
gatgtggtga tgacccagac tccactctct ctgtccgtca cccctggaca gccggcctcc    60
atctcctgca gatgtagtca gagccttgta cacagtgatg gagacaccta tttacattgg   120
```

```
tacctgcaga agccaggcca gtctccacag ctcctgatct ataaagtttc caaccgattt    180
tctggagtgc cagataggtt cagtggcagc ggatcaggga cagatttcac actgaaaatc    240
agccgggtgg aggctgagga tgttgggggtt tatttttgct ctcaaagtac acatgttccg   300
tacgcgttcg gcggagggac caaggtggag atcaaacgga ct                       342
```

<210> SEQ ID NO 154
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 154

```
gatgtggtga tgacccagac tccactctct ctgtccgtca cccctggaca gccggcctcc    60
atctcctgca gatgtagtca gagccttgta cacagtgatg aaacaccta tttacattgg    120 tacctgcaga agccaggcca gtctccacag ctcctgatct ataaagtttc caaccgattt    180
tctggagtgc cagataggtt cagtggcagc ggatcaggga cagatttcac actgaaaatc    240
agccgggtgg aggctgagga tgttgggggtt tatttttgcg cgcaaagtac acatgttccg    300
tacgcgttcg gcggagggac caaggtggag atcaaacgga ct                       342
```

<210> SEQ ID NO 155
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 155

```
gatgtggtga tgacccagac tccactctct ctgtccgtca cccctggaca gccggcctcc    60
atctcctgca gatgtagtca gagccttgta cacagtgatg aaacaccta tttacattgg    120 tacctgcaga agccaggcca gtctccacag ctcctgatct ataaagtttc caaccgattt    180
tctggagtgc cagataggtt cagtggcagc ggatcaggga cagatttcac actgaaaatc    240
agccgggtgg aggctgagga tgttgggggtt tatttttgcg gtcaaagtac acatgttccg    300
tacgcgttcg gcggagggac caaggtggag atcaaacgga ct                       342
```

<210> SEQ ID NO 156
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 156

```
gatgtggtga tgacccagac tccactctct ctgtccgtca cccctggaca gccggcctcc    60
atctcctgca gatgtagtca gagccttgta cacagtgatg aaacaccta tttacattgg    120 tacctgcaga agccaggcca gtctccacag ctcctgatct ataaagtttc caaccgattt    180
tctggagtgc cagataggtt cagtggcagc ggatcaggga cagatttcac actgaaaatc    240
agccgggtgg aggctgagga tgttgggggtt tatttttgct ctcaaagtac atatgttccg    300
tacgcgttcg gcggagggac caaggtggag atcaaacgga ct                       342
```

<210> SEQ ID NO 157
<211> LENGTH: 342
<212> TYPE: DNA

<213> ORGANISM: Artificial Sequence
<220> FEATURE:
<223> OTHER INFORMATION: Synthetic Sequence

<400> SEQUENCE: 157

```
gatgtggtga tgacccagac tccactctct ctgtccgtca cccctggaca gccggcctcc      60
atctcctgca gatgtagtca gagccttgta cacagtgatg gaaacaccta tttacattgg    120
tacctgcaga agccaggcca gtctccacag ctcctgatct ataaaatttc caaccgattt    180
tctggagtgc cagataggtt cagtggcagc ggatcaggga cagatttcac actgaaaatc    240
agccgggtgg aggctgagga tgttgggggtt tattttttgct ctcaaagtac acatgttccg    300
tacgcgttcg gcggagggac caaggtggag atcaaacgga ct                       342
```

<210> SEQ ID NO 158
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 158

```
gatgtggtga tgacccagac tccactctct ctgtccgtca cccctggaca gccggcctcc      60
atctcctgca gaagtagtca gagccttgta cacagtgatt caaacaccta tttacattgg    120
tacctgcaga agccaggcca gtctccacag ctcctgatct atctagtttc caaccgattt    180
tctggagtgc cagataggtt cagtggcagc ggatcaggga cagatttcac actgaaaatc    240
agccgggtgg aggctgagga tgttgggggtt tattttttgcg gtcaaagtac acatgttccg    300
tacgcgttcg gcggagggac caaggtggag atcaaacgga ct                       342
```

<210> SEQ ID NO 159
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 159

```
gatgtggtga tgacccagac tccactctct ctgtccgtca cccctggaca gccggcctcc      60
atctcctgca gaagtagtca gagccttgta cacagtgatt caaacaccta tttacattgg    120
tacctgcaga agccaggcca gtctccacag ctcctgatct ataaagtttc caaccgattt    180
tctggagtgc cagataggtt cagtggcagc ggatcaggga cagatttcac actgaaaatc    240
agccgggtgg aggctgagga tgttgggggtt tattttttgcg gtcaaagtac acatgttccg    300
tacgcgttcg gcggagggac caaggtggag atcaaacgga ct                       342
```

<210> SEQ ID NO 160
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 160

```
gatgtggtga tgacccagac tccactctct ctgtccgtca cccctggaca gccggcctcc      60
atctcctgca gaagtagtca gagccttgta cacagtgatg gaaacaccta tttacattgg    120
tacctgcaga agccaggcca gtctccacag ctcctgatct ataaagtttc caaccgattt    180
tctggagtgc cagataggtt cagtggcagc ggatcaggga cagatttcac actgaaaatc    240
```

```
agccgggtgg aggctgagga tgttggggtt tattttttgcg gtcaaagtac acatgttccg    300
tacgcgttcg gcggagggac caaggtggag atcaaacgga ct                        342
```

<210> SEQ ID NO 161
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 161

```
gatgtggtga tgacccagac tccactctct ctgtccgtca cccctggaca gccggcctcc    60
atctcctgca gaagtagtca gagccttgta cacagtgatt caaacaccta tttacattgg   120
tacctgcaga agccaggcca gtctccacag ctcctgatct atctagtttc caaccgattt   180
tctggagtgc cagataggtt cagtggcagc ggatcaggga cagatttcac actgaaaatc   240
agccgggtgg aggctgagga tgttggggtt tattttttgct ctcaaagtac acatgttccg   300
tacgcgttcg gcggagggac caaggtggag atcaaacgga ct                      342
```

<210> SEQ ID NO 162
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 162

```
gatgtggtga tgacccagac tccactctct ctgtccgtca cccctggaca gccggcctcc    60
atctcctgca gaagtagtca gagccttgta cacagtgatg aaacaccta tttacattgg    120 tacctgcaga agccaggcca gtctccacag ctcctgatct atctagtttc caaccgattt   180
tctggagtgc cagataggtt cagtggcagc ggatcaggga cagatttcac actgaaaatc   240
agccgggtgg aggctgagga tgttggggtt tattttttgcg gtcaaagtac acatgttccg   300
tacgcgttcg gcggagggac caaggtggag atcaaacgga ct                      342
```

<210> SEQ ID NO 163
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 163

```
gatgtggtga tgacccagac tccactctct ctgtccgtca cccctggaca gccggcctcc    60
atctcctgca gaagtagtca gagccttgta cacagtgatg aaacaccta tttacattgg    120 tacctgcaga agccaggcca gtctccacag ctcctgatct atctaatttc caaccgattt   180
tctggagtgc cagataggtt cagtggcagc ggatcaggga cagatttcac actgaaaatc   240
agccgggtgg aggctgagga tgttggggtt tattttttgct ctcaaagtac acatgttccg   300
tacgcgttcg gcggagggac caaggtggag atcaaacgga ct                      342
```

<210> SEQ ID NO 164
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 164

```
gatgtggtga tgacccagac tccactctct ctgtccgtca cccctggaca gccggcctcc    60
atctcctgca gaagtagtca gagccttgta cacagtgatg gaaacaccta tttacattgg   120
tacctgcaga agccaggcca gtctccacag ctcctgatct atctagtttc caaccgattt   180
tctggagtgc cagataggtt cagtggcagc ggatcaggga cagatttcac actgaaaatc   240
agccgggtgg aggctgagga tgttgggggtt tattttttgct ctcaaagtac acatgttccg   300
tacgcgttcg gcggagggac caaggtggag atcaaacgga ct                      342
```

<210> SEQ ID NO 165
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 165

```
gatgtggtga tgacccagac tccactctct ctgtccgtca cccctggaca gccggcctcc    60
atctcctgca gaagtagtca gagccttgta cacagtgatt caaacaccta tttacattgg   120
tacctgcaga agccaggcca gtctccacag ctcctgatct ataaaatttc caaccgattt   180
tctggagtgc cagataggtt cagtggcagc ggatcaggga cagatttcac actgaaaatc   240
agccgggtgg aggctgagga tgttgggggtt tattttttgct ctcaaagtac acatgttccg   300
tacgcgttcg gcggagggac caaggtggag atcaaacgga ct                      342
```

<210> SEQ ID NO 166
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 166

```
gatgtggtga tgacccagac tccactctct ctgtccgtca cccctggaca gccggcctcc    60
atctcctgca gaagtagtca gagccttgta cacagtgatt caaacaccta tttacattgg   120
tacctgcaga agccaggcca gtctccacag ctcctgatct ataaaatttc caaccgattt   180
tctggagtgc cagataggtt cagtggcagc ggatcaggga cagatttcac actgaaaatc   240
agccgggtgg aggctgagga tgttgggggtt tattttttgcg gtcaaagtac acatgttccg   300
tacgcgttcg gcggagggac caaggtggag atcaaacgga ct                      342
```

<210> SEQ ID NO 167
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 167

```
gatgtggtga tgacccagac tccactctct ctgtccgtca cccctggaca gccggcctcc    60
atctcctgca gaagtagtca gagccttgta cacagtgatg gaaacaccta tttacattgg   120
tacctgcaga agccaggcca gtctccacag ctcctgatct ataaagtttc caaccgattt   180
tctggagtgc cagataggtt cagtggcagc ggatcaggga cagatttcac actgaaaatc   240
agccgggtgg aggctgagga tgttgggggtt tattttttgct ctcaaagtac atatgttccg   300
tacgcgttcg gcggagggac caaggtggag atcaaacgga ct                      342
```

<210> SEQ ID NO 168
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 168

```
gatgtggtga tgacccagac tccactctct ctgtccgtca cccctggaca gccggcctcc      60
atctcctgca gaagtagtca gagccttgta cacagtgatt caaacaccta tttacattgg     120
tacctgcaga agccaggcca gtctccacag ctcctgatct atctaatttc caaccgattt     180
tctggagtgc cagataggtt cagtggcagc ggatcaggga cagatttcac actgaaaatc     240
agccgggtgg aggctgagga tgttggggtt tattttttgcg gtcaaagtac acatgttccg     300
tacgcgttcg gcggagggac caaggtggag atcaaacgga ct                        342
```

<210> SEQ ID NO 169
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 169

```
gatgtggtga tgacccagac tccactctct ctgtccgtca cccctggaca gccggcctcc      60
atctcctgca gaagtagtca gagccttgta cacagtgatt caaacaccta tttacattgg     120
tacctgcaga agccaggcca gtctccacag ctcctgatct atctagtttc caaccgattt     180
tctggagtgc cagataggtt cagtggcagc ggatcaggga cagatttcac actgaaaatc     240
agccgggtgg aggctgagga tgttggggtt tattttttgcg gtcaaagtac atatgttccg     300
tacgcgttcg gcggagggac caaggtggag atcaaacgga ct                        342
```

<210> SEQ ID NO 170
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 170

```
gatgtggtga tgacccagac tccactctct ctgtccgtca cccctggaca gccggcctcc      60
atctcctgca gaagtagtca gagccttgta cacagtgatt caaacaccta tttacattgg     120
tacctgcaga agccaggcca gtctccacag ctcctgatct atctaatttc caaccgattt     180
tctggagtgc cagataggtt cagtggcagc ggatcaggga cagatttcac actgaaaatc     240
agccgggtgg aggctgagga tgttggggtt tattttttgcg gtcaaagtac atatgttccg     300
tacgcgttcg gcggagggac caaggtggag atcaaacgga ct                        342
```

<210> SEQ ID NO 171
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 171

```
gatgtggtga tgacccagac tccactctct ctgtccgtca cccctggaca gccggcctcc      60
```

```
atctcctgca gaagtagtca gagccttgta cacagtgatg gaaacaccta tttacattgg    120
tacctgcaga agccaggcca gtctccacag ctcctgatct atctagtttc caaccgattt    180
tctggagtgc cagataggtt cagtggcagc ggatcaggga cagatttcac actgaaaatc    240
agccgggtgg aggctgagga tgttggggtt tattttttgcg gtcaaagtac atatgttccg    300
tacgcgttcg gcggagggac caaggtggag atcaaacgga ct                       342

<210> SEQ ID NO 172
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 172
gatgtggtga tgacccagac tccactctct ctgtccgtca cccctggaca gccggcctcc    60
atctcctgca gaagtagtca gagccttgta cacagtgatt caaacaccta tttacattgg    120
tacctgcaga agccaggcca gtctccacag ctcctgatct atctagtttc caaccgattt    180
tctggagtgc cagataggtt cagtggcagc ggatcaggga cagatttcac actgaaaatc    240
agccgggtgg aggctgagga tgttggggtt tattttttgcg gtcaaagtac acatgttccg    300
tacgcgttcg gcggagggac caaggtggag atcaaacgga ct                       342

<210> SEQ ID NO 173
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 173
gatgtggtga tgacccagac tccactctct ctgtccgtca cccctggaca gccggcctcc    60
atctcctgca gaagtagtca gagccttgta cacagtgatt caaacaccta tttacattgg    120
tacctgcaga agccaggcca gtctccacag ctcctgatct ataaagtttc caaccgattt    180
tctggagtgc cagataggtt cagtggcagc ggatcaggga cagatttcac actgaaaatc    240
agccgggtgg aggctgagga tgttggggtt tattttttgcg gtcaaagtac acatgttccg    300
tacgcgttcg gcggagggac caaggtggag atcaaacgga ct                       342

<210> SEQ ID NO 174
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 174
gatgtggtga tgacccagac tccactctct ctgtccgtca cccctggaca gccggcctcc    60
atctcctgca gaagtagtca gagccttgta cacagtgatt caaacaccta tttacattgg    120
tacctgcaga agccaggcca gtctccacag ctcctgatct atctagtttc caaccgattt    180
tctggagtgc cagataggtt cagtggcagc ggatcaggga cagatttcac actgaaaatc    240
agccgggtgg aggctgagga tgttggggtt tattttttgct ctcaaagtac acatgttccg    300
tacgcgttcg gcggagggac caaggtggag atcaaacgga ct                       342

<210> SEQ ID NO 175
<211> LENGTH: 342
```

<212> TYPE: DNA
<213> ORGANISM: Artificial Sequence
<220> FEATURE:
<223> OTHER INFORMATION: Synthetic Sequence

<400> SEQUENCE: 175

```
gatatcgtga tgacccagac tccactctct ctgtccgtca cccctggaca gccggcctcc      60
atctcctgca gaagtagtca gagccttgta cacagtgatt caaacaccta tttacattgg    120
tacctgcaga agccaggcca gtctccacag ctcctgatct atctagtttc caaccgattt    180
tctggagtgc cagataggtt cagtggcagc ggatcaggga cagatttcac actgaaaatc    240
agccgggtgg aggctgagga tgttgggggtt tattttttgcg gtcaaagtac acatgttccg   300
tacgcgttcg gcggagggac caaggtggag atcaaacgga ct                        342
```

<210> SEQ ID NO 176
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 176

```
gatatcgtga tgacccagac tccactctct ctgtccgtca cccctggaca gccggcctcc      60
atctcctgca gaagtagtca gagccttgta cacagtgatt caaacaccta tttacattgg    120
tacctgcaga agccaggcca gtctccacag ctcctgatct ataaagtttc caaccgattt    180
tctggagtgc cagataggtt cagtggcagc ggatcaggga cagatttcac actgaaaatc    240
agccgggtgg aggctgagga tgttgggggtt tattttttgcg gtcaaagtac acatgttccg   300
tacgcgttcg gcggagggac caaggtggag atcaaacgga ct                        342
```

<210> SEQ ID NO 177
<211> LENGTH: 342
<212> TYPE: DNA
<213> ORGANISM: Artificial Sequence
<220> FEATURE:
<223> OTHER INFORMATION: Synthetic Sequence

<400> SEQUENCE: 177

```
gatatcgtga tgacccagac tccactctct ctgtccgtca cccctggaca gccggcctcc      60
atctcctgca gaagtagtca gagccttgta cacagtgatt caaacaccta tttacattgg    120
tacctgcaga agccaggcca gtctccacag ctcctgatct atctagtttc caaccgattt    180
tctggagtgc cagataggtt cagtggcagc ggatcaggga cagatttcac actgaaaatc    240
agccgggtgg aggctgagga tgttgggggtt tattttttgct ctcaaagtac acatgttccg   300
tacgcgttcg gcggagggac caaggtggag atcaaacgga ct                        342
```

<210> SEQ ID NO 178
<211> LENGTH: 345
<212> TYPE: DNA
<213> ORGANISM: Artificial Sequence
<220> FEATURE:
<223> OTHER INFORMATION: Synthetic Sequence

<400> SEQUENCE: 178

```
gacatccaga tgacccagtc tccatcctcc ctgtctgcat ctgtaggaga cagagtcacc      60
atcacttgcc aggcgagtca ggacattagc aactatttaa attggtatca gcagaaacca    120
gggaaagccc ctaagctcct gatctacgat gcatccaatt tggaaacagg ggtcccatca    180
```

```
aggttcagtg aagtggatc tgggacagat tttactttca ccatcagcag cctgcagcct    240
gaagatattg cagtgtatta ctgtcaacag agttacagta ccctgatcac cttcggccaa    300
gggacacgac tggagattaa acgaactgtg gctgcaccat ctgtc                    345
```

<210> SEQ ID NO 179
<211> LENGTH: 330
<212> TYPE: DNA
<213> ORGANISM: Artificial Sequence
<220> FEATURE:
<223> OTHER INFORMATION: Synthetic Sequence

<400> SEQUENCE: 179

```
gacatccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagctcct gattttggaa acaggggtcc catcaaggtt cagtggaagt    180
ggatctggga cagattttac tttcaccatc agcagcctgc agcctgaaga tattgcagtg    240
tattactgtc aacagagtta cagtaccctg atcaccttcg gccaagggac acgactggag    300
attaaacgaa ctgtggctgc accatctgtc                                     330
```

<210> SEQ ID NO 180
<211> LENGTH: 330
<212> TYPE: DNA
<213> ORGANISM: Artificial Sequence
<220> FEATURE:
<223> OTHER INFORMATION: Synthetic Sequence

<400> SEQUENCE: 180

```
gacatccaga tgacccagtc tccatcctcc ctgtctgcat ctgtaggaga cagagtcacc     60
atcacttgcc aggcgagtca ggacattagc aactatttaa attggtatca gcagaaacca    120
gggaaagccc ctaagctcct gattttggaa acaggggtcc catcaaggtt cagtggaagt    180
ggatctggga cagattttac tttcaccatc agcagcctgc agcctgaaga tattgcagtg    240
tattactgtc aacagagtta cagtatcctg atcaccttcg gccaagggac acgactggag    300
attaaacgaa ctgtggctgc accatctgtc                                     330
```

<210> SEQ ID NO 181
<211> LENGTH: 114
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (28)..(28)
<223> OTHER INFORMATION: Xaa1 is asparagine (Asn) or serine (Ser)
<220> FEATURE:
<221> NAME/KEY: MISC_FEATURE
<222> LOCATION: (30)..(30)
<223> OTHER INFORMATION: Xaa2 is lysine (Lys), tyrosine (Tyr), or
      asparagine (Asn)
<220> FEATURE:
<221> NAME/KEY: MISC_FEATURE
<222> LOCATION: (38)..(38)
<223> OTHER INFORMATION: Xaa3 is lysine (Lys) or glutamine (Gln)
<220> FEATURE:
<221> NAME/KEY: MISC_FEATURE
<222> LOCATION: (48)..(48)
<223> OTHER INFORMATION: Xaa4 is isoleucine (Ile) or methionine (Met)
<220> FEATURE:
<221> NAME/KEY: MISC_FEATURE
<222> LOCATION: (53)..(53)
<223> OTHER INFORMATION: Xaa5 is alanine (Ala) or proline (Pro)
<220> FEATURE:

```
<221> NAME/KEY: MISC_FEATURE
<222> LOCATION: (54)..(54)
<223> OTHER INFORMATION: Xaa6 is glutamic acid (Glu) or methionine (Met)
<220> FEATURE:
<221> NAME/KEY: MISC_FEATURE
<222> LOCATION: (56)..(56)
<223> OTHER INFORMATION: Xaa7 is glycine (Gly), asparagine (Asn), or
      aspartic acid (Asp)
<220> FEATURE:
<221> NAME/KEY: MISC_FEATURE
<222> LOCATION: (59)..(59)
<223> OTHER INFORMATION: Xaa8 is glutamic acid (Glu) or glutamine (Gln)
<220> FEATURE:
<221> NAME/KEY: MISC_FEATURE
<222> LOCATION: (61)..(61)
<223> OTHER INFORMATION: Xaa9 is alanine (Ala) or serine (Ser)
<220> FEATURE:
<221> NAME/KEY: MISC_FEATURE
<222> LOCATION: (65)..(65)
<223> OTHER INFORMATION: Xaa10 is glutamine (Gln) or arginine (Arg)
<220> FEATURE:
<221> NAME/KEY: MISC_FEATURE
<222> LOCATION: (77)..(77)
<223> OTHER INFORMATION: Xaa11 is aspartic acid (Asp) or asparagine
      (Asn)
<220> FEATURE:
<221> NAME/KEY: MISC_FEATURE
<222> LOCATION: (82)..(82)
<223> OTHER INFORMATION: Xaa12 is glutamic acid (Glu) or lysine (Lys)

<400> SEQUENCE: 181

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Xaa Ile Xaa Asp Asp
            20                  25                  30

Tyr Ile His Trp Val Xaa Gln Ala Pro Gly Lys Gly Leu Glu Trp Xaa
        35                  40                  45

Gly Trp Ile Asp Xaa Xaa Asn Xaa Asp Ser Xaa Tyr Xaa Ser Lys Phe
    50                  55                  60

Xaa Gly Arg Val Thr Ile Thr Val Asp Thr Ser Thr Xaa Thr Ala Tyr
65                  70                  75                  80

Met Xaa Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 182
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 182

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Ala Met Asn Asp Asp Ser Gln Tyr Ser Ser Lys Phe
    50                  55                  60

Gln Gly Arg Val Thr Ile Thr Val Asp Thr Ser Thr Asn Thr Ala Tyr
65                  70                  75                  80
```

Met Lys Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 183
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 183

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Ala Glu Asn Asp Asp Ser Gln Tyr Ser Ser Lys Phe
    50                  55                  60

Gln Gly Arg Val Thr Ile Thr Val Asp Thr Ser Thr Asn Thr Ala Tyr
65                  70                  75                  80

Met Lys Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 184
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 184

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Ala Glu Asn Asp Asp Ser Gln Tyr Ser Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 185
<211> LENGTH: 114
<212> TYPE: PRT

<213> ORGANISM: Artificial Sequence
<220> FEATURE:
<223> OTHER INFORMATION: Synthetic Sequence

<400> SEQUENCE: 185

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Ser Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Ala Glu Asn Asp Asp Ser Glu Tyr Ser Ser Lys Phe
    50                  55                  60

Gln Gly Arg Val Thr Ile Thr Val Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 186
<211> LENGTH: 114
<212> TYPE: PRT
<213> ORGANISM: Artificial Sequence
<220> FEATURE:
<223> OTHER INFORMATION: Synthetic Sequence

<400> SEQUENCE: 186

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Asp
            20                  25                  30

Tyr Ile His Trp Val Gln Gln Ala Pro Gly Lys Gly Leu Glu Trp Met
        35                  40                  45

Gly Trp Ile Asp Ala Glu Asn Asp Asp Ser Glu Tyr Ser Ser Lys Phe
    50                  55                  60

Gln Gly Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Tyr Ala Phe Gly Gly Tyr Trp Gly Gln Gly Thr Thr Val Thr Val
            100                 105                 110

Ser Ser

<210> SEQ ID NO 187
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 187

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asp Ser Asn Thr Tyr Leu His Trp Tyr Leu Gln Lys Pro Gly Gln Ser

```
                35                  40                  45

Pro Gln Leu Leu Ile Tyr Leu Ile Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ala Gln Ser
                 85                  90                  95

Thr His Val Pro Tyr Ala Phe Gly Gly Gly Thr Lys Val Glu Ile Lys
            100                 105                 110

Arg Thr Val Ala Ala Pro Ser Val
        115                 120

<210> SEQ ID NO 188
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 188

Asp Val Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
             20                  25                  30

Asp Gly Asn Thr Tyr Leu His Trp Tyr Leu Gln Lys Pro Gly Gln Ser
         35                  40                  45

Pro Gln Leu Leu Ile Tyr Leu Ile Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Gly Gln Ser
                 85                  90                  95

Thr His Val Pro Tyr Ala Phe Gly Gly Gly Thr Lys Val Glu Ile Lys
            100                 105                 110

Arg Thr Val Ala Ala Pro Ser Val
        115                 120

<210> SEQ ID NO 189
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 189

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
             20                  25                  30

Asp Ser Asn Thr Tyr Leu His Trp Tyr Leu Gln Lys Pro Gly Gln Ser
         35                  40                  45

Pro Gln Leu Leu Ile Tyr Leu Ile Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Gly Gln Ser
                 85                  90                  95
```

Thr His Val Pro Tyr Ala Phe Gly Gly Gly Thr Lys Val Glu Ile Lys
            100                 105                 110

Arg Thr Val Ala Ala Pro Ser Val
        115                 120

<210> SEQ ID NO 190
<211> LENGTH: 119
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (5)..(5)
<223> OTHER INFORMATION: Xaa1 Q,V
<220> FEATURE:
<221> NAME/KEY: MISC_FEATURE
<222> LOCATION: (11)..(11)
<223> OTHER INFORMATION: Xaa2 L,V
<220> FEATURE:
<221> NAME/KEY: MISC_FEATURE
<222> LOCATION: (12)..(12)
<223> OTHER INFORMATION: Xaa3 V,K
<220> FEATURE:
<221> NAME/KEY: MISC_FEATURE
<222> LOCATION: (13)..(13)
<223> OTHER INFORMATION: Xaa4  R,K
<220> FEATURE:
<221> NAME/KEY: MISC_FEATURE
<222> LOCATION: (17)..(17)
<223> OTHER INFORMATION: Xaa5 S,T
<220> FEATURE:
<221> NAME/KEY: MISC_FEATURE
<222> LOCATION: (20)..(20)
<223> OTHER INFORMATION: Xaa6 L,I
<220> FEATURE:
<221> NAME/KEY: MISC_FEATURE
<222> LOCATION: (23)..(23)
<223> OTHER INFORMATION: Xaa7 T,K
<220> FEATURE:
<221> NAME/KEY: MISC_FEATURE
<222> LOCATION: (38)..(38)
<223> OTHER INFORMATION: Xaa8 K,Q
<220> FEATURE:
<221> NAME/KEY: MISC_FEATURE
<222> LOCATION: (40)..(40)
<223> OTHER INFORMATION: Xaa9 R,A
<220> FEATURE:
<221> NAME/KEY: MISC_FEATURE
<222> LOCATION: (42)..(42)
<223> OTHER INFORMATION: Xaa10 E,G
<220> FEATURE:
<221> NAME/KEY: MISC_FEATURE
<222> LOCATION: (43)..(43)
<223> OTHER INFORMATION: Xaa11 Q,K
<220> FEATURE:
<221> NAME/KEY: MISC_FEATURE
<222> LOCATION: (48)..(48)
<223> OTHER INFORMATION: Xaa12 I,M
<220> FEATURE:
<221> NAME/KEY: MISC_FEATURE
<222> LOCATION: (55)..(55)
<223> OTHER INFORMATION: Xaa13 N,Q
<220> FEATURE:
<221> NAME/KEY: MISC_FEATURE
<222> LOCATION: (67)..(67)
<223> OTHER INFORMATION: Xaa14 K,R
<220> FEATURE:
<221> NAME/KEY: MISC_FEATURE
<222> LOCATION: (68)..(68)
<223> OTHER INFORMATION: Xaa15 A,V
<220> FEATURE:
<221> NAME/KEY: MISC_FEATURE
<222> LOCATION: (70)..(70)
<223> OTHER INFORMATION: Xaa16 L,I
<220> FEATURE:
<221> NAME/KEY: MISC_FEATURE

```
<222> LOCATION: (76)..(76)
<223> OTHER INFORMATION: Xaa17 A,T
<220> FEATURE:
<221> NAME/KEY: MISC_FEATURE
<222> LOCATION: (77)..(77)
<223> OTHER INFORMATION: Xaa18 N,D
<220> FEATURE:
<221> NAME/KEY: MISC_FEATURE
<222> LOCATION: (78)..(78)
<223> OTHER INFORMATION: Xaa19 I,T
<220> FEATURE:
<221> NAME/KEY: MISC_FEATURE
<222> LOCATION: (79)..(79)
<223> OTHER INFORMATION: Xaa20 V,A
<220> FEATURE:
<221> NAME/KEY: MISC_FEATURE
<222> LOCATION: (81)..(81)
<223> OTHER INFORMATION: Xaa21 L,M
<220> FEATURE:
<221> NAME/KEY: MISC_FEATURE
<222> LOCATION: (82)..(82)
<223> OTHER INFORMATION: Xaa22 H,E
<220> FEATURE:
<221> NAME/KEY: MISC_FEATURE
<222> LOCATION: (83)..(83)
<223> OTHER INFORMATION: Xaa23 F,L
<220> FEATURE:
<221> NAME/KEY: MISC_FEATURE
<222> LOCATION: (87)..(87)
<223> OTHER INFORMATION: Xaa24 T,R
<220> FEATURE:
<221> NAME/KEY: MISC_FEATURE
<222> LOCATION: (97)..(97)
<223> OTHER INFORMATION: Xaa25 T,A
<220> FEATURE:
<221> NAME/KEY: MISC_FEATURE
<222> LOCATION: (98)..(98)
<223> OTHER INFORMATION: Xaa26 L OR ABSENT
<220> FEATURE:
<221> NAME/KEY: MISC_FEATURE
<222> LOCATION: (99)..(99)
<223> OTHER INFORMATION: Xaa27 F OR ABSENT
<220> FEATURE:
<221> NAME/KEY: MISC_FEATURE
<222> LOCATION: (100)..(100)
<223> OTHER INFORMATION: Xaa28 A OR ABSENT
<220> FEATURE:
<221> NAME/KEY: MISC_FEATURE
<222> LOCATION: (101)..(101)
<223> OTHER INFORMATION: Xaa29 Y OR ABSENT
<220> FEATURE:
<221> NAME/KEY: MISC_FEATURE
<222> LOCATION: (102)..(102)
<223> OTHER INFORMATION: Xaa30 W OR ABSENT
<220> FEATURE:
<221> NAME/KEY: MISC_FEATURE
<222> LOCATION: (103)..(103)
<223> OTHER INFORMATION: Xaa31 G OR ABSENT
<220> FEATURE:
<221> NAME/KEY: MISC_FEATURE
<222> LOCATION: (104)..(104)
<223> OTHER INFORMATION: Xaa32  T,L
<220> FEATURE:
<221> NAME/KEY: MISC_FEATURE
<222> LOCATION: (113)..(113)
<223> OTHER INFORMATION: Xaa33 S,T
<220> FEATURE:
<221> NAME/KEY: MISC_FEATURE
<222> LOCATION: (114)..(114)
<223> OTHER INFORMATION: Xaa34 L,V
<220> FEATURE:
<221> NAME/KEY: MISC_FEATURE
<222> LOCATION: (115)..(115)
<223> OTHER INFORMATION: Xaa35 I,T

<400> SEQUENCE: 190

Glu Val Gln Leu Xaa Gln Ser Gly Ala Glu Xaa Xaa Xaa Pro Gly Ala
1               5                   10                  15
```

```
Xaa Val Lys Xaa Ser Cys Xaa Val Ser Gly Phe Asn Ile Lys Asp Asp
            20                  25                  30

Tyr Met Phe Trp Val Xaa Gln Xaa Pro Xaa Xaa Gly Leu Glu Trp Xaa
            35                  40                  45

Gly Trp Ile Asp Pro Glu Xaa Gly Asp Thr Glu Tyr Ala Ser Lys Phe
 50                      55                  60

Gln Asp Xaa Xaa Thr Xaa Thr Ala Asp Thr Ser Xaa Xaa Xaa Xaa Tyr
 65                  70                  75                  80

Xaa Xaa Xaa Ser Ser Leu Xaa Ser Glu Asp Thr Ala Val Tyr Tyr Cys
                85              90                  95

Xaa Xaa Xaa Xaa Xaa Xaa Xaa Xaa Phe Ala Tyr Trp Gly Gln Gly Thr
            100                 105                 110

Xaa Xaa Xaa Val Ser Ser Ala
        115
```

<210> SEQ ID NO 191
<211> LENGTH: 119
<212> TYPE: PRT
<213> ORGANISM: Artificial Sequence
<220> FEATURE:
<223> OTHER INFORMATION: Synthetic Sequence
<220> FEATURE:
<221> NAME/KEY: MISC_FEATURE
<222> LOCATION: (55)..(55)
<223> OTHER INFORMATION: Xaa1 N,Q
<220> FEATURE:
<221> NAME/KEY: MISC_FEATURE
<222> LOCATION: (77)..(77)
<223> OTHER INFORMATION: Xaa2 N,D
<220> FEATURE:
<221> NAME/KEY: MISC_FEATURE
<222> LOCATION: (97)..(97)
<223> OTHER INFORMATION: Xaa3 T,A
<220> FEATURE:
<221> NAME/KEY: MISC_FEATURE
<222> LOCATION: (98)..(98)
<223> OTHER INFORMATION: Xaa4 L or ABSENT
<220> FEATURE:
<221> NAME/KEY: MISC_FEATURE
<222> LOCATION: (99)..(99)
<223> OTHER INFORMATION: Xaa5 F or ABSENT
<220> FEATURE:
<221> NAME/KEY: MISC_FEATURE
<222> LOCATION: (100)..(100)
<223> OTHER INFORMATION: Xaa6 A or ABSENT
<220> FEATURE:
<221> NAME/KEY: MISC_FEATURE
<222> LOCATION: (101)..(101)
<223> OTHER INFORMATION: Xaa7 Y or ABSENT
<220> FEATURE:
<221> NAME/KEY: MISC_FEATURE
<222> LOCATION: (102)..(102)
<223> OTHER INFORMATION: Xaa8 W or ABSENT
<220> FEATURE:
<221> NAME/KEY: MISC_FEATURE
<222> LOCATION: (103)..(103)
<223> OTHER INFORMATION: Xaa9 G or ABSENT
<220> FEATURE:
<221> NAME/KEY: MISC_FEATURE
<222> LOCATION: (104)..(104)
<223> OTHER INFORMATION: Xaa10 T,L

<400> SEQUENCE: 191

```
Glu Val Gln Leu Val Gln Ser Gly Ala Glu Val Lys Lys Pro Gly Ala
 1               5                   10                  15

Thr Val Lys Ile Ser Cys Lys Val Ser Gly Phe Asn Ile Lys Asp Asp
            20                  25                  30

Tyr Met Phe Trp Val Gln Gln Ala Pro Gly Lys Gly Leu Glu Trp Met
```

```
                35                  40                  45

Gly Trp Ile Asp Pro Glu Xaa Gly Asp Thr Glu Tyr Ala Ser Lys Phe
         50                  55                  60

Gln Asp Arg Val Thr Ile Thr Ala Asp Thr Ser Thr Xaa Thr Ala Tyr
 65                  70                  75                  80

Met Glu Leu Ser Ser Leu Arg Ser Glu Asp Thr Ala Val Tyr Tyr Cys
                 85                  90                  95

Xaa Xaa Xaa Xaa Xaa Xaa Xaa Phe Ala Tyr Trp Gly Gln Gly Thr
             100                 105                 110

Thr Val Thr Val Ser Ser Ala
            115

<210> SEQ ID NO 192
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 192

Glu Val Gln Leu Gln Gln Ser Gly Ala Glu Leu Val Arg Pro Gly Ala
  1               5                  10                  15

Ser Val Lys Leu Ser Cys Thr Val Ser Gly Phe Asn Ile Lys Asp Asp
                 20                  25                  30

Tyr Met Phe Trp Val Lys Gln Arg Pro Glu Gln Gly Leu Glu Trp Ile
             35                  40                  45

Gly Trp Ile Asp Pro Glu Asn Gly Asp Thr Glu Tyr Ala Ser Lys Phe
         50                  55                  60

Gln Asp Lys Ala Thr Leu Thr Ala Asp Thr Ser Ala Asn Ile Val Tyr
 65                  70                  75                  80

Leu His Phe Ser Ser Leu Thr Ser Glu Asp Thr Ala Val Tyr Tyr Cys
                 85                  90                  95

Thr Leu Phe Ala Tyr Trp Gly Gln Gly Thr Ser Leu Ile Val Ser Ser
             100                 105                 110

Ala

<210> SEQ ID NO 193
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 193

Glu Val Gln Leu Val Gln Ser Gly Ala Glu Val Lys Lys Pro Gly Ala
  1               5                  10                  15

Thr Val Lys Ile Ser Cys Lys Val Ser Gly Phe Asn Ile Lys Asp Asp
                 20                  25                  30

Tyr Met Phe Trp Val Gln Gln Ala Pro Gly Lys Gly Leu Glu Trp Met
             35                  40                  45

Gly Trp Ile Asp Pro Glu Asn Gly Asp Thr Glu Tyr Ala Ser Lys Phe
         50                  55                  60

Gln Asp Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Phe Ala Tyr Trp Gly Gln Gly Thr Thr Val Thr Val Ser Ser
```

<210> SEQ ID NO 194
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 194

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Asp
            20                  25                  30

Tyr Met Phe Trp Val Gln Ala Pro Gly Lys Gly Leu Glu Trp Met
        35                  40                  45

Gly Trp Ile Asp Pro Glu Asn Gly Asp Thr Glu Tyr Ala Ser Lys Phe
    50                  55                  60

Gln Asp Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Leu Phe Ala Tyr Trp Gly Gln Gly Thr Thr Val Thr Val Ser Ser
            100                 105                 110

Ala
```

<210> SEQ ID NO 195
<211> LENGTH: 119
<212> TYPE: PRT
<213> ORGANISM: Artificial Sequence
<220> FEATURE:
<223> OTHER INFORMATION: Synthetic Sequence

<400> SEQUENCE: 195

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Asp
            20                  25                  30

Tyr Met Phe Trp Val Gln Ala Pro Gly Lys Gly Leu Glu Trp Met
        35                  40                  45

Gly Trp Ile Asp Pro Glu Gln Gly Asp Thr Glu Tyr Ala Ser Lys Phe
    50                  55                  60

Gln Asp Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Thr Leu Phe Ala Tyr Trp Gly Leu Phe Ala Tyr Trp Gly Gln Gly Thr
            100                 105                 110

Thr Val Thr Val Ser Ser Ala
        115
```

<210> SEQ ID NO 196
<211> LENGTH: 113
<212> TYPE: PRT
<213> ORGANISM: Artificial Sequence
<220> FEATURE:
<223> OTHER INFORMATION: Synthetic Sequence
<220> FEATURE:

<221> NAME/KEY: MISC_FEATURE
<222> LOCATION: (7)..(7)
<223> OTHER INFORMATION: Xaa1 T,S
<220> FEATURE:
<221> NAME/KEY: MISC_FEATURE
<222> LOCATION: (10)..(10)
<223> OTHER INFORMATION: Xaa2 T,S
<220> FEATURE:
<221> NAME/KEY: MISC_FEATURE
<222> LOCATION: (12)..(12)
<223> OTHER INFORMATION: Xaa3  S,P
<220> FEATURE:
<221> NAME/KEY: MISC_FEATURE
<222> LOCATION: (41)..(41)
<223> OTHER INFORMATION: Xaa4 L,F
<220> FEATURE:
<221> NAME/KEY: MISC_FEATURE
<222> LOCATION: (42)..(42)
<223> OTHER INFORMATION: Xaa5  Q,L
<220> FEATURE:
<221> NAME/KEY: MISC_FEATURE
<222> LOCATION: (50)..(50)
<223> OTHER INFORMATION: Xaa6 R,K
<220> FEATURE:
<221> NAME/KEY: MISC_FEATURE
<222> LOCATION: (68)..(68)
<223> OTHER INFORMATION: Xaa7 A,S
<220> FEATURE:
<221> NAME/KEY: MISC_FEATURE
<222> LOCATION: (88)..(88)
<223> OTHER INFORMATION: Xaa8  V,L
<220> FEATURE:
<221> NAME/KEY: MISC_FEATURE
<222> LOCATION: (109)..(109)
<223> OTHER INFORMATION: Xaa9 L,V

<400> SEQUENCE: 196

Asp Val Val Met Thr Gln Xaa Pro Leu Xaa Leu Xaa Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Xaa Xaa Gln Arg Pro Gly Gln Ser
        35                  40                  45

Pro Xaa Arg Leu Ile Tyr Leu Val Ser Lys Leu Asp Ser Gly Val Pro
    50                  55                  60

Asp Arg Phe Xaa Gly Ser Gly Ser Gly Thr Asp Phe Thr Leu Lys Ile
65                  70                  75                  80

Ser Arg Val Glu Ala Glu Asp Xaa Gly Val Tyr Tyr Cys Trp Gln Gly
                85                  90                  95

Ala His Phe Pro Gln Thr Phe Gly Gly Gly Thr Lys Xaa Glu Ile Lys
            100                 105                 110

Arg

<210> SEQ ID NO 197
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

-continued

```
Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Ser Tyr Ser Thr Pro Leu
                 85                  90                  95

Thr Phe Gly Gly Gly Thr Lys Val Glu Ile Lys Arg
            100                 105
```

<210> SEQ ID NO 198
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 198

```
Asp Val Val Met Thr Gln Thr Pro Leu Thr Leu Ser Val Thr Leu Gly
 1               5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Leu Leu Gln Arg Pro Gly Gln Ser
             35                  40                  45

Pro Lys Arg Leu Ile Tyr Leu Val Ser Lys Leu Asp Ser Gly Val Pro
 50                  55                  60

Asp Arg Phe Ala Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Ala His Phe Pro Gln Thr Phe Gly Gly Gly Thr Lys Leu Glu Ile Lys
            100                 105                 110

Arg
```

<210> SEQ ID NO 199
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 199

```
Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Phe Gln Gln Arg Pro Gly Gln Ser
             35                  40                  45

Pro Arg Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Ala His Phe Pro Gln Thr Phe Gly Gly Gly Thr Lys Val Glu Ile Lys
            100                 105                 110

Arg
```

```
<210> SEQ ID NO 200
<211> LENGTH: 113
<212> TYPE: PRT
<213> ORGANISM: Artificial Sequence
<220> FEATURE:
<223> OTHER INFORMATION: Synthetic Sequence

<400> SEQUENCE: 200

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ala His Phe Pro Gln Thr Phe Gly Gly Gly Thr Lys Val Glu Ile Lys
                100                 105                 110

Arg
```

US 10,836,824 B2

ANTIBODIES DIRECTED AGAINST LYMPHOCYTE ACTIVATION GENE 3 (LAG-3)

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 182,646 Byte ASCII (Text) file named "723163_ST25-Revised.TXT," created on Oct. 25, 2017.

BACKGROUND OF THE INVENTION

Lymphocyte Activation Gene-3 (LAG-3), which is also known as CD223, is a member of the immunoglobulin supergene family and is structurally and genetically related to CD4. LAG-3 is expressed on T-cells, B cells, natural killer (NK) cells and plasmacytoid dendritic cells (pDCs). Like CD4, LAG-3 has been demonstrated to interact with MHC Class II molecules (Baixeras et al., *J. Exp. Med.*, 176: 327-337 (1992)), but binds at a distinct site (Huard et al. *Proc. Natl. Acad. Sci. USA*, 94(11): 5744-5749 (1997)). In particular, for example, a LAG-3 immunoglobulin fusion protein (SLAG-3Ig) directly and specifically binds via LAG-3 to MHC class II on the cell surface (Huard et al., *Eur. J. Immunol.*, 26: 1180-1186 (1996)).

LAG-3 is upregulated following T-cell activation, and modulates T-cell function as well as T-cell homeostasis (Sierra et al., *Expert Opin. Ther. Targets*, 15(1):91-101 (2011)). The LAG-3/MHC class II interaction may play a role in down-regulating antigen-dependent stimulation of CD4+ T lymphocytes, as demonstrated in in vitro studies of antigen-specific T-cell responses in which the addition of anti-LAG-3 antibodies led to increased T-cell proliferation, higher expression of activation antigens such as CD25, and higher concentrations of cytokines such as interferon-gamma, and interleukin-4 (Huard et al., *Eur. J. Immunol.*, 24: 3216-3221 (1994)). CD4+CD25+ regulatory T-cells (Treg) also have been shown to express LAG-3 upon activation and antibodies to LAG-3 inhibit suppression by induced Treg cells, both in vitro and in vivo, suggesting that LAG-3 contributes to the suppressor activity of Treg cells (Huang et al. *Immunity*, 21: 503-513 (2004)). Furthermore, LAG-3 has been shown to negatively regulate T-cell homeostasis by regulatory T-cells in both T-cell-dependent and independent mechanisms (Workman, C. J. and Vignali, D. A., *J. Immunol.*, 174: 688-695 (2005)).

Subsets of conventional T-cells that are anergic or display impaired functions express LAG-3, and LAG-3+ T-cells are enriched at tumor sites and during chronic viral infections. However, while LAG-3 knockout mice have been shown to mount normal virus-specific CD-4+ and CD8+ T-cell responses, suggesting a non-essential role for LAG-3, blockade of the PD-1/PD-L1 pathway combined with LAG-3 blockade improved viral control as compared with PD-L1 blockade alone (Blackburn et al., *Nat. Immunol.*, 10: 29-37 (2009); and Richter et al., *Int. Immunol.*, 22: 13-2 (2010)).

In a self-tolerance/tumor mouse model where transgenic CD8+ T-cells were rendered unresponsive/anergic in vivo, LAG-3 blockade or deficiency in CD8+ T-cells enhanced T-cell proliferation, T-cell recruitment and effector functions at the tumor site (Grosso et al., *J. Clin. Invest.*, 117: 3383-92 (2007)).

Inhibition of LAG-3 activity, such as through use of monoclonal antibodies, is currently under investigation as a therapeutic approach to treat viral infections and melanoma based on preclinical studies. For example, addition of soluble huLAG-3 fused to an Fc region enhanced the proliferation of antigen-specific T-cells to viral and tumor antigens, such as influenza matrix protein or melanoma antigen recognized by T-cells (MART-1), in PBMCs of healthy or cancer patients (Casati et al., *J. Immunol*, 180: 3782-3788 (2008)).

There is a need for additional antagonists of LAG-3 (e.g., an antibody) that binds LAG-3 with high affinity and effectively neutralizes LAG-3 activity. The invention provides such LAG-3-binding agents.

BRIEF SUMMARY OF THE INVENTION

The invention provides an isolated immunoglobulin heavy chain polypeptide which comprises the amino acid sequence Glu Val Gln Leu Val Gln Ser Gly Ala Glu Val Lys Lys Pro Gly Ala Thr Val Lys Ile Ser Cys Lys Ala Ser Gly Phe Xaa1 Ile Xaa2 Asp Asp Tyr Ile His Trp Val Xaa3 Gln Ala Pro Gly Lys Gly Leu Glu Trp Xaa4 Gly Trp Ile Asp Xaa5 Xaa6 Asn Xaa7 Asp Ser Xaa8 Tyr Xaa9 Ser Lys Phe Xaa10 Gly Arg Val Thr Ile Thr Val Asp Thr Ser Thr Xaa11 Thr Ala Tyr Met Xaa12 Leu Ser Ser Leu Arg Ser Glu Asp Thr Ala Val Tyr Tyr Cys Thr Tyr Ala Phe Gly Gly Tyr Trp Gly Gln Gly Thr Thr Val Thr Val Ser Ser (SEQ ID NO: 181), wherein (a) Xaa1 is asparagine (Asn) or serine (Ser), (1)) Xaa2 is lysine (Lys), tyrosine (Tyr), or asparagine (Asn), (c) Xaa3 is lysine (Lys) or glutamine (Gln), (d) Xaa4 is isoleucine (Ile) or methionine (Met), (e) Xaa5 is alanine (Ala) or proline (Pro), (f) Xaa6 is glutamic acid (Glu) or methionine (Met), (g) Xaa6 is glycine (Gly), asparagine (Asn), or aspartic acid (Asp), (h) Xaa8 is glutamic acid (Glu) or glutamine (Q), (i) Xaa9 is alanine (Ala) or serine (Ser), (j) Xaa10 is glutamine (Gln) or arginine (Arg), (k) Xaa11 is aspartic acid (Asp) or asparagine (Asn), and (l) Xaa12 is glutamine (Gln) or lysine (Lys).

The invention provides an isolated immunoglobulin heavy chain polypeptide which comprises the amino acid sequence Gln Val Gln Leu Gln Gln Trp Gly Ala Xaa1 Leu Leu Lys Pro Ser Glu Thr Leu Ser Leu Xaa2 Cys Xaa3 Val Tyr Gly Gly Xaa4 Phe Xaa5 Gly Tyr Tyr Trp Xaa6 Trp Ile Arg Gln Pro Pro Xaa7 Lys Gly Leu Glu Trp Ile Gly Glu Ile Asn His Ser Gly Xaa8 Thr Asn Tyr Asn Pro Ser Leu Lys Ser Arg Val Thr Ile Ser Val Asp Thr Ser Lys Asn Gln Xaa9 Ser Leu Lys Leu Xaa10 Xaa11 Val Thr Ala Ala Asp Thr Ala Val Tyr Tyr Cys Xaa12 Arg Glu Gly Xaa13 Tyr Gly Asp Tyr Asp Tyr Trp Gln Gly Thr Leu Val Thr Val Ser Ser (SEQ ID NO: 35), wherein (a) Xaa1 is arginine (Arg) or glycine (Gly), (b) Xaa2 is threonine (Thr) or isoleucine (Ile), (c) Xaa3 is threonine (Thr) or alanine (Ala), (d) Xaa4 is serine (Ser) or phenylalanine (Phe), (e) Xaa5 is serine (Ser) or phenylalanine (Phe), (f) Xaa6 is serine (Ser) or isoleucine (Ile), (g) Xaa7 is glycine (Gly) or arginine (Arg), (h) Xaa8 is serine (Ser) or asparagine (Asn), (i) Xaa9 is phenylalanine (Phe) or leucine (Leu), (j) Xaa10 is asparagine (Asn) or serine (Ser), (k) Xaa11 is serine (Ser) or phenylalanine (Phe), (l) Xaa12 is alanine (Ala) or valine (Val), and (m) Xaa13 is aspartic acid (Asp) or asparagine (Asn).

The invention further provides an isolated immunoglobulin heavy chain polypeptide comprising SEQ. ID NO: 190 or 191.

The invention provides an isolated immunoglobulin light chain polypeptide which comprises the amino acid sequence Asp Xaa1 Val Met Thr Gln Thr Pro Leu Ser Leu Ser Val Thr Pro Gly Gln Pro Ala Ser Ile Ser Cys Arg Xaa2 Ser Gln Ser Leu Val His Ser Asp Xaa3 Xaa4 Thr Tyr Leu His Trp Tyr Leu Gln Lys Pro Gly Gln Ser Pro Gln Leu Leu Ile Tyr Xaa Xaa Ser Asn Arg Phe Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Phe Cys Xaa Gln Ser Thr Xaa Val Pro Tyr Ala Phe Gly Gly Gly Thr Lys Val Glu Ile Lys Arg Thr (SEQ ID NO: 57), wherein (a) Xaa1 is valine (Val) or isoleucine (Ile), (b) Xaa2 is cysteine (Cys) or serine (Ser), (e) Xaa3 is glycine (Gly) or serine (Ser), (d) Xaa4 is asparagine (Asn) or aspartic acid (Asp), (e) Xaa5 is lysine (Lys), glycine (Gly), asparagine (Asn), serine (Ser), or leucine (Leu), (f) Xaa6 is valine (Val) or isoleucine (g) Xaa7 is serine (Ser), alanine (Ala), or glycine (Gly), and (h) Xaa8 is histidine (His) or tyrosine (Tyr).

The invention provides an isolated immunoglobulin light chain polypeptide which comprises the amino acid sequence Asp Ile Gln Met Thr Gln Ser Pro Ser Ser Leu Ser Ala Ser Val Gly Asp Arg Thr Ile Thr Cys Gln Ala Ser Gln Asp Ile Ser Asn Tyr Leu Asn Trp Tyr Gln Gln Lys Pro Gly Lys Ala Pro Lys Leu Leu Ile Xaa1 Xaa2 Xaa3 Xaa4 Xaa5 Leu Glu Thr Gly Val Pro Ser Arg Phe Ser Gly Ser Gly Ser Gly Thr Asp Phe Thr Phe Thr Ile Ser Ser Leu Gln Pro Glu Asp Ile Ala Val Tyr Tyr Cys Gln Gln Ser Tyr Ser Xaa6 Leu Ile Thr Phe Gly Gln Gly Thr Arg Leu Glu Ile Lys Arg Thr Val Ala Ala Pro Ser Val (SEQ ID NO: 89), wherein (a) the subsequence Xaa1 Xaa2 Xaa3 Xaa4 Xaa5 is deleted or is Tyr-Asp-Ala-Ser-Asn, and (b) Xaa6 is threonine (Thr) or isoleucine (Ile).

The invention also provides isolated immunoglobulin light chain polypeptide comprising SEQ ID NO: 196 or 197.

In addition, the invention provides isolated or purified nucleic acid sequences encoding the foregoing immunoglobulin polypeptides, vectors comprising such nucleic acid sequences, LAG-3-binding agents comprising the foregoing immunoglobulin polypeptides, nucleic acid sequences encoding such LAG-3-binding agents, vectors comprising such nucleic acid sequences, isolated cells comprising such vectors, compositions comprising such LAG-3-binding agents or such vectors with a pharmaceutically acceptable carrier, and methods of treating cancer or infectious diseases in mammals by administering effective amounts of such compositions to mammals.

BRIEF DESCRIPTION OF THE DRAWINGS

FIG. 1A is a graph of mean tumor volume over time in mice implanted with Colon26 colon adenocarcinoma cells and injected with the indicated antibodies. Each data plot in the figure refers to the indicated treatment group.

DETAILED DESCRIPTION OF THE INVENTION

Figure 1B:
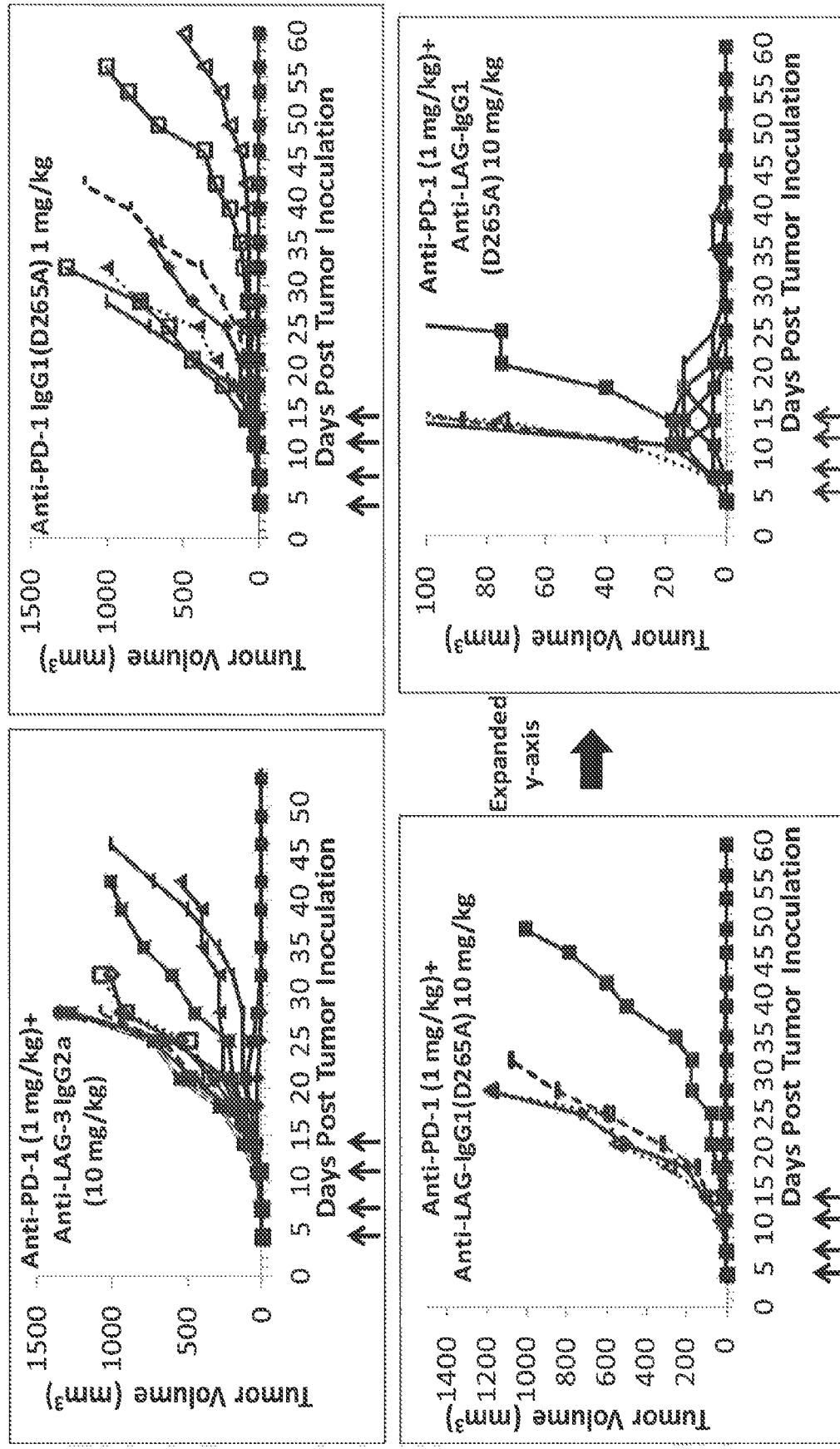
FIG. 1B is a graph of tumor volume over time of individual animals in three treatment groups of mice implanted with Colon26 colon adenocarcinoma cells and injected with the indicated antibodies. Each data plot in the graphs refers to an individual animal in the treatment group.

The invention provides an isolated immunoglobulin heavy chain polypeptide and/or an isolated immunoglobulin light chain polypeptide, or a fragment (e.g., antigen-binding fragment) thereof. The term "immunoglobulin" or "antibody," as used herein, refers to a protein that is found in blood or other bodily fluids of vertebrates, which is used by the immune system to identify and neutralize foreign objects, such as bacteria and viruses. The polypeptide is "isolated" in that it is removed from its natural environment. In a preferred embodiment, an immunoglobulin or antibody is a protein that comprises at least one complementarity determining region (CDR). The CDRs form the "hypervariable region" of an antibody, which is responsible for antigen binding (discussed further below). A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($C_H1$, $C_H2$, and $C_H3$) regions, and each light chain contains one N-terminal variable ($V_L$) region and one C-terminal constant ($C_L$) region. The light chains of antibodies can be assigned to one of two distinct types, either kappa (κ) or lambda (λ), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The $V_H$ and $V_L$ regions have the same general structure, with each region comprising four framework (FW or FR) regions. The term "framework region," as used herein, refers to the relatively conserved amino acid sequences within the variable region which are located between the hypervariable or complementary determining regions (CDRs). There are four framework regions in each variable domain, which are designated FR1, FR2, FR3, and FR4. The framework regions form the β sheets that provide the structural framework of the variable region (see, e.g., C. A. Janeway et al. (eds.), *Immunobiology*, 5th Ed., Garland Publishing, New York, N.Y. (2001)).

The framework regions are connected by three complementarity determining regions (CDRs). As discussed above, the three CDRs, known as CDR1, CDR2, and CDR3, form the "hypervariable region" of an antibody, which is responsible for antigen binding. The CDRs form loops connecting, and in some cases comprising part of, the beta-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent complement-mediated lysis or antibody-dependent cellular toxicity via interactions with effector molecules and cells.

The isolated immunoglobulin heavy chain polypeptide and the isolated immunoglobulin light chain polypeptide of the invention desirably bind to the protein encoded by the Lymphocyte Activation Gene-3 (LAG-3) (also referred to herein as "LAG-3 protein"). As discussed above, LAG-3 is a 498 amino acid protein that negatively regulates T-cell function and homeostasis (Triebel et al., *J. Exp. Med.*, 171(5): 1393-1405 (1990); and Triebel F., *Trends Immunol.*, 24(12): 619-22 (2003)). LAG-3 is a member of the immunoglobulin supergene family and is structurally and genetically related to CD4. The intra-cytoplasmic region of LAG-3 has been shown to interact with a protein denoted LAP, which is thought to be a signal transduction molecule involved in the downregulation of the CD3/TCR activation pathway (Iouzalen et al., *Eur. J. Immunol.*, 31: 2885-2891 (2001)). Furthermore, CD4+CD25+ regulatory T-cells (Treg) have been shown to express LAG-3 upon activation and antibodies to LAG-3 inhibit suppression by induced Treg cells, both in vitro and in vivo, suggesting that LAG-3 contributes to the suppressor activity of Treg cells (Huang et al., *Immunity*, 21: 503-513 (2004)). However, recent study suggests that LAG-3 expression on CD4+ T-cells renders them more susceptible to suppression by Tregs, rather than making Tregs more suppressive (see Durham et al., *PLoS ONE*, 9(11): e109080 (2014)). In certain circumstances, LAG-3 also has been shown to have immunostimulatory effects (see, e.g., Prigent et al., *Eur. J. Immunol.*, 29: 3867-3876 (1999)); El Mir and Triebel, *J. Immunol.*, 164: 5583-5589 (2000)); and Casati et al., *Cancer Res.*, 66: 4450-4460 (2006)). The inventive isolated immunoglobulin heavy chain polypeptide and the inventive isolated immunoglobulin light chain polypeptide can form an agent that binds to LAG-3 and another antigen, resulting in a "dual reactive" binding agent (e.g., a dual reactive antibody). For example, the agent can bind to LAG-3 and to another negative regulator of the immune system such as, for example, programmed death 1 (PD-1) and/or T-cell immunoglobulin domain and mucin domain 3 protein (TIM-3).

Antibodies which bind to LAG-3, and components thereof, are known in the art (see, e.g., U.S. Patent Application Publication Nos. 2010/0233183, 2011/0150892, and 2014/0093511). Anti-LAG-3 antibodies also are commercially available from sources such as, for example, Abcam (Cambridge, Mass.), and R&D Systems, Inc. (Minneapolis, Minn.).

The invention provides an isolated immunoglobulin heavy chain polypeptide which comprises the amino acid sequence Glu Val Gln Leu Val Gln Ser Gly Ala Glu Val Lys Lys Pro Gly Ala Thr Val Lys Ile Ser Cys Lys Ala Ser Gly Phe Xaa1 Ile Xaa2 Asp Asp Tyr Ile His Trp Val Xaa3 Gln Ala Pro Gly Lys Gly Leu Glu Trp Xaa4 Gly Trp Ile Asp Xaa5 Xaa6 Asn Xaa7 Asp Ser Xaa8 Tyr Xaa9 Ser Lys Phe Xaa10 Gly Arg Val Thr Ile Thr Val Asp Thr Ser Thr Xaa11 Thr Ala Tyr Met Xaa12 Leu Ser Ser Leu Arg Ser Glu Asp Thr Ala Val Tyr Tyr Cys Thr Tyr Ala Phe Gly Gly Tyr Trp Gly Gln Gly Thr Thr Val Thr Val Ser Ser (SEQ ID NO: 181), wherein (a) Xaa1 is asparagine (Asn) or serine (Ser), (b) Xaa2 is lysine (Lys), tyrosine (Tyr), or, asparagine (Asn), (c) Xaa3 is lysine (Lys) or glutamine (Gln), (d) Xaa4 is isoleucine (Ile) or methionine (Met), (e) Xaa5 is alanine (Ala) or proline (Pro), (f) Xaa6 is glutamic acid (Glu) or methionine (Met), (g) Xaa6 is glycine (Gly), asparagine (Asn), or aspartic acid (Asp), (h) Xaa8 is glutamic acid (Glu) or glutamine (Q), (i) Xaa9 is alanine (Ala) or serine (Ser), (j) Xaa10 is glutamine (Gln) or arginine (Arg), (k) Xaa11 is aspartic acid (Asp) or asparagine (Asn), and (l) Xaa12 is glutamine (Gln) or lysine (Lys).

In another aspect, the inummoglobulin heavy chain polypeptide comprises, consists of, or consists essentially of the amino acid sequence Glu Val Gln Leu Val Gln Ser Gly Ala Glu Val Lys Lys Pro Gly Ala Thr Val Lys Ile Ser Cys Lys Ala Ser Gly Phe Xaa1 Ile Xaa2 Asp Asp Tyr Ile His Trp Val Xaa3 Gln Ala Pro Gly Lys Gly Leu Glu Trp Xaa4 Gly Trp Ile Asp Xaa5 Glu Asn Xaa6 Asp Ser Glu Tyr Xaa7 Ser Lys Phe Xaa8 Gly Arg Val Thr Ile Thr Val Asp Thr Ser Thr Xaa9 Thr Ala Tyr Met Glu Leu Ser Ser Leu Arg Ser Glu Asp Thr Ala Val Tyr Tyr Cys Thr Tyr Ala Phe Gly Gly Tyr Trp Gly Gln Gly Thr Thr Val Thr Val Ser Ser (SEQ ID NO: 1), wherein (a) Xaa1 is asparagine (Asn) or serine (Ser), (b) Xaa2 is lysine (Lys), tyrosine (Tyr), or asparagine (Asn), (c) Xaa3 is lysine (Lys) or glutamine (Gln), (d) Xaa4 is isoleucine (Ile) or methionine (Met), (e) Xaa5 is alanine (Ala) or proline (Pro), (f) Xaa6 is glycine (Gly), asparagine (Asn), or aspartic acid (Asp), (g) Xaa7 is alanine (Ala) or serine (Ser), (h) Xaa8 is glutamine (Gln) or arginine (Arg), and (i) Xaa9 is aspartic acid (Asp) or asparagine (Asn).

In one embodiment, the isolated immunoglobulin heavy chain polypeptide comprises, consists of, or consists essentially of an amino acid sequence of any one of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 182, SEQ ID NO: 183, SEQ ID NO: 184, SEQ ID NO: 185, or SEQ ID NO: 186.

The invention also provides an immunoglobulin heavy chain polypeptide that comprises, consists of, or consists essentially of the amino acid sequence Gln Val Gln Leu Gln Gln Trp Gly Ala Xaa1 Leu Leu Lys Pro Ser Glu Thr Leu Ser Leu Xaa2 Cys Xaa3 Val Tyr Gly Gly Xaa4 Phe Xaa5 Gly Tyr Tyr Trp Xaa6 Trp Ile Arg Gln Pro Pro Xaa7 Lys Gly Leu Glu Trp Ile Gly Glu Ile Asn His Ser Gly Xaa8 Thr Asn Tyr Asn Pro Ser Leu Lys Ser Arg Val Thr Ile Ser Val Asp Thr Ser Lys Asn Gln Xaa9 Ser Leu Lys Leu Xaa10 Xaa11 Val Thr Ala Ala Asp Thr Ala Val Tyr Tyr Cys Xaa12 Arg Glu Gly Xaa13 Tyr Gly Asp Tyr Asp Tyr Trp Gly Gln Gly Thr Leu Val Thr Val Ser Ser (SEQ ID NO: 35), wherein (a) Xaa1 is arginine (Arg) or glycine (Gly), (b) Xaa2 is threonine (Thr) or isoleucine (Ile), (c) Xaa3 is threonine (Thr) or alanine (Ala), (d) Xaa4 is serine (Ser) or phenylalanine (Phe), (e) Xaa5 is serine (Ser) or phenylalanine (Phe), (f) Xaa6 is serine (Ser) or isoleucine (Ile), (g) Xaa7 is glycine (Gly) or arginine (Arg), (h) Xaa8 is serine (Ser) or asparagine (Asn), (i) Xaa9 is phenylalanine (Phe) or leucine (Leu), (j) Xaa10 is asparagine (Asn) or serine (Ser), (k) Xaa11 is serine (Ser) or phenylalanine (Phe), (l) Xaa12 is alanine (Ala) or valine (Val), and (m) Xaa13 is aspartic acid (Asp) or asparagine (Asn).

In one embodiment, the isolated immunoglobulin heavy chain polypeptide comprises, consists of, or consists essentially of an amino acid sequence of any one of SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, or SEQ ID NO: 56.

In another embodiment, there is provided an isolated immunoglobulin heavy chain polypeptide which comprises SEQ ID NO: 190 or 191. Examples of such a polypeptide include those comprising any one of SEQ ID NOs: 192-195.

When the inventive immunoglobulin heavy chain polypeptide consists essentially of an amino acid sequence of any one of SEQ ID NO: 1-SEQ ID NO: 56, SEQ ID NOS: 182-186, or SEQ ID NOS: 190-195, additional components can be included in the polypeptide that do not materially affect the polypeptide (e.g., protein moieties such as biotin that facilitate purification or isolation). When the inventive immunoglobulin heavy chain polypeptide consists of an amino acid sequence of any one of SEQ ID NO: 1-SEQ ID NO: 56, the polypeptide does not comprise any additional components (i.e., components that are not endogenous to the inventive immunoglobulin heavy chain polypeptide).

The invention provides an isolated immunoglobulin heavy chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to any one of SEQ ID NO: 1-56. Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and PASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 21(3): 403-410 (1990), Beigert et al., *Proc. Natl. Acad. Sci. USA.*, 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics* 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)).

In another embodiment, the invention provides an immunoglobulin light chain polypeptide that comprises, consists of, or consists essentially of, an isolated immunoglobulin light chain polypeptide which comprises the amino acid sequence Asp Xaa1 Val Met Thr Gln Thr Pro Leu Ser Leu Ser Val Thr Pro Gly Gln Pro Ala Ser Ile Ser Cys Arg Xaa2 Ser Gln Ser Leu Val His Ser Asp Xaa3 Xaa4 Thr Tyr Leu His Trp Tyr Leu Gln Lys Pro Gly Gln Ser Pro Gln Leu Leu Ile Tyr Xaa Xaa Ser Asn Arg Phe Ser Gly Val Pro Asp Arg Phe Ser Gly Ser Gly Ser Gly Thr Asp Phe Thr Leu Lys Ile Ser Arg Val Glu Ala Glu Asp Val Gly Val Tyr Phe Cys Xaa Gln Ser Thr Xaa Val Pro Tyr Ala Phe Gly Gly Gly Thr Lys Val Glu Ile Lys Arg Thr (SEQ ID NO: 57), wherein (a) Xaa1 is valine (Val) or isoleucine (Ile), (b) Xaa2 is cysteine (Cys) or serine (Ser), (c) Xaa3 is glycine (Gly) or serine (Ser), (d) Xaa4 is asparagine (Asn) or aspartic acid (Asp), (e) Xaa5 is lysine (Lys), glycine (Gly), asparagine (Asn), serine (Ser), or leucine (Leu), (f) Xaa6 is valine (Val) or isoleucine (Ile), (g) Xaa7 is serine (Ser), alanine (Ala), or glycine (Gly), and (h) Xaa8 is histidine (His) or tyrosine (Tyr).

In one embodiment, the isolated immunoglobulin light chain polypeptide comprises, consists of, or consists essentially of an amino acid sequence of any one of SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO; 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 187, SEQ ID NO: 188, or SEQ ID NO: 189.

The invention provides an isolated immunoglobulin light chain polypeptide which comprises, consists essentially of, or consists of the amino acid sequence Asp Ile Gln Met Thr Gln Ser Pro Ser Ser Leu Ser Ala Ser Val Gly Asp Arg Val Thr Ile Thr Cys Gln Ala Ser Gln Asp Ile Ser Asn Tyr Leu Asn Trp Tyr Gln Gln Lys Pro Gly Lys Ala Pro Lys Leu Leu Ile Xaa1 Xaa2 Xaa3 Xaa4 Xaa5 Leu Glu Thr Gly Val Pro Ser Arg Phe Ser Gly Ser Gly Ser Gly Thr Asp Phe Thr Phe Thr Ile Ser Ser Leu Gln Pro Glu Asp Ile Ala Val Tyr Tyr Cys Gln Gln Ser Tyr Ser Xaa6 Leu Ile Thr Phe Gly Gln Gly Thr Arg Leu Glu Ile Lys Arg Thr Val Ala Ala Pro Ser Val (SEQ ID NO: 89), wherein (a) the subsequence Xaa1 Xaa2 Xaa3 Xaa4 Xaa5 is deleted or is Tyr-Asp-Ala-Ser-Asn, and (b) Xaa6 is threonine (Thr) or isoleucine (Ile).

The inventive immunoglobulin light chain polypeptide can include or lack the subsequence Xaa1 Xaa2 Xaa3 Xaa4 Xaa5 at positions 49-53 of SEQ ID NO: 89 when Xaa6 is threonine (Thr) or isoleucine (Ile). When the inventive immunoglobulin light chain polypeptide comprises the subsequence Xaa1 Xaa2 Xaa3 Xaa4 Xaa5, each of Xaa1, Xaa2, Xaa3, Xaa4, and Xaa5 can be any suitable amino acid residue. Preferably, Xaa1 is tyrosine (Tyr), Xaa2 is aspartic acid (Asp), Xaa3 is alanine (Ala), Xaa4 is serine (Ser), and Xaa5 is asparagine (Asn). A preferred amino acid sequence of an immunoglobulin light chain polypeptide which includes the subsequence Xaa1 Xaa2 Xaa3 Xaa4 Xaa5 comprises SEQ ID NO: 90. When the immunoglobulin light chain polypeptide lacks the subsequence Xaa1 Xaa2 Xaa3 Xaa4 Xaa5, the immunoglobulin light chain polypeptide preferably comprises the amino acid sequence SEQ ID NO: 91 or SEQ ID NO: 92.

In another embodiment, provided is an isolated immunoglobulin light chain polypeptide which comprises SEQ ID NO: 196 or 197. Examples of such a polypeptide include those comprising any one of SEQ ID NOs: 198-200.

When the inventive immunoglobulin light chain polypeptide consists essentially of an amino acid sequence of any one of SEQ ID NO: 57-SEQ ID NO: 92, SEQ ID NOs: 187-189, or SEQ ID NOs: 196-200, additional components can be included in the polypeptide that do not materially affect the polypeptide (e.g., protein moieties such as biotin that facilitate purification or isolation). When the inventive immunoglobulin light chain polypeptide consists of an amino acid sequence of any one of SEQ ID NO: 57-SEQ ID NO: 92, the polypeptide does not comprise any additional components (i.e., components that are not endogenous to the inventive immunoglobulin light chain polypeptide).

The invention provides an isolated immunoglobulin light chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to any one of SEQ ID NO: 57-SEQ ID NO: 92, Nucleic acid or amino acid sequence "identity" can be determined using the methods described herein.

One or more amino acids of the aforementioned immunoglobulin heavy chain polypeptides and/or light chain polypeptides can be replaced or substituted with a different amino acid. An amino acid "replacement" or "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring, Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E car Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

The amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —NH$_2$ can be maintained.

"Semi-conservative mutations" include amino acid substitutions of amino acids within the same groups listed above, but not within the same sub-group. For example, the substitution of aspartic acid fir asparagine, or asparagine for lysine, involves amino acids within the same group, but different sub-groups, "Non-conservative mutations" involve amino acid substitutions between different groups, for example, lysine for tryptophan, or phenylalanine for serine, etc.

In addition, one or more amino acids can be inserted into the aforementioned immunoglobulin heavy chain polypeptides and/or light chain polypeptides. Any number of any suitable amino acids can be inserted into the amino acid sequence of the immunoglobulin heavy chain polypeptide and/or light chain polypeptide. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the immunoglobulin heavy chain polypeptide and/or light chain polypeptide. Preferably, 1-10 amino acids (e.g., 1, 2, 3, 4, 5, 6, 7, 8, 9, or 10 amino acids) are inserted into the amino acid sequence of the immunoglobulin heavy chain polypeptide and/or light chain polypeptide. In this respect, the amino acid(s) can be inserted into any one of the aforementioned immunoglobulin heavy chain polypeptides and/or light chain polypeptides in any suitable location. Preferably, the amino acid(s) are inserted into a CDR (e.g., CDR1, CDR2, or CDR3) of the immunoglobulin heavy chain polypeptide and/or light chain polypeptide.

The inventive isolated immunoglobulin heavy chain polypeptide and light chain polypeptides are not limited to polypeptides comprising the specific amino acid sequences described herein. Indeed, the immunoglobulin heavy chain polypeptide or light chain polypeptide can be any heavy chain polypeptide or light chain polypeptide that competes with the inventive immunoglobulin heavy chain polypeptide or light chain polypeptide for binding to LAG-3. In this respect, for example, the immunoglobulin heavy chain polypeptide or light Chain polypeptide can be any heavy chain polypeptide or light chain polypeptide that binds to the same epitope of LAG-3 recognized by the heavy and light chain polypeptides described herein. Antibody competition can be assayed using routine peptide competition assays which utilize ELISA, Western blot, or immunohistochemistry methods (see, e.g., U.S. Pat. Nos. 4,828,981 and 8,568,992; and Braitbard et al., *Proteome Sci.*, 4: 12 (2006)).

The invention provides an isolated LAG-3-binding agent comprising, consisting essentially of, or consisting of one or more of the inventive isolated amino acid sequences described herein. By "LAG-3-binding agent" is meant a molecule, preferably a proteinaceous molecule, which binds specifically to the LAG-3 protein. Preferably, the LAG-3-binding agent is an antibody or a fragment (e.g., immunogenic fragment) thereof. The LAG-3-binding agent of the invention comprises, consists essentially of, or consists of the inventive isolated immunoglobulin heavy chain polypeptide and/or the inventive isolated immunoglobulin light chain polypeptide. In one embodiment, the LAG-3-binding agent comprises, consists essentially of, or consists of the inventive immunoglobulin heavy chain polypeptide or the inventive immunoglobulin light chain polypeptide. In another embodiment, the LAG-3-binding agent comprises, consists essentially of, or consists of the inventive immunoglobulin heavy chain polypeptide and the inventive immunoglobulin light chain polypeptide.

Any amino acid residue of the inventive immunoglobulin heavy chain polypeptide and/or the inventive immunoglobulin light chain polypeptide can be replaced, in any combination, with a different amino acid residue, or can be deleted or inserted, so long as the biological activity of the LAG-3-binding agent is enhanced or improved as a result of the amino acid replacements, insertions, and/or deletions. The "biological activity" of an LAG-3-binding agent refers to, for example, binding affinity for a particular LAG-3 epitope, neutralization or inhibition of LAG-3 binding to its receptor(s), neutralization or inhibition of LAG-3 activity in vivo (e.g., IC$_{50}$), pharmacokinetics, and cross-reactivity (e.g., with non-human homologs or orthologs of the LAG-3 protein, or with other proteins or tissues). Other biological properties or Characteristics of an antigen-binding agent recognized in the art include, for example, avidity, selectivity, solubility, folding, immunotoxicity, expression, and formulation. The aforementioned properties or characteristics can be observed, measured, and/or assessed using standard techniques including, but not limited to, ELISA, competitive ELISA, surface plasmon resonance analysis (BIACORE™), or KINEXA™, in vitro or in vivo neutralization assays, receptor-ligand binding assays, cytokine or growth factor production and/or secretion assays, and signal transduction and immunohistochemistry assays.

The terms "inhibit" or "neutralize," as used herein with respect to the activity of a LAG-3-binding agent, refer to the ability to substantially antagonize, prohibit, prevent, restrain, slow, disrupt, alter, eliminate, stop, or reverse the progression or severity of, for example, the biological activity of LAG-3, or a disease or condition associated with LAG-3. The isolated LAG-3-binding agent of the invention preferably inhibits or neutralizes the activity of LAG-3 by at least about 20%, about 30%, about 40%, about 50%, about 60%, about 70%, about 80%, about 90%, about 95%, about 100%, or a range defined by any two of the foregoing values.

The isolated LAG-3-binding agent of the invention can be a whole antibody, as described herein, or an antibody fragment. The terms "fragment of an antibody," "antibody fragment," and "functional fragment of an antibody" are used interchangeably herein to mean one or more fragments of an antibody that retain the ability to specifically bind to an antigen (see, generally, Holliger et al., *Nat. Biotech.*, 23(9): 1126-1129 (2005)). The isolated LAG-3-binding agent can contain any LAG-3-binding antibody fragment. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the $V_L$, $V_H$, $C_L$, and $CH_1$ domains, (ii) a F(ab+)$_2$ fragment, which is a bivalent fragment comprising two Fab fragments linked by a disulfide bridge at the hinge region, (iii) a fragment consisting of the $V_L$ and $V_H$ domains of a single arm of an antibody, (iv) a Fab' fragment, which results from breaking the disulfide bridge of an F(ab')$_2$ fragment using mild reducing conditions, (v) a disulfide-stabilized Fv fragment (dsFv), and (vi) a domain antibody (dAb), which is an antibody single variable region domain (VH or VL) polypeptide that specifically binds antigen.

In embodiments where the isolated LAG-3-binding agent comprises a fragment of the immunoglobulin heavy chain or light chain polypeptide, the fragment can be of any size so long as the fragment binds to, and preferably inhibits the activity of, LAG-3. In this respect, a fragment of the immunoglobulin heavy chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids. Similarly, a fragment of the immunoglobulin light chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids.

When the LAG-3-binding agent is an antibody or antibody fragment, the antibody or antibody fragment desirably comprises a heavy chain constant region ($F_c$) of any suitable class. Preferably, the antibody or antibody fragment comprises a heavy chain constant region that is based upon wild-type IgG1, IgG2, or IgG4 antibodies, or variants thereof. In some embodiments, the LAG-3 binding agent comprises an Fc region engineered to reduce or eliminate effector functions of the antibody. Engineered Fc regions with reduced or abrogated effector function are known in the art and commercially available, as are techniques for engineering Fc regions to reduce or eliminate effector function, any of which can be used in conjunction with the invention.

The LAG-3-binding agent also can be a single chain antibody fragment. Examples of single chain antibody fragments include, but are not limited to, (i) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain (see, e.g., Bird et al, *Science*, 242: 423-426 (1988); Huston et al., *Proc. Natl. Acad. Sci. USA*, 85: 5879-5883 (1988); and Osbourn et al., *Nat. Biotechnol.*, 16: 778 (1998)) and (ii) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen binding sites. Antibody fragments are known in the art and are described in more detail in, e.g., U.S. Patent Application Publication 2009/0093024 A1.

The isolated LAG-3-binding agent also can be an intrabody or fragment thereof. An intrabody is an antibody which is expressed and which functions intracellularly. Intrabodies typically lack disulfide bonds and are capable of modulating the expression or activity of target genes through their specific binding activity. Intrabodies include single domain fragments such as isolated $V_H$ and $V_L$ domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions.

The isolated LAG-3-binding agent also can be an antibody conjugate. In this respect, the isolated LAG-3-binding agent can be a conjugate of (1) an antibody, an alternative scaffold, or fragments thereof, and (2) a protein or non-protein moiety comprising the LAG-3-binding agent. For example, the LAG-3-binding agent can be all or part of an antibody conjugated to a peptide, a fluorescent molecule, or a chemotherapeutic agent.

The isolated LAG-3-binding agent can be, or can be obtained from, a human antibody, a non-human antibody, or a chimeric antibody. By "chimeric" is meant an antibody or fragment thereof comprising both human and non-human regions. Preferably, the isolated LAG-3-binding agent is a humanized antibody. A "humanized" antibody is a monoclonal antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise one, two, or three CDRs obtained or derived from a non-human antibody. In one embodiment of the invention, CDRH3 of the inventive LAG-3-binding agent is obtained or derived from a mouse monoclonal antibody, while the remaining variable regions and constant region of the inventive LAG-3-binding agent are obtained or derived from a human monoclonal antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein, *Eur. J. Immunol.,* 5: 511-519 (1976); Harlow and Lane (eds.), *Antibodies: A Laboratory Manual,* CSH Press (1988); and Janeway et al. (eds.), *Immunobiology,* 5th Ed., Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, *Nat. Biotechnol.,* 23(9): 1117-25 (2005), and Lonberg, *Handb. Exp. Pharmacal.,* 181: 69-97 (2008)). A humanized antibody can be generated using any suitable method known in the art (see, e.g., An, Z. (ed.), *Therapeutic Monoclonal Antibodies: From Bench to Clinic,* John Wiley & Sons, Inc., Hoboken, N.J. (2009)), including, e.g., grafting of non-human CDRs onto a human antibody scaffold (see, e.g., Kashmiri et al., *Methods,* 36(1): 25-34 (2005); and Hou et al., *J. Biochem.,* 144(1): 115-120 (2008)). In one embodiment, a humanized antibody can be produced using the methods described in, e.g., U.S. Patent Application Publication 2011/0287485 A1.

In one embodiment, a CDR (e.g., CDR1, CDR2, or CDR3) or a variable region of the immunoglobulin heavy chain polypeptide and/or the immunoglobulin light chain polypeptide described herein can be transplanted (i.e., grafted) into another molecule, such as an antibody or non-antibody polypeptide, using either protein chemistry or recombinant DNA technology. In this regard, the invention provides an isolated LAG-3-binding agent comprising at least one CDR of an immunoglobulin heavy chain and/or light chain polypeptide as described herein. The isolated LAG-3-binding agent can comprise one, two, or three CDRs of an immunoglobulin heavy chain and/or light chain variable region as described herein.

In a preferred embodiment, the LAG-3-binding agent binds an epitope of LAG-3 which blocks the binding of LAG-3 to MHC Class II molecules and inhibits LAG-3-mediated signaling. For example, the LAG-3 binding agent can bind to one or more of the four Ig-like extracellular domains (D1-D4) of the LAG-3 protein (see, e.g., Triebel et al., *J. Exp. Med.,* 171(5): 1393-1405 (1990); and Bruniquel et al., *Immunogenetics,* 47: 96-98 (1997)). Preferably, the LAG-3 binding agent binds to domain 1 (D1) and/or domain (D2) of the LAG-3 protein. The invention also provides an isolated or purified epitope of LAG-3 which blocks the binding of LAG-3 to MHC Class II molecules in an indirect or allosteric manner.

The invention also provides one or more isolated or purified nucleic acid sequences that encode the inventive immunoglobulin heavy chain polypeptide, the inventive immunoglobulin light chain polypeptide, and the inventive LAG-3-binding agent.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The invention further provides a vector comprising one or more nucleic acid sequences encoding the inventive immunoglobulin heavy chain polypeptide, the inventive immunoglobulin light chain polypeptide, and/or the inventive LAG-3-binding agent. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual,* 3rd edition, Cold Spring Harbor Press, Cold Spring Harbor, N.Y. (2001), and Ausubel et al., *Current Protocols in Molecular Biology,* Greene Publishing Associates and John Wiley Sons, New York, N.Y. (1994)).

In addition to the nucleic acid sequence encoding the inventive immunoglobulin heavy polypeptide, the inventive immunoglobulin light chain polypeptide, and/or the inventive LAG-3-binding agent, the vector preferably comprises expression control sequences, such as promoters, enhancers, polyadenylation signals, transcription terminators, signal peptides (e.g., the osteonectin signal peptide), internal ribosome entry sites (IRES), and the like, that provide for the expression of the coding sequence in a host cell. Exemplary expression control sequences are known in the art and described in, for example, Goeddel, *Gene Expression Technology: Methods in Enzymology,* Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al., *Proc. Natl. Acad. Sci.,* 93: 3346-3351 (1996)), the T-REX™ system (Invitrogen, Carlsbad, Calif.), LACSWITCH™ system (Stratagene, San Diego, Calif.), and the Cre-ERT tamoxifen inducible recombinase system (Indra et al., *Nuc. Acid. Res.,* 27: 4324-4327 (1999); *Nuc. Acid. Res.,* 28: e99 (2000); U.S. Pat. No. 7,112,715; and Kramer & Fussenegger, *Methods Mol. Biol.,* 308: 123-444 (2005)).

The term "enhancer" as used herein, refers to a DNA sequence that increases transcription of, for example, a nucleic acid sequence to which it is operably linked. Enhancers can be located many kilobases away from the coding region of the nucleic, acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA*, 77: 3567-3570 (1980); O'Hare et al., *Proc. Natl. Acad. Sci. USA*, 78: 1527-1531 (1981); Mulligan & Berg, *Proc. Natl. Acad. Sci. USA*, 78: 2072-2076 (1981); Colberre-Garapin et al., *J. Mol. Biol.*, 150: 1-14 (1981); Santerre et al., *Gene*, 30: 147-156 (1984); Kent et al., *Science*, 237: 901-903 (1987); Wigler et al., *Cell*, 11: 223-232 (1977); Szybalska & Szybalski, *Proc. Natl. Acad Sci. USA*, 48: 2026-2034 (1962); Lowy et al., *Cell*, 22: 817-823 (1980); and U.S. Pat. Nos. 5,122,464 and 5,770, 359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy*, 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Life Technologies (Carlsbad, Calif.), UCOE from Millipore (Billerica, Mass.), and pCI pFN10A (ACT) FLEXI™ from Promega (Madison, Wis.).

Viral vectors also can be used. Representative commercially available viral expression vectors include, but are not limited to, the adenovirus-based Per.C6 system available from Crucell, Inc. (Leiden, The Netherlands), the lentiviral-based pLP1 from Invitrogen (Carlsbad, Calif.), and the retroviral vectors pFB-ERV plus pCFB-EGSH from Stratagene (La Jolla, Calif.).

Nucleic acid sequences encoding the inventive amino acid sequences can be provided to a cell on the same vector (i.e., in cis). A unidirectional promoter can be used to control expression of each nucleic acid sequence. In another embodiment, a combination of bidirectional and unidirectional promoters can be used to control expression of multiple nucleic acid sequences. Nucleic acid sequences encoding the inventive amino acid sequences alternatively can be provided to the population of cells on separate vectors (i.e., in trans). Each of the nucleic acid sequences in each of the separate vectors can comprise the same or different expression control sequences. The separate vectors can be provided to cells simultaneously or sequentially.

The vector(s) comprising the nucleic acid(s) encoding the inventive amino acid sequences can be introduced into a host cell that is capable of expressing the polypeptides encoded thereby, including any suitable prokaryotic or eukaryotic cell. As such, the invention provides an isolated cell comprising the inventive vector. Preferred host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas*, *Streptomyces*, *Salmonella*, and *Erwinia*. Particularly useful prokaryotic cells include the various strains of *Escherichia coli* (e.g., K12, HB101 (ATCC No. 33694), DH5α, DH10, MC1061 (ATCC No. 53338), and CC102).

Preferably, the vector is introduced into a eukaryotic cell. Suitable eukaryotic cells are known in the art and include, for example, yeast cells, insect cells, and mammalian cells. Examples of suitable yeast cells include those from the genera *Kluyveromyces, Pichia, Rhinosporidium, Saccharomyces,* and *Schizosaccharomyces*. Preferred yeast cells include, for example, *Saccharomyces cerivisae* and *Pichia pastoris*.

Suitable insect cells are described in, for example, Kitts et al., *Biotechniques*, 14: 810-817 (1993); Lucklow, *Curr. Opin. Biotechnol.*, 4: 564-572 (1993); and Lucklow et al., *J. Virol.*, 67: 4566-4579 (1993). Preferred insect cells include Sf-9 and H15 (invitrogen, Carlsbad, Calif.).

Preferably, mammalian cells are utilized in the invention. A number of suitable mammalian host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al., *Proc. Natl. Acad. Sci. USA*, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

In one embodiment, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), (CRL-2111), 18-81 (Jack et al., *Proc. Natl. Acad Sci. USA*, 85: 1581-1585 (1988)), Raji cells (CCL-86), PER.C6 cells (Crucell Holland B. V., Leiden, The Netherlands), and derivatives thereof.

A nucleic acid sequence encoding the inventive amino acid sequence may be introduced into a cell by "transfection," "transformation," or "transduction," "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., *Mol. Cell Biol.,* 7: 2031-2034 (1987)). Phage or viral vectors can be introduced into host cells, after growth of infectious particles in suitable packaging cells, many of which are commercially available.

The invention provides a composition comprising an effective amount of the inventive immunoglobulin heavy chain polypeptide, the inventive immunoglobulin light chain polypeptide, the inventive LAG-3-binding agent, the inventive nucleic acid sequence encoding any of the foregoing, or the inventive vector comprising the inventive nucleic acid sequence. Preferably, the composition is a pharmaceutically acceptable (e.g., physiologically acceptable) composition, which comprises a carrier, preferably a pharmaceutically acceptable (e.g., physiologically acceptable) carrier, and the inventive amino acid sequences, antigen-binding agent, or vector. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: *The Science and Practice of Pharmacy, 21st Edition*, Lippincott Williams & Wilkins, Philadelphia, Pa. (2001).

The invention further provides a method of treating a disorder in a mammal that is responsive to LAG-3 inhibition or neutralization. The method comprises administering the aforementioned composition to a mammal having a disorder that is responsive to LAG-3 inhibition or neutralization, whereupon the disorder is treated in the mammal. A disorder that is "responsive to LAG-3 inhibition" or "responsive to LAG-3 neutralization" refers to any disease or disorder in which a decrease in LAG-3 levels or activity has a therapeutic benefit in mammals, preferably humans, or the improper expression (e.g., overexpression) or increased activity of LAG-3 causes or contributes to the pathological effects of the disease or disorder. Disorders that are responsive to LAG-3 inhibition include, for example, cancer and infectious diseases. The inventive method can be used to treat any type of cancer known in the art, such as, for example, melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, or Merkel cell carcinoma (see, e.g., Bhatia et al., *Curr. Oncol. Rep.,* 13(6): 488-497 (2011)). The inventive method can be used to treat any type of infectious disease (i.e., a disease or disorder caused by a bacterium, a virus, a fungus, or a parasite). Examples of infectious diseases that can be treated by the inventive method include, but are not limited to, diseases caused by a human immunodeficiency virus (HIV), a respiratory syncytial virus (RSV), an influenza virus, a dengue virus, a hepatitis B virus (HBV, or a hepatitis C virus (HCV)). Administration of a composition comprising the inventive immunoglobulin heavy chain polypeptide, the inventive immunoglobulin light chain polypeptide, the inventive LAG-3-binding agent, the inventive nucleic acid sequence encoding any of the foregoing, or the inventive vector comprising the inventive nucleic acid sequence induces an immune response against a cancer or infectious disease in a mammal. An "immune response" can entail, for example, antibody production and/or the activation of immune effector cells (e.g., T-cells).

As used herein, the terms "treatment" "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the LAG-3-binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the LAG-3-binding agent to elicit a desired response in the individual. For example, a therapeutically effective amount of a LAG-3-binding agent of the invention is an amount which decreases LAG-3 bioactivity in a human.

Alternatively, the pharmacologic and/or physiologic effect may be prophylactic, i.e., the effect completely or partially prevents a disease or symptom thereof. In this respect, the inventive method comprises administering a "prophylactically effective amount" of the LAG-3-binding agent. A "prophylactically effective amount" refers to an amount effective, at dosages and for periods of time necessary, to achieve a desired prophylactic result (e.g., prevention of disease onset).

A typical dose can be, for example, in the range of 1 pg/kg to 20 mg/kg of animal or human body weight; however, doses below or above this exemplary range are within the scope of the invention. The daily parenteral dose can be about 0.00001 µg/kg to about 20 mg/kg of total body weight (e.g., about 0.001 µg/kg, about 0.1 µg/kg, about 1 µg/kg, about 5 µg/kg, about 10 µg/kg, about 100 µg/kg, about 500 µg/kg, about 1 mg/kg, about 5 mg/kg, about 10 mg/kg, or a range defined by any two of the foregoing values), preferably from about 0.1 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 5 mg/kg of total body weight (e.g., about 3 µg/kg, about 15 µg/kg, about 75 µg/kg, about 300 µg/kg, about 900 µg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising an effective amount of the inventive immunoglobulin heavy chain polypeptide, the inventive immunoglobulin light chain polypeptide, the inventive LAG-3-binding agent, the inventive nucleic acid sequence encoding any of the foregoing, or the inventive vector comprising the inventive nucleic acid sequence can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a cross-reactive human), the biological activity of the inventive LAG-3-binding agent can be measured by any suitable method known in the art. For example, the biological activity can be assessed by determining the stability of a particular LAG-3-binding agent. In one embodiment of the invention, the LAG-3-binding agent (e.g., an antibody) has an in vivo half life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values). In another embodiment, the LAG-3-binding agent has an in vivo half life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In another embodiment, the LAG-3-binding agent has an in vivo half life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values).

The biological activity of a particular LAG-3-binding agent also can be assessed by determining its binding affinity to LAG-3 or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 picomolar (pM) to about 100 micromolar (μM) (e.g., from about 1 picomolar (pM) to about 1 nanomolar (nM), from about 1 nM to about 1 micromolar (μM), or from about 1 μM to about 100 μM). In one embodiment, the LAG-3-binding agent can bind to an LAG-3 protein with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the LAG-3-binding agent can bind to LAG-3 with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, and/or ELISA (see, e.g., Janeway et al, (eds.), *Immunobiology*, 5th ed., Garland Publishing, New York, N.Y., 2001).

The LAG-3-binding agent of the invention may be administered alone or in combination with other drugs (e.g., as an adjuvant). For example, the LAG-3-binding agent can be administered in combination with other agents for the treatment or prevention of the diseases disclosed herein. In this respect, the LAG-3-binding agent can be used in combination with at least one other anticancer agent including, for example, any chemotherapeutic agent known in the art, ionization radiation, small molecule anticancer agents, cancer vaccines, biological therapies (e.g., other monoclonal antibodies, cancer-killing viruses, gene therapy, and adoptive T-cell transfer), and/or surgery. When the inventive method treats an infectious disease, the LAG-3-binding agent can be administered in combination with at least one anti-bacterial agent or at least one anti-viral agent. In this respect, the anti-bacterial agent can be any suitable antibiotic known in the art. The anti-viral agent can be any vaccine of any suitable type that specifically targets a particular virus (e.g., live-attenuated vaccines, subunit vaccines, recombinant vector vaccines, and small molecule anti-viral therapies (e.g., viral replication inhibitors and nucleoside analogs).

In another embodiment, the inventive LAG-3 binding agent can be administered in combination with other agents that inhibit immune checkpoint pathways. For example, the inventive LAG-3 binding agent can be administered in combination with agents that inhibit or antagonize the programmed death 1 (PD-1), T-cell immunoglobulin domain and mucin domain 3 protein (TIM-3), and cytotoxic I-lymphocyte-associated protein 4 (CTLA-4) pathways. Combination treatments that simultaneously target two or more of these immune checkpoint pathways have demonstrated improved and potentially synergistic antitumor activity (see, e.g., Sakuishi et al., *J. Exp. Med.*, 207: 2187-2194 (2010); Ngiow et al., *Cancer Res.*, 71: 3540-3551 (2011); and Woo et al., *Cancer Res.*, 72: 917-927 (2012)). In one embodiment, the inventive LAG-3 binding agent is administered in combination with an antibody that binds to TIM-3 and/or an antibody that binds to PD-1. In this respect, the inventive method of treating a cancer or an infectious disease in a mammal can further comprise administering to the mammal a composition comprising (i) an antibody that binds to a TIM-3 protein and (ii) a pharmaceutically acceptable carrier or a composition comprising (i) an antibody that binds to a PD-1 protein and (ii) a pharmaceutically acceptable carrier.

In addition to therapeutic uses, the LAG-3-binding agent described herein can be used in diagnostic or research applications. In this respect, the LAG-3-binding agent can be used in a method to diagnose a disorder or disease in which the improper expression (e.g., overexpression) or increased activity of LAG-3 causes or contributes to the pathological effects of the disease or disorder. In a similar manner, the LAG-3-binding agent can be used in an assay to monitor LAG-3 protein levels in a subject being tested for a disease or disorder that is responsive to LAG-3 inhibition. Research applications include, for example, methods that utilize the LAG-3-binding agent and a label to detect an LAG-3 protein in a sample, e.g., in a human body fluid or in a cell or tissue extract. The LAG-3-binding agent can be used with or without modification, such as covalent or non-covalent labeling with a detectable moiety. For example, the detectable moiety can be a radioisotope (e.g., $^3H$, $^{14}C$, $^{32}P$, $^{35}S$, or $^{125}I$), a fluorescent or chemiluminescent compound (e.g., fluorescein isothiocyanate, rhodamine, luciferin), an enzyme (e.g., alkaline phosphatase, beta-galactosidase, or horseradish peroxidase), or prosthetic groups. Any method known in the art for separately conjugating an antigen-binding agent (e.g., an antibody) to a detectable moiety may be employed in the context of the invention (see, e.g., Hunter et al., *Nature*, 194: 495-496 (1962); David et al., *Biochemistry*, 13: 1014-1021 (1974); Pain et al. *J. Immunol. Meth.*, 40: 219-230 (1981); and Nygren, *J. Histochem. and Cytochem.*, 30: 407-412 (1982)).

LAG-3 protein levels can be measured using the inventive LAG-3-binding agent by any suitable method known in the art. Such methods include, for example, radioimmunoassay (RIA), and FACS. Normal or standard expression values of LAG-3 can be established using any suitable technique, e.g., by combining a sample comprising, or suspected of comprising, LAG-3 with a LAG-3-specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques*, CRC Press, Inc. (1987)). The amount of LAG-3 polypeptide expressed in a sample is then compared with a standard value.

The LAG-3-binding agent can be provided in a kit, i.e., a packaged combination of reagents in predetermined amounts with instructions for performing a diagnostic assay. If the LAG-3-binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

The following examples further illustrate the invention but, of course, should not be construed as in any way limiting its scope.

Example 1

This example demonstrates a method of generating monoclonal antibodies directed against human LAG-3.

The gene encoding the extracellular domain (ECD) of human LAG-3 was fused to either mouse IgG2a (human LAG-3 mIgG2a Fc) or a disabled form of wasabi fluorescent protein (dWFP human LAG-3) to produce antigen for use in mouse immunization and hybridoma screening. Specifically, female Swiss Webster (SWR) mice were purchased from Harlan Laboratories, Inc. (Indianapolis, Ind.) and divided into two groups. After six days of acclimatization, one group of animals was immunized with four to six doses of purified human LAG-3 mIgG2a Fc at 50 µg/mouse at intervals of three to four weeks using complete Freund's adjuvant (CFA) or incomplete Freunds adjuvant (IFA). The second group of animals was injected with four to six doses at intervals of three to four weeks alternating between human LAG-3 mIgG2a Fc or dWFP human LAG-3 ECD. CFA or IFA was also used as adjuvant in the second group. Animals were bled for measurement of the serum titer to human LAG-3 as assessed by binding to cell surface human LAG-3. CHO-S cells were transfected with a full length human LAG-3 extracellular domain fused to the H-2Kk transmembrane domain (CHO-S huLAG-3 ECD cells). Sera were diluted from 1:1,000-1:1,000,000 and incubated with the CHO-S huLAG-3 ECD cells for 30 minutes at 4° C. Cells were centrifuged, washed once with PBS/1% BSA, and incubated with RE-conjugated (Southern biotech, Birmingham, Ala.) or ALEXAFLUOR™ 647-(Jackson Immunoresearch, West Grove, Pa.) labeled goat anti-mouse IgG (H+L) for 30 minutes at 4° C. Cells were washed twice in PBS/1% BSA, resuspended in PBS/1% BSA, and analyzed on a BD FAC-SARRAY™ Bioanalyzer (BD Biosciences, Franklin Lakes, N.J.). Based on titer readings, one animal from each group was boosted 3 days prior to spleen collection. Single cell suspensions were prepared from spleen tissue and used for generation of hybridomas by cell fusion using standard techniques. Two different myeloma cell lines were used for fusion, F0 (described in de St. Groth and Scheidegger, *J. Immunol. Methods*, 35: 1-21 (1980)) and P3X63Ag8.653 (described in Kearney et al., *J. Immunol.*, 123: 1548-1550 (1979)).

Hybridoma supernatants were screened for binding to CHO-S huLAG-3 ECD cells and compared to binding to untransfected CHO-S cells as described above. Based upon binding CHO-S huLAG-3 ECD cells, hybridomas were transferred to 48-well plates and expanded.

Supernatants were then tested for the ability to block binding of human LAG-3 mIgG2a Fc labeled with DyL650 (human LAG-3 mIgG2a Fc DyL650) to Daudi cells, which is a B-cell line that endogenously expresses high levels of MHCII (the LAG-3 receptor). Briefly, human LAG-3 mIgG2a Fc DyL650 was pre-incubated with control IgG or anti-human LAG-3 candidate monoclonal antibodies prior to addition to Daudi cells. Blocking was measured by reduction in fluorescence to Daudi cells using a BD FAC-SARRAY™ Bioanalyzer. These hybridomas were then subcloned and expanded to plate for generation of exhaust supernatant. Antibodies were subsequently purified and retested to confirm both binding to CHO-S huLAG-3 ECD cells and blocking ability in the Daudi assay.

The results of this example confirm the production of anti-LAG-3 monoclonal antibodies using hybridoma cell technology.

Example 2

This example describes the design and generation of CDR-grafted and chimeric anti-LAG-3 monoclonal antibodies.

Antibodies from the hybridomas described in Example 1 were isotyped, subjected to RT-PCR for cloning the antibody heavy chain variable region ($V_H$) and light chain variable region ($V_L$), and sequenced. Specifically, RNA was isolated from cell pellets of hybridoma clones ($1 \times 10^6$ cells/pellet) using the RNEASY™ kit (Qiagen, Venlo, Netherlands), and cDNA was prepared using oligo-dT-primed SUPERSCRIPT™ III First-Strand Synthesis System (Life Technologies, Carlsbad, Calif.). PCR amplification of the $V_L$ utilized a pool of degenerate mouse $V_L$ forward primers (see Kontermann and Rubel, eds., Antibody Engineering, Springer-Verlag, Berlin (2001)) and a mouse κ constant region reverse primer. PCR amplification of the $V_H$ utilized a pool of degenerate mouse $V_H$ forward primers (Kontermann and Dubel, supra) and a mouse γ1 or γ2a constant region reverse primer (based on isotyping of purified antibody from each clone) with the protocol recommended in the SUPERSCRIPT™ III First-Stand Synthesis System (Life Technologies, Carlsbad, Calif.). PCR products were purified and cloned into pcDNA3.3-TOPO (Life Technologies, Carlsbad, Calif.).

Individual colonies from each cell pellet were selected and sequenced using standard Sanger sequencing methodology (Genewiz, Inc., South Plainfield, N.J.). Variable region sequences were examined and aligned with the closest human heavy chain or light chain V-region germline sequence. Three antibodies were selected for CDR-grafting, which were denoted (1) 5.B11, (2) 5.D7, and (3) 1.E10.

CDR-grafted antibody sequences were designed by cloning CDR residues from each of the above-described mouse antibodies into the closest human germline homolog. CDR-grafted antibody variable regions were synthesized and expressed with human IgG1/κ constant regions for analysis. In addition, mouse:human chimeric antibodies were constructed using the variable regions of the above-described mouse antibodies linked to human IgG1/κ constant regions. Chimeric and CDR-grafted antibodies were characterized for binding to CHO-S huLAG-3 ECD cells and for activity in the human LAG-3 ECD/Daudi blocking assay as described above.

The functional antagonist activity of chimeric and CDR-grafted antibodies also was tested in a human CD4' T-cell: dendritic cell mixed lymphocyte reaction (MLR) assay in which activation of $CD4^+$ T-cells in the presence of anti-LAG-3 antibodies is assessed by measuring IL-2 secretion. Because LAG-3 is a negative regulator of T-cell function, antagonism of LAG-3 was expected to result in increased T-cell activation as measured by increased IL-2 production. The 5.B11, 5.D7, and 1.E10 CDR-grafted antibodies demonstrated antagonistic activity in the MLR, assay as measured by an increase in IL-2 activity.

The results of this example demonstrate a method of generating chimeric and CDR-grafted monoclonal antibodies that specifically bind to and inhibit LAG-3.

Example 3

This example demonstrates affinity maturation of humanized monoclonal antibodies directed against human LAG-3.

CDR-grafted antibodies derived from two of the original murine monoclonal antibodies described in Example 2, 5.D7 and 1.E10, were subjected to affinity maturation via in silico somatic hypermutation (iSHM). This method incorporates mutations as predicted by computational analysis comparing in vivo matured antibody sequences, as downloaded from NCBI, and comparing them to germline human IGHV, IGKV, and IGLV sequences and their allelic forms (as described in Bowers et al., J. Biol. Chem., 288(11):7688-7696 (2013)). The LAG-3 binding properties of resultant antibodies were assayed using surface plasmon resonance (SPR) as well as ability to bind to CHO-S huLAG-3 ECD cells as described previously. Solution-based affinity analyses were also performed on using a KINEXA™ 3000 assay (Sapidyne Instruments, Boise, Id.), and results were analyzed using KINEXA™ Pro Software 3.2.6. Experimental parameters were selected to reach a maximum signal with antibody alone between 0.8 and 1.2 V, while limiting non-specific binding signal with buffer alone to less than 10% of the maximum signal. Azlactone beads (50 mg) were coated with antigen by diluting in a solution of human or cynoWFP-LAG-3 (50 µg/mL in 1 mL) in 50 mM $Na_2CO_3$. The solution was rotated at room temperature for 2 hours, and beads were pelleted in a picofuge and washed twice with blocking solution (10 mg/mL, BSA, 1 M Tris-HCl, pH 8.0). Beads were resuspended in blocking solution (1 mL), rotated at room temperature for 1 hour, and diluted in 25 volumes PBS/0.02% $NaN_3$. For affinity measurement, the secondary antibody was ALEXFLUOR™ 647 dye-anti-human IgG (500 ng/mL). Sample antibody concentrations were held constant (50 pM or 75 pM), while human or cynomolgus WFP-LAG-3 antigen was titrated using a three-fold dilutions series from 1 µM to 17 pM. All samples were diluted in PBS, 0.2% $NaN_3$, 1 mg/mL BSA and allowed to equilibrate at room temperature for 30 hours. Additionally, samples containing only antibody and only buffer were tested in order to determine maximum signal and nonspecific binding signal, respectively.

Thermal stability of the selected antibodies was assessed using a Thermofluor assay as described in McConnell et al., Protein Eng. Des. Sel., 26: 151 (2013). This assay assesses stability through the ability of a hydrophobic fluorescent dye to bind to hydrophobic patches on the protein surface which are exposed as the protein unfolds. The temperature at which 50% of the protein unfolds (Tm) is determined to measure thermal stability. This assay demonstrated that 5.D7 monoclonal antibody variants had acceptable melting temperatures ($T_m$s) (i.e., greater than 70° C.) that were suitable for drug development.

De-risking of potential issues related to in vivo pharmokinetics of the tested antibodies was undertaken through assessment of non-specific binding to target negative cells (see, e.g., Hotzel et al., mAbs, 4: 753-760 (2012)). Antibodies were tested for binding to HEK 293f cells using a flow cytometry-based assay. The results indicated that non-specific binding was low for 5.D7 and could be further eliminated through second step purification.

The results of this example confirm a method of affinity maturing humanized monoclonal antibodies directed against LAG-3.

Example 4

This example demonstrates a method of identifying antibodies directed against human LAG-3 from an evolvable library.

An IgG evolvable library, based on germline sequence V-gene segments joined to human donor-derived recombined (D) J regions, was constructed as described in Bowers et al. Proc. Natl. Acad. Sci. USA, 108(51): 20455-20460

(2011). IgG heavy chain (HC) and light chain (LC) were cloned into separate episomal vectors (Horlick et al., *Gene*, 243(1-2): 187-194 (2000)), with each vector encoding a distinct antibiotic selectable marker. The HC vector was formatted such that antibody was presented both on the cell surface as well as secreted into the tissue culture medium (Horlick et al., *J. Biol. Chem.*, 288(27): 19861-19869 (201)). The diverse sets of HCs and LCs were co-transfected into HEK293 cells and expanded to approximately $10^9$ cells. The cell library was then subjected to two rounds each of negative selection against streptavidin (SA)-coupled magnetic beads alone (catalog #11047, Life Technologies, Carlsbad, Calif.) and irrelevant biotinylated antigen coated with SA-coupled magnetic beads. One round of positive selection was then performed using either magnetic beads coated directly with human LAG-3 mIgG2a Fc or with SA-coupled magnetic beads coated with biotinylated LAG-3 ECD mIgG1 Fc. The positively selected cells were diluted and plated in 96-well format at an approximate density of 1-10 cells/well. Resulting colonies were expanded into daughter plates and a portion of each population was tested for binding to LAG-3 ECD mIgG1 DyL650 by FACSARRAY™ analysis. Antibodies secreted into the supernatant also were tested by BIACORE™ for ability to bind to LAG-3 ECD mIgG1 Fc.

Cells that showed specific staining to human LAG-3 mIgG2a Fc DyL650 by FACSARRAY™ analysis and/or binding by BIACORE™ were expanded for sorting and submitted for sequencing to recover the specific HC/LC combinations capable of binding to human LAG-3. The open reading frames (ORFs) encoding the HCs and LCs of the antibodies found in the cell populations were rescued by PCR. Generally, multiple HC/LC sequences were found by sequencing. In some cases the desired HC/LC combinations were identified by enriching cells expressing monoclonal antibodies of interest by first FACS sorting with human LAG-3 mIgG2a Fc DyL650. Populations of cells exhibiting high antibody expression and positive for binding to human LAG-3 mIgG2a Fc DyL650 were isolated and subjected to subsequent sequence analysis. Overall, 12 different HC/LC pairs were identified as potential specific anti-LAG-3 antibody hits suitable for further characterization. These strategies were labeled A1/A14, A2, A3/A17, A4/A19, A5/A16, A6, A8/A20, A9, A10/A15, A11, A12, and A13.

Antibodies also were characterized for their ability to bind to cynomolgus monkey LAG-3 protein (cyno LAG-3). As these germline antibodies identified from the library were too weak to bind to antigen expressed on the cell surface, soluble antigen similar to the human antigen was labeled with DyL650 (cyno LAG-3 mIgG2a Fc DyL650) and then incubated with HEK293 cells displaying antibody strategies on the cell surface. Eight antibody strategies identified from the evolvable library were tested and demonstrated an ability to bind to cyno LAG-3 ECD mIgG1 Fc.

The results of this example confirm that monoclonal antibodies directed against human and non-human LAG-3 can be identified using an evolvable library.

Example 5

This example demonstrates affinity maturation of antibodies directed against human LAG-3 identified using an evolvable library.

Stable cell lines co-expressing the HC and LC of each antibody identified from the evolvable library described in Example 4 were transfected with activation induced cytidine deaminase (AID) to initiate in vitro SHM. AID was also transfected directly into the original mixed population of cells expanded from the library screen. In all cases, cell populations were stained for both IgG expression and binding to antigen, collected by flow cytometry as a bulk population, and then expanded for sequence analysis by next generation sequencing (NGS). This process was repeated iteratively to accumulate SHM-derived mutations in the variable regions of both the heavy and light chains, and their derivatives, for each strategy. Improvements in affinity were monitored by (1) SPR, (2) ability to bind to CHO-S huLAG-3 ECD cells, and (3) activity in the MLR assay. As the affinity of each antibody improved, the stringency of selection was increased until affinity goals were achieved through the identification and recombination of novel mutations.

Thermal stability of the selected antibodies was assessed using a Thermofluor assay as described above. This assay demonstrated that select monoclonal antibodies from the A17 strategy had acceptable $T_m$s that were suitable for drug development. Antibodies also were tested for binding to HEK 293f cells using a flow cytometry-based assay. The results indicated that non-specific binding was low for select A17 candidates.

Selected antibodies were tested for the ability to block binding of human LAG-3 mIgG2a Fc labeled with DyL650 (human LAG-3 mIgG2a Fc DyL650) to Daudi cells, as described above. A dose range of neutralizing antibodies was preincubated with the soluble LAG-3 and analyzed by flow cytometry. Certain affinity-matured anti-LAG-3 antibodies completely inhibited the interaction of soluble LAG-3 with MHCII.

The results of this example confirm a method of affinity maturing monoclonal antibodies directed against LAG-3 identified using an evolvable library.

Example 6

This example demonstrates that an inventive anti-LAG-3 monoclonal antibody can inhibit LAG-3 signaling and enhance T-cell activation in vitro alone and in combination with an anti-PD-1 antibody or an anti-TIM-3 antibody.

To establish parameters for anti-LAG-3 and anti-PD-1 combination studies, the anti-PD-1 antibody APE02058 was titrated in a dose-response in the human CD4+ T-cell MLR assay described above. Based on the results from titrating the anti-PD-1 antibody in multiple MLR assays, 133 pM (approximate EC50) and 13 pM (approximate EC10) were selected for testing in combination for antagonist studies with the anti-LAG-3 monoclonal antibody. In combination with 133 pM or 133 pM of anti PD-1, the EC50 of the anti-LAG-3 monoclonal antibody decreased from 690 pM (anti-LAG-3 only) to 40 pM (+133 pM anti-PD-1) or 200 pM (+13.3 pM anti-PD-1), which was a 17-fold and 3-fold increase in potency, respectively.

To establish parameters for anti-LAG-3 and anti-TIM-3 combination studies, the anti-LAG-3 antibody APE05505 was titrated in a dose response in the human CD4+ T-cell MLR assay described above. Based on the results from titrating the anti-LAG-3 antibody in multiple MLR assays, 2 nM (approximate EC50) and 0.2 nM (approximate EC10) were selected for testing in combination for antagonist studies with the anti-TIM-3 monoclonal antibody. In combination with 2 nM or 0.2 nM of anti LAG-3, the EC50 of the anti-LAG-3 mAb decreased from 11 nM (anti-LAG-3 only) to 6 nM (+0.2 nM anti-TIM-3) or 3 nM (+2 nM anti-TIM-3), which was a 1.8-fold and 3.6-fold increase in potency, respectively.

The results of this example demonstrate that the inventive LAG-3 binding agent can inhibit LAG-3 biological activity alone and in combination with antagonists of other negative regulators of the immune system.

Example 7

This example demonstrates that an inventive anti-LAG-3 monoclonal antibody can inhibit LAG-3 signaling and enhance T-cell activation in vivo in combination with an anti-PD-1 antibody.

The activity of an anti-mouse LAG-3 surrogate monoclonal antibody (mAb C9B7W, BioXcell, West Lebanon, N.H.) was tested alone or in combination with an anti-mouse PD-1 surrogate monoclonal antibody (mAb RMP1-14, BioXcell, West Lebanon, N.H.) in the MC38 syngeneic tumor model. Groups of ten animals were injected subcutaneously with $1 \times 10^6$ MC38 cells. Ten days after inoculation, animals were randomized for tumor size. Mice were treated with 5 mg/kg of anti-PD-1 monoclonal antibody and/or 10 mg/kg or anti-LAG-3 monoclonal antibody on days 1, 4, 8, and 11, totaling four doses of each antibody or combination of antibodies. Tumors were measured twice weekly to assess response to treatment. The anti-PD-1+anti-LAG-3 combination was more efficacious in reducing tumor growth than each single agent alone. Complete response was observed in all ten animals of the group treated with the combination, as compared to seven animals in the PD-1-only group and no animals in the anti-LAG-3-only group. Nine animals showing a complete response from the combination group were then rechallenged by subcutaneous innoculation with $4 \times 10^6$ MC38 cells. None of the animals in the rechallenged group developed measurable tumor, while all control naive mice injected with the same amount of cells grew palpable tumor.

The activities of the surrogate monoclonal antibodies described above also were tested alone or in combination in the Colon26 syngeneic tumor model. Groups of 12 animals were injected subcutaneously with $5 \times 10^5$ Colon26 cells. Mice were treated with 10 mg/kg of anti-PD-1 antibody and/or 10 mg/kg of anti-LAG-3 antibody on days 4, 7, 11, and 14, totaling four doses of each antibody or combination of antibodies. Tumors were measured twice weekly to assess response to treatment. The anti-PD-1+anti-LAG-3 combination was more efficacious for tumor growth than each single agent alone. Complete response was observed in 10 out of 12 animals in the combination group, as compared to three animals in the PD-1-only group and one animal in the anti-LAG-3-only group. Nine animals showing complete response from the combination group were then rechallenged with $5 \times 10^5$ Colon26 cells. None of the animals in the rechallenged group developed measurable tumor, while all the control naive mice injected with the same amount of cells grew palpable tumor.

The results of this example demonstrate that the inventive LAG-3 binding agent, in combination with antagonists of other negative regulators of the immune system, can inhibit LAG-3 biological activity in vivo.

Example 8

This example demonstrates the effect of antibody isotype on anti-tumor activity of an anti-LAG-3 antibody alone or in combination with an anti-PD-1 antibody in a syngeneic mouse tumor model.

Surrogate antibodies recognizing mouse LAG-3 of IgG1 (D265A) and IgG2a isotypes were created after sequencing and cloning the variable regions of an anti-mouse LAG-3 neutralizing antibody (mAb C9B7W, BioXcell, West Lebanon, N.H.) from a rat hybridoma cell line and cloning into a mouse or mouse IgG2a expression vector. These antibodies were then tested for efficacy both alone and in combination with a mouse IgG1 (D265A) surrogate antibody recognizing mouse PD-1, similarly created from a purchased rat antibody from BioXcel (mAb RMP1-14, West Lebanon, N.H.). Specifically, Colon26 colon adenocarcinoma cells ($5 \times 10^5$ s.c.) were implanted into Balb/c mice and grown for 3 days. Mice were randomized into seven groups of 12 animals/group and dosed with each antibody or antibody combination on days 4, 7, 11, and 14 as set forth in Table 1. Mice injected with matched isotype antibodies served as a control. Tumor volumes were measured twice weekly until the end of the study.

TABLE 1

| Group | Treatment | Dose |
| --- | --- | --- |
| 1 | Isotype IgG2a + Isotype IgG1(D265A) | 10 mg/kg, 1 mg/kg |
| 2 | Isotype IgG1 (D265A) | 10 mg/kg |
| 3 | Anti-mPD-1 IgG1(D265A) | 1 mg/kg |
| 4 | Anti-mLAG-3 IgG2a | 10 mg/kg |
| 5 | Anti-mLAG-3 IgG1(D265A) | 10 mg/kg |
| 6 | Anti-mPD-1 IgG1(D265A) + Anti-mLAG-3 IgG2a | 1 mg/kg, 10 mg/kg |
| 7 | Anti-mPD-1 IgG1(D265A) + Anti-mLAG-3 IgG1(D265A) | 1 mg/kg, 10 mg/kg |

Results for this experiment are shown in FIGS. 1A and 1B, which show that a single-agent anti-mouse LAG-3 antibody with minimal effector function (i.e., IgG1 (D265A)) has anti-tumor efficacy as compared with an anti-mouse LAG-3 antibody with effector function (i.e., IgG2a), which has no apparent effect on tumor growth.

In addition, FIG. 1A shows an anti-mouse LAG-3 antibody with minimal effector function (i.e., IgG1(D265A)) in combination with a regimen of an anti-mouse PD-1 IgG1 (D265A) antibody exhibited increased anti-tumor activity compared with the anti-mouse PD-1 IgG1(D265A) antibody alone. However, an anti-mouse LAG-3 antibody with in-tact effector function (IgG2a) in combination with an anti-mouse PD-1 antibody was less efficacious than anti-mouse PD-1 IgG1 (D265A) alone, suggesting that the effector function of the antibody possibly interfered with anti-mouse PD-1 mediated efficacy.

FIG. 1B provides graphs of tumor volume over time for individual animals from treatment group 3 (anti-mouse PD-1 IgG1(D265A) antibody treated animals), group 7 (combination of anti-mouse PD-1 IgG1(D265A) antibody with anti-mouse LAG-3 IgG1(D265A) antibody), and group 6 (combination of anti-mouse PD-1 IgG1(D265A) antibody with anti-mouse LAG-3 IgG2 antibody). In group 7 (anti-mouse PD-1 IgG1(D265A) antibody with anti-mouse LAG-3 IgG1 (D265A)), 8/12 animals had no visible tumor growth by the end of the study. By contrast, only 3/12 animals in group 6 (anti-mouse PD-1 IgG1(D265A) antibody with anti-mouse LAG-3 IgG2 antibody) had no visible tumor by the end of the study. In group 3 (anti-mouse PD-1 IgG1 (D265A) alone), 6/12 animals were tumor free by the end of study, suggesting possible interference by the effector function of the anti-mouse LAG-3 IgG2 antibody when dosed in combination with the anti-mouse PD-1 IgG1 (D265A) antibody.

The results of this example demonstrate that anti-mouse LAG-3 and anti-mouse PD-1 antibodies without effector function, alone and in combination, can inhibit tumor growth in a mouse syngeneic tumor model. Efficacy was not observed using an anti-mouse LAG-3 antibody with effector function and furthermore may interfere with anti-PD-1 mediated efficacy.

Example 9

This example demonstrates that an inventive anti-LAG-3 monoclonal antibody inhibitory activity can be differentiated from that of an anti-PD-1 monoclonal antibody in a mixed lymphocyte reaction based upon time of harvest and correlates with PD-1 and LAG-3 expression.

A functional LAG-3 antagonist antibody was tested in a human CD4+ T-cell mixed lymphocyte reaction (MLR) assay in which activation of CD4+ T-cells in the presence of anti-LAG-3 antibodies is assessed by measuring IL-2 secretion. The anti-LAG-3 antibody was tested side by side with an antagonistic anti-PD-1 antibody, wherein the antibodies were added and/or harvested at different timepoints. Specifically, isolated peripheral blood monocytes from a human donor were differentiated into dendritic cells (DCs) and then mixed with CD4+ T-cells isolated from a second donor. Inhibitory antibodies were added either at the start of the co-culture or 24 hours after the start of the co-culture. IL-2 levels were measured at 24 and 48 hours after antibody addition.

Figure 2A:
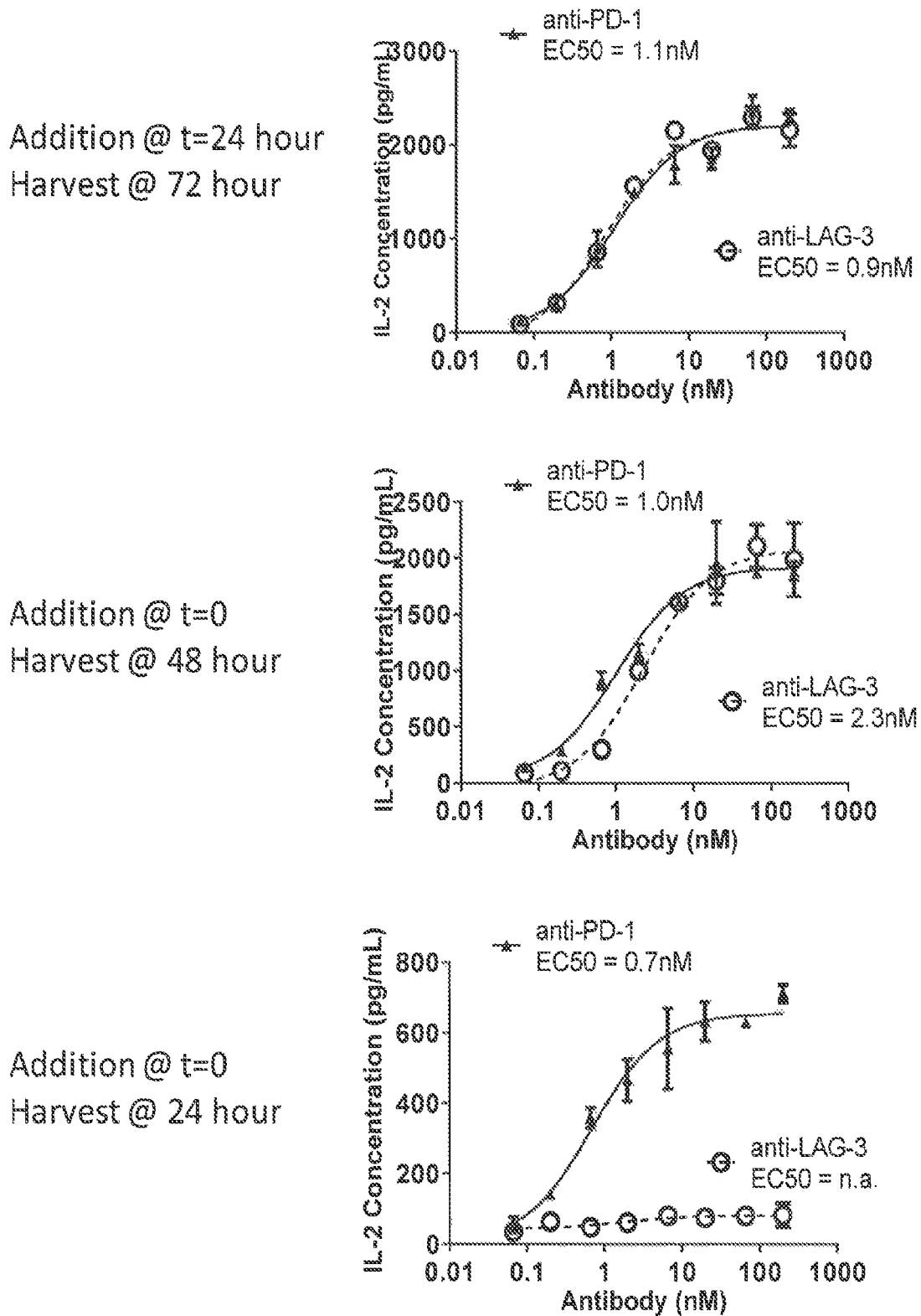
FIG. 2A depicts IL-2 secretion by CD4+ T-cells in a mixed lymphocyte reaction (MLR) assay at varying concentrations of Anti PD-1 or Anti-LAG-3 antibodies.
Figure 2B:
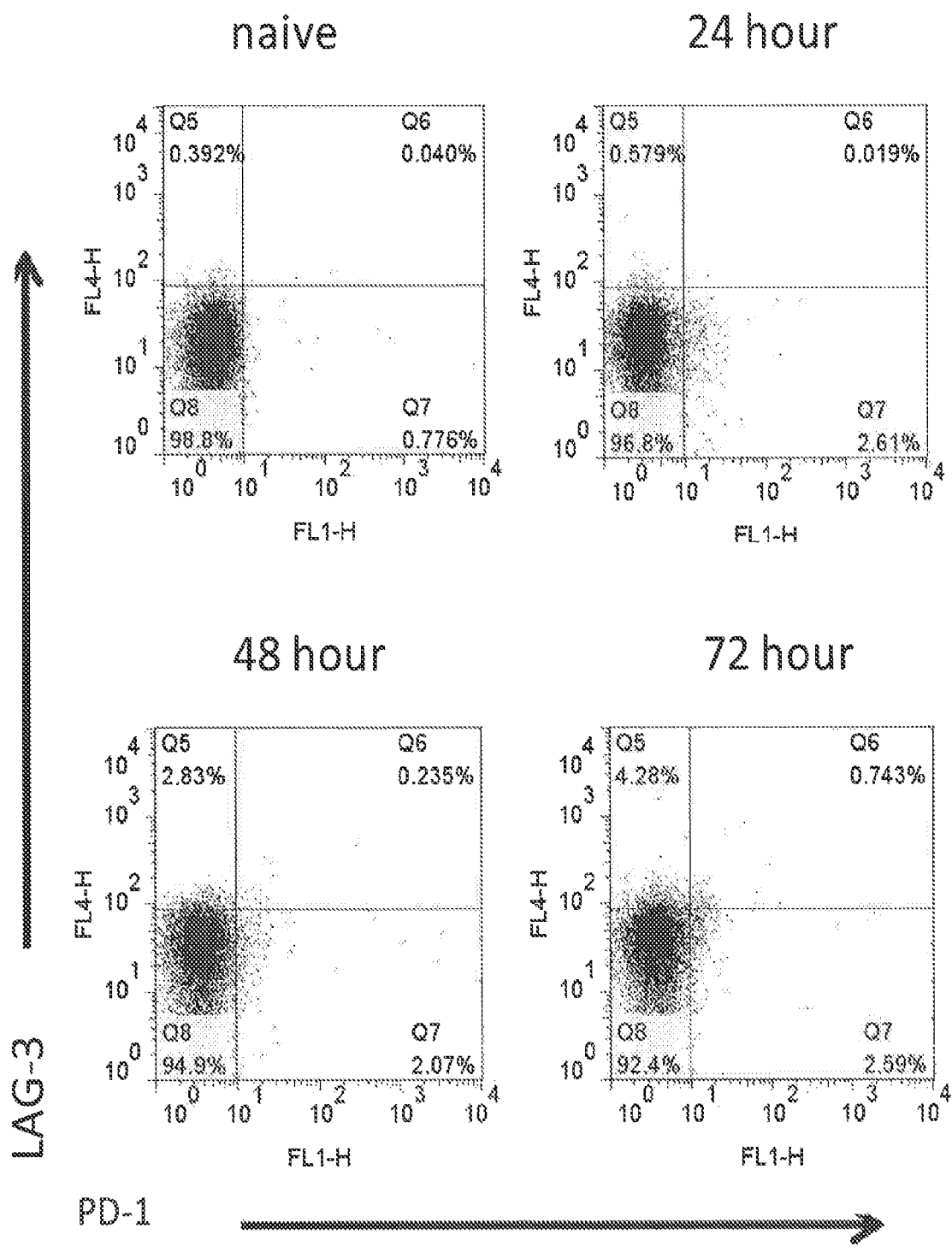
FIG. 2B depicts LAG-3 and PD-1 expression on CD4+ T-cells prior to (naïve) or subsequent to (24, 48, and 72 hour) exposure to dendritic cells.

Antagonism of LAG-3 and PD-1 was expected to result in increased T-cell activation as measured by increased IL-2 production. When added at the start of the assay, the anti-PD-1 antibody increased IL-2 secretion at both 24 and 48 hours post antibody addition, while the anti-LAG-3 antibody increased IL-2 secretion when measured at 48 hours in the MLR assay, but not at 24 hours. When inhibitory anti-LAG-3 or anti-PD-1 antibodies were added at 24 hours after starting the co-culture and harvested at 72 hours, both antibodies were active and the EC50 appeared to be equivalent (FIG. 2A). This correlates with expression as increased PD-1 expression is observed at 24-72 hours, while LAG-3 appears to be expressed later in the assay at 48 and 72 hours (FIG. 2B).

The results of this example demonstrate that the effects of LAG-3 inhibition correlates with target expression, and that LAG-3 expression occurs temporally later than PD-1.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A Lymphocyte Activation Gene-3 (LAG-3) binding agent comprising:
    an immunoglobulin light chain variable ($V_L$) region comprising a light chain CDR1, a light chain CDR2, and a light chain CDR3 of SEQ ID NO:88; and
    an immunoglobulin heavy chain variable ($V_H$) region comprising a heavy chain CDR1, a heavy chain CDR2, and a heavy chain CDR3 of SEQ ID NO:182.

2. A Lymphocyte Activation Gene-3 (LAG-3) binding agent comprising:
    an immunoglobulin light chain variable ($V_L$) region comprising SEQ ID NO:88; and
    an immunoglobulin heavy chain variable ($V_H$) region comprising SEQ ID NO:182.

3. The LAG-3 binding agent of claim 1, wherein the LAG-3 binding agent is an antibody.

4. The LAG-3 binding agent of claim 1, wherein the LAG-3 binding agent is an antigen-binding antibody fragment.

5. The LAG-3 binding agent of claim 1, wherein the LAG-3 binding agent is an IgG4 antibody.

6. The LAG-3 binding agent of claim 2, wherein the LAG-3 binding agent is an antibody.

7. The LAG-3 binding agent of claim 2, wherein the LAG-3 binding agent is an antigen-binding antibody fragment.

8. The LAG-3 binding agent of claim 2, wherein the LAG-3 binding agent is an IgG4 antibody.

9. A pharmaceutical composition comprising the LAG-3 binding agent of claim 1 and a pharmaceutically acceptable carrier.

10. A pharmaceutical composition comprising the LAG-3 binding agent of claim 2 and a pharmaceutically acceptable carrier.

* * * * *